US008280214B2

(12) United States Patent
Yang et al.

(10) Patent No.: US 8,280,214 B2
(45) Date of Patent: Oct. 2, 2012

(54) NANOWIRES AND NANORIBBONS AS SUBWAVELENGTH OPTICAL WAVEGUIDES AND THEIR USE AS COMPONENTS IN PHOTONIC CIRCUITS AND DEVICES

(75) Inventors: Peidong Yang, El Cerrito, CA (US); Matt Law, Boulder, CO (US); Donald J. Sirbuly, Livermore, CA (US); Justin C. Johnson, Boulder, CO (US); Richard Saykally, Piedmont, CA (US); Rong Fan, Pasadena, CA (US); Andrea Tao, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 532 days.

(21) Appl. No.: 11/559,244

(22) Filed: Nov. 13, 2006

(65) Prior Publication Data

US 2007/0140638 A1    Jun. 21, 2007

Related U.S. Application Data

(63) Continuation of application No. PCT/US2005/017029, filed on May 13, 2005.

(60) Provisional application No. 60/571,416, filed on May 13, 2004, provisional application No. 60/643,612, filed on Jan. 12, 2005, provisional application No. 60/844,015, filed on Sep. 11, 2006.

(51) Int. Cl.
*G02B 6/10* (2006.01)
*G02B 6/42* (2006.01)
*G02B 6/12* (2006.01)

(52) U.S. Cl. ............. 385/129; 385/12; 385/27; 385/31; 385/14; 385/39; 385/42; 385/45; 385/50; 385/132; 977/700; 977/932

(58) Field of Classification Search .................. 385/12, 385/15, 27, 31, 32, 39, 45, 122, 129, 132, 385/141–142, 146, 42, 50, 123; 257/613; 372/39, 43.01; 977/700, 902, 932

See application file for complete search history.

(56) References Cited

U.S. PATENT DOCUMENTS

| 6,509,961 | B1 * | 1/2003 | Schroeder | 356/73.1 |
|---|---|---|---|---|
| 6,909,824 | B1 * | 6/2005 | Messica et al. | 385/30 |
| 2002/0009719 | A1 | 1/2002 | Walt et al. | |
| 2002/0031836 | A1 | 3/2002 | Feldstein | |
| 2002/0175408 | A1 * | 11/2002 | Majumdar et al. | 257/734 |
| 2003/0068134 | A1 * | 4/2003 | Gunn, III | 385/50 |
| 2003/0231826 | A1 * | 12/2003 | Boyd et al. | 385/27 |
| 2004/0008944 | A1 * | 1/2004 | Johannessen et al. | 385/45 |
| 2006/0029979 | A1 | 2/2006 | Bai et al. | |

FOREIGN PATENT DOCUMENTS

WO    2005114282 A2    12/2005

* cited by examiner

*Primary Examiner* — Uyen Chau N Le
*Assistant Examiner* — Michael P Mooney
(74) *Attorney, Agent, or Firm* — John P. O'Banion

(57) ABSTRACT

Nanoribbons and nanowires having diameters less than the wavelength of light are used in the formation and operation of optical circuits and devices. Such nanostructures function as subwavelength optical waveguides which form a fundamental building block for optical integration. The extraordinary length, flexibility and strength of these structures enable their manipulation on surfaces, including the precise positioning and optical linking of nanoribbon/wire waveguides and other nanoribbon/wire elements to form optical networks and devices. In addition, such structures provide for waveguiding in liquids, enabling them to further be used in other applications such as optical probes and sensors.

3 Claims, 47 Drawing Sheets

FIG. 1A  FIG. 1B

Figure 1C:
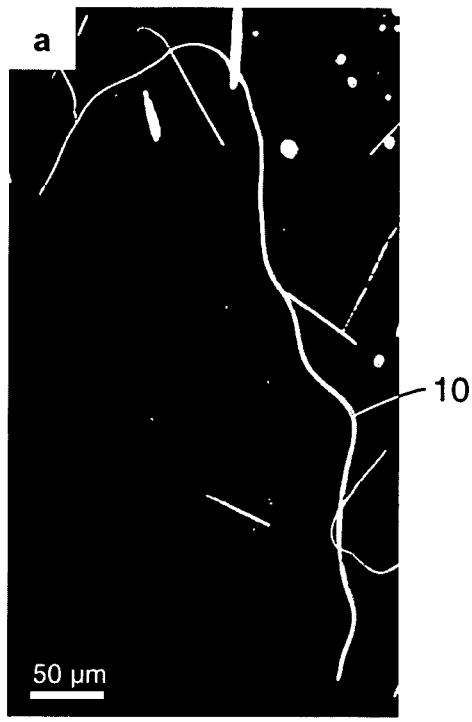

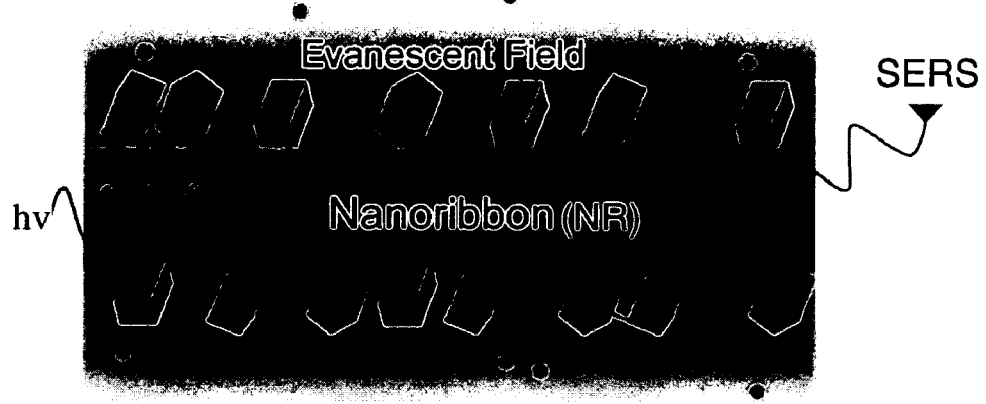
FIG. 14A
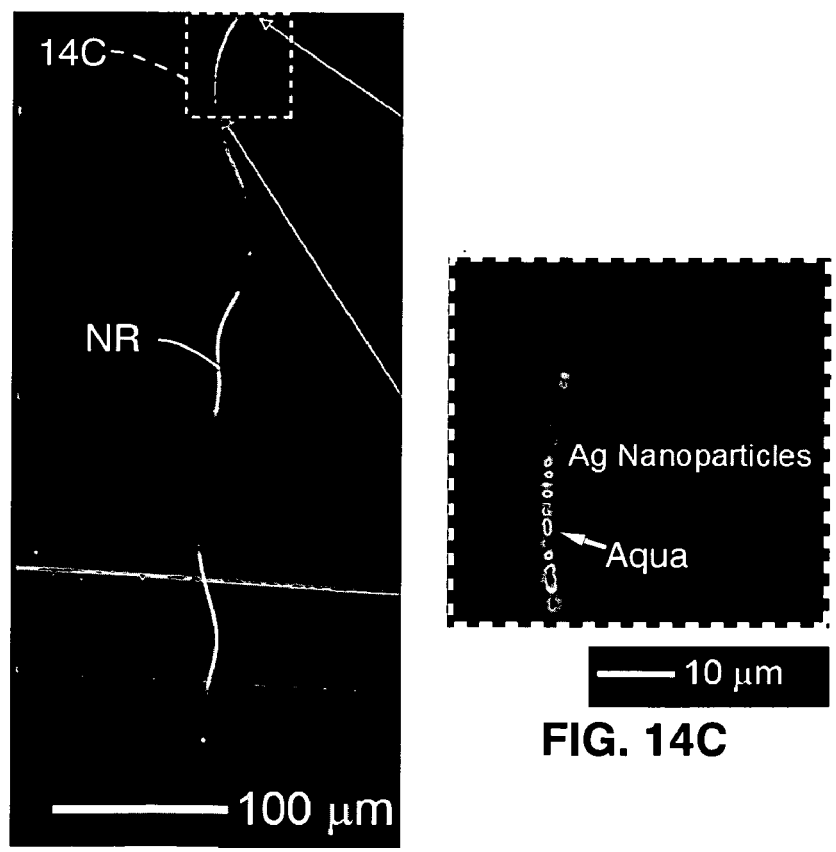
FIG. 14C
FIG. 14B

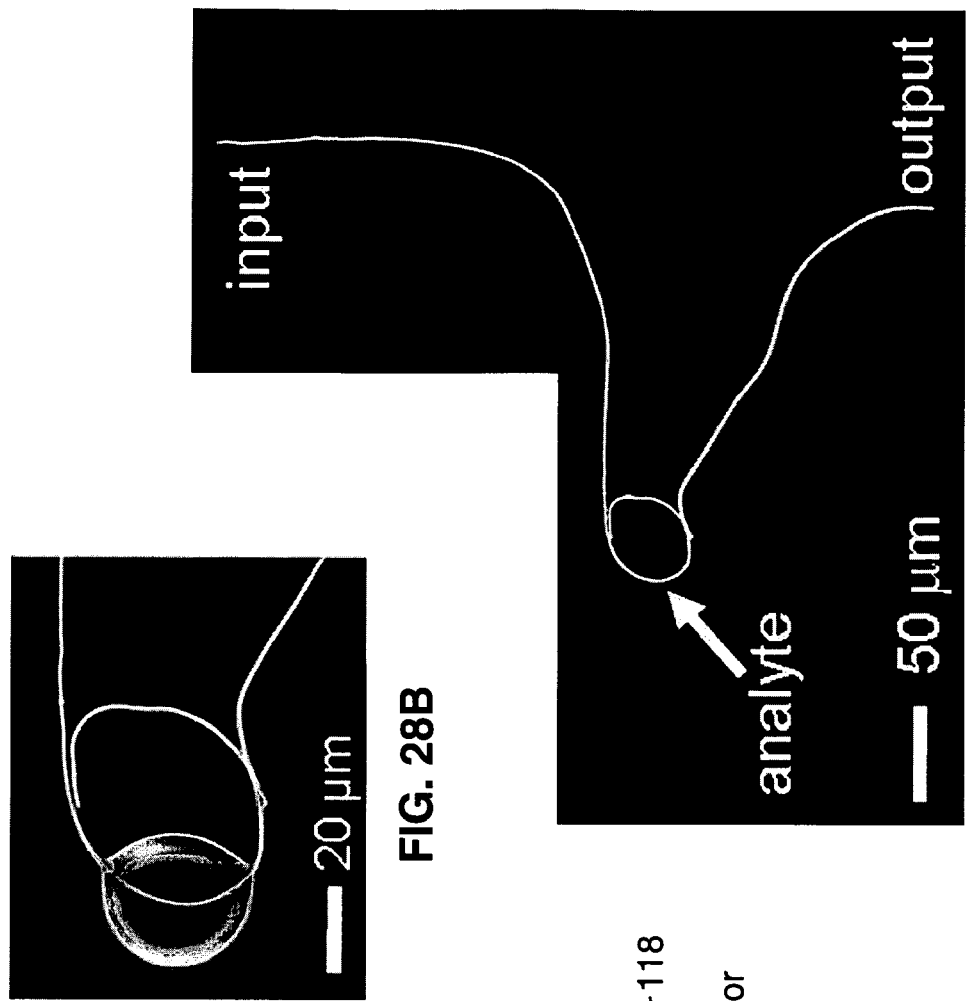
FIG. 28C
FIG. 28B
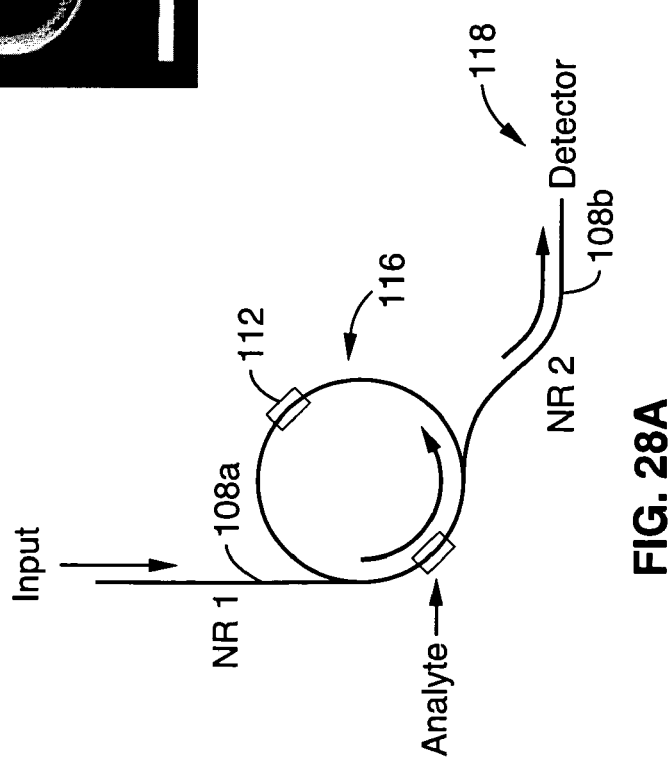
FIG. 28A

NANOWIRES AND NANORIBBONS AS SUBWAVELENGTH OPTICAL WAVEGUIDES AND THEIR USE AS COMPONENTS IN PHOTONIC CIRCUITS AND DEVICES

CROSS-REFERENCE TO RELATED APPLICATIONS

This application claims priority from, and is a 35 U.S.C. § 111(a) continuation-in-part of, co-pending PCT international application serial number PCT/US2005/017029 filed on May 13, 2005 which in turn claims priority from U.S. provisional application Ser. No. 60/571,416 filed on May 13, 2004, incorporated herein by reference in its entirety, and from U.S. provisional application Ser. No. 60/643,612 filed on Jan. 12, 2005, incorporated herein by reference in its entirety. Priority is claimed to each of the foregoing applications, and priority is also claimed to U.S. provisional application Ser. No. 60/844,015 filed on Sep. 11, 2006, incorporated herein by reference in its entirety.

This application is also related to PCT international publication number WO 2005/114282 A2, published on Dec. 1, 2005, incorporated herein by reference in its entirety.

STATEMENT REGARDING FEDERALLY SPONSORED RESEARCH OR DEVELOPMENT

This invention was made with Government support under Contract No. DE-FG02-02ER-46021 awarded by the Department of Energy, Grant No. DE-AC02-05CH11231 awarded by the Department of Energy, and Contract No. DMR-0092086 awarded by the National Science Foundation. The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to optical waveguides, and more particularly to nanoribbons and nanowires employed as subwavelength optical waveguides as well as optical probes, sensors, routers and other devices based on nanoribbon/wire optical waveguides. This invention also pertains generally to optical sensors which utilize the evanescent field of a single-crystalline nanoribbon waveguide.

2. Description of Related Art

Chemically synthesized nanowires represent a unique class of building blocks for the construction of nanoscale electronic and optoelectronic devices. Since nanowire synthesis and device assembly are typically separate processes, nanowires permit more flexibility in the heterogeneous integration of different materials than standard silicon technology allows, although the assembly itself remains a major challenge. The toolbox of nanowire device elements is growing and currently includes various types of transistors, light emitting diodes, lasers, and photodetectors. While the electrical integration of simple nanowire circuits using lithography has been demonstrated, optical integration, which promises higher speeds and greater device versatility, remains unexplored.

Photonics, the optical analogue of electronics, shares the logic of miniaturization that drives research in semiconductor and communications technology. The ability to manipulate pulses of light within sub-micron spaces is vital for highly integrated light-based devices, such as optical computers, to be realized. Recent advances in using photonic bandgap and plasmonic phenomena to control the flow of light are impressive in this regard. However, both of these approaches typically rely on difficult and costly lithographic processes for device fabrication and are in early stages of understanding and development.

Compact, reusable chemical sensors are highly desirable for on-site detection in the field, including the identification of water contaminants, hazardous biochemical compounds or blood-serum content. Ideally, a sensing platform should be portable and employ several complementary sensing modalities that allow quantitative chemical identification of extremely small sample volumes. Optical spectroscopy is a powerful analytical tool for characterizing biological and chemical systems, but making a standard optical laboratory portable is a major challenge. However, with recent advances in the synthesis and assembly of nanomaterials, it is timely to begin integrating these materials into functional device architectures for sensing and monitoring. Of the well-studied inorganic nanostructures, chemically synthesized one-dimensional (1D) semiconductors have gained significant interest from the photonics community as passive and active components for miniaturized spectroscopic devices. This is due in part to their ability to guide a significant portion of the confined electromagnetic energy outside the cavity (i.e., in the evanescent field) while operating below the diffraction limit of light. Since the evanescent field travels efficiently through fluidic and air dielectrics, it is possible to integrate the waveguides into microfluidic devices and sense molecules located near the surface of the cavity.

One-dimensional semiconductor nanomaterials offer unique advantages over their zero- and two-dimensional counterparts because their geometric shapes allow them to capture and guide light over long distances. Trapping light in volumes smaller than the wavelength of light is essential to the miniaturization of optical characterization techniques. Materials currently being studied for this purpose include photonic crystals, high-index solids, and metal surfaces. However, engineering versatile, reusable optical devices from materials such as photonic crystals and metallic nanostructures remains challenging due to the difficulty in performing spectroscopy with the guided optical energy. In addition, the synthetic steps for producing these materials tend to be labor-intensive and involve costly lithographic techniques.

Fiber-based detection is a unique alternative to free-space sensing because it localizes chemical recognition at the surface of a waveguide. Among the most popular sensing schemes that rely on the evanescent field of a fiber are absorption and fluorescence. Typically these set-ups involve multimode silica fibers with diameters much larger than the free-space wavelength of light. The evanescent field in these experiments has been used to measure refractive indices of liquids, monitor volatile compounds in water and detect shifts in localized surface plasmon resonances of coupled metal colloids. Recently, it has been proposed to use subwavelength silica fibers in a Mach-Zehnder type interferometer to detect index changes caused by molecules interacting with the surface of the fibers. Though these various sensing configuration are promising for high sensitivity, fast cycling times and reversibility, they do not provide versatility in their spectroscopic detection or enable a chemical read-out of the analyte. To move beyond fiber sensors that operate solely as on/off detectors it is vital to develop materials that can sustain multiple analytical modes for chemical identification.

BRIEF SUMMARY OF THE INVENTION

A potentially simpler and equally versatile concept is to assemble photonic circuits from a collection of nanoribbon/nanowire elements that assume different functions, such as light creation, routing and detection. Accordingly, the present invention generally comprises a subwavelength optical waveguide formed from a nanoribbon or nanowire having a diameter that is less than the wavelength of light to be guided. Such a subwavelength waveguide can serve a fundamental element of photonic circuits of various types.

Chemically synthesized nanoribbons and nanowires have several features that make them good building blocks, including inherent one-dimensionality, a variety of optical and electrical properties, good size control, low surface roughness and, in principle, the ability to operate both above and below the diffraction limit. An important step toward integrated nanoribbon/wire photonics is to develop a nanoribbon/wire waveguide that can couple pairs of nanoribbon/wire elements and provide the flexibility in interconnection patterns that is needed to carry out complex tasks, such as logic operations.

Accordingly, one aspect of the invention is the assembly of photonic circuit elements from nanostructures such as $SnO_2$ nanoribbon and ZnO nanowire waveguides. In one embodiment, high aspect ratio (e.g., >1000) nanoribbons/nanowires with diameters below the wavelength of light (typically 100 nm to 400 nm) are used as waveguides of both their own internally generated photoluminescence (PL) and nonresonant UV/visible light emitted from adjacent, evanescently coupled, nanoribbons/wires or external laser diodes According to another aspect of the invention, the length, flexibility and strength of these single-crystalline structures enable them to be manipulated and positioned on surfaces to create various single-ribbon shapes and multi-ribbon optical networks, including ring-shaped directional couplers and nanoribbon/wire emitter-waveguide-detector junctions.

Another aspect of the invention is that the ability to manipulate the shape of active and passive nanoribbon/wire cavities provides a new tool for investigating the cavity dynamics of subwavelength structures. Moreover, future advances in assembling the diverse set of existing nanowire building blocks could lead to a novel and versatile photonic circuitry.

Another aspect of the invention is that nanoribbons/nanowires push subwavelength optical fibers beyond silica. The scores of materials that can be made in nanoribbon/wire form include active, passive, nonlinear and semiconducting inorganic crystals, as well as a wide variety of polymers. Simultaneous photon, charge carrier and spin manipulation is possible within and between nanowires of different compositions. Also, many of these materials have higher refractive indices than silica-based glasses, permitting light of a given wavelength to be confined within thinner structures for denser integration.

Another aspect of the invention is waveguiding in liquids using subwavelength nanoribbon/wire optical waveguides.

According to another aspect of the invention, nanoribbons/wires are freestanding, mechanically flexible elements that can be manipulated on surfaces or used as mobile probes in fluids. As such, they offer a type of versatility difficult to achieve with lithographically-defined structures that are permanently affixed to their substrates.

Another aspect of the invention is a nanoribbon/wire optical waveguide having a high aspect ratio and a diameter less than the wavelength of light to be guided. In one embodiment, the aspect ratio is greater than approximately 1000. In another embodiment, the diameter is in the range of approximately 100 nm to approximately 400 nm.

Another aspect of the invention is a subwavelength optical waveguide formed from a crystalline oxide nanoribbon/wire. In one embodiment, the nanoribbon/wire comprises $SnO_2$. In another embodiment, the nanoribbon/wire comprises ZnO. In still another embodiment, the nanoribbon/wire comprises GaN.

Another aspect of the invention is to provide a nanoribbon/wire laser and a nanoribbon/wire photodetector coupled by a nanoribbon/wire optical channel.

Another aspect of the invention is an optical waveguide comprising a nanoribbon/wire dispersed on an $SiO_2$ or mica substrate.

Another aspect of the invention is a method of forming a $SnO_2$ nanoribbon/wire waveguide.

Another aspect of the invention is a method of forming a ZnO nanoribbon/wire waveguide.

A further aspect of the invention is an apparatus for guiding light through liquid media, comprising a nanoribbon or nanowire waveguide. In one embodiment, the nanoribbon waveguide comprises a $SnO_2$ nanoribbon waveguide. In another embodiment, the nanowire waveguide comprises a ZnO nanowire waveguide. In a further embodiment, the waveguides comprise high dielectric waveguides. In still another embodiment, the nanowire waveguide comprises a GaN nanowire waveguide.

Another aspect of the invention is a probe or a sensor comprising a subwavelength nanostructure waveguide.

A further aspect of the invention is an optical router comprising at least two coupled nanoribbon waveguides. In one embodiment, the nanoribbon waveguides comprise $SnO_2$ nanoribbon waveguides.

Another aspect of the invention is an optical router comprising at least two coupled nanowire waveguides. In one embodiment, the nanowire waveguides comprise ZnO nanowire waveguides.

Still another aspect of the invention is an optical router comprising a network of nanoribbon waveguides configured to separate white light and route individual colors based on a short-pass filtering effect. In one embodiment, the nanoribbon waveguides comprise $SnO_2$ nanoribbon waveguides.

Another aspect of the invention is an optical crossbar grid comprising two pairs of orthogonal nanoribbon waveguides configured to conduct light through abrupt 90° angles. In one embodiment, the nanoribbon waveguides comprise $SnO_2$ nanoribbon waveguides.

The development of on-chip photonic sensors requires novel materials that control the flow of light through liquids with structures smaller than the wavelength of the light guided. One class of materials that shows excellent optical confinement in solutions and can be integrated into microfluidic devices is semiconductor nanowire waveguides.

Accordingly, another aspect of the invention is a microfluidic optical sensor that employs a nanowire or nanoribbon waveguide.

In one embodiment, the optical sensor is formed from a structure having a plurality of microfluidic channels, and a nanowire or nanoribbon waveguide coupled to the structure across the microfluidic channels.

In another embodiment, the optical sensor is formed from a flow cell structure having a plurality of microfluidic channels, and a single crystalline nanoribbon waveguide coupled to the structure across the microfluidic channels.

Another aspect of the invention is a method of fabricating a microfluidic sensor.

In one embodiment, the sensor is fabricated by providing a flow cell structure having a plurality of microfluidic channels, providing a nanowire or nanoribbon waveguide, positioning the waveguide across the channels, and coupling the waveguide to the flow cell structure.

In another embodiment, the sensor is fabricated by providing a $SnO_2$ nanoribbon waveguide, providing a polydimethylsiloxane (PDMS) microfluidic flow cell having a plurality of channels, positioning the nanoribbon waveguide across the channels and attaching the waveguide to the flow cell. For support, the structure can also bonded to a quartz substrate.

Another aspect of the invention is an optical sensing method.

In one embodiment, the method is carried out by providing an optical sensor comprising a flow cell structure having a plurality of microfluidic channels and a nanowire or nanoribbon waveguide positioned across the channels and coupled to the structure, flowing a material through said channels, and optically pumping the waveguide to generate evanescent wave emission through the channels.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1A-C illustrate optical waveguiding in a 715 μm long $SnO_2$ nanoribbon.

FIG. 2A-F illustrate panchromatic waveguiding in a 425 μm long nanoribbon.

FIG. 3A-G illustrate shape manipulation of nanoribbon waveguides.

FIG. 4A-H illustrate an ~600 μm long nanoribbon slightly suspended above a substrate that undergoes physical manipulation by an etched tungsten probe.

FIG. 5A-F illustrate dark-field images taken before and after manipulating a nanoribbon's cavity shape.

Figure 6A:
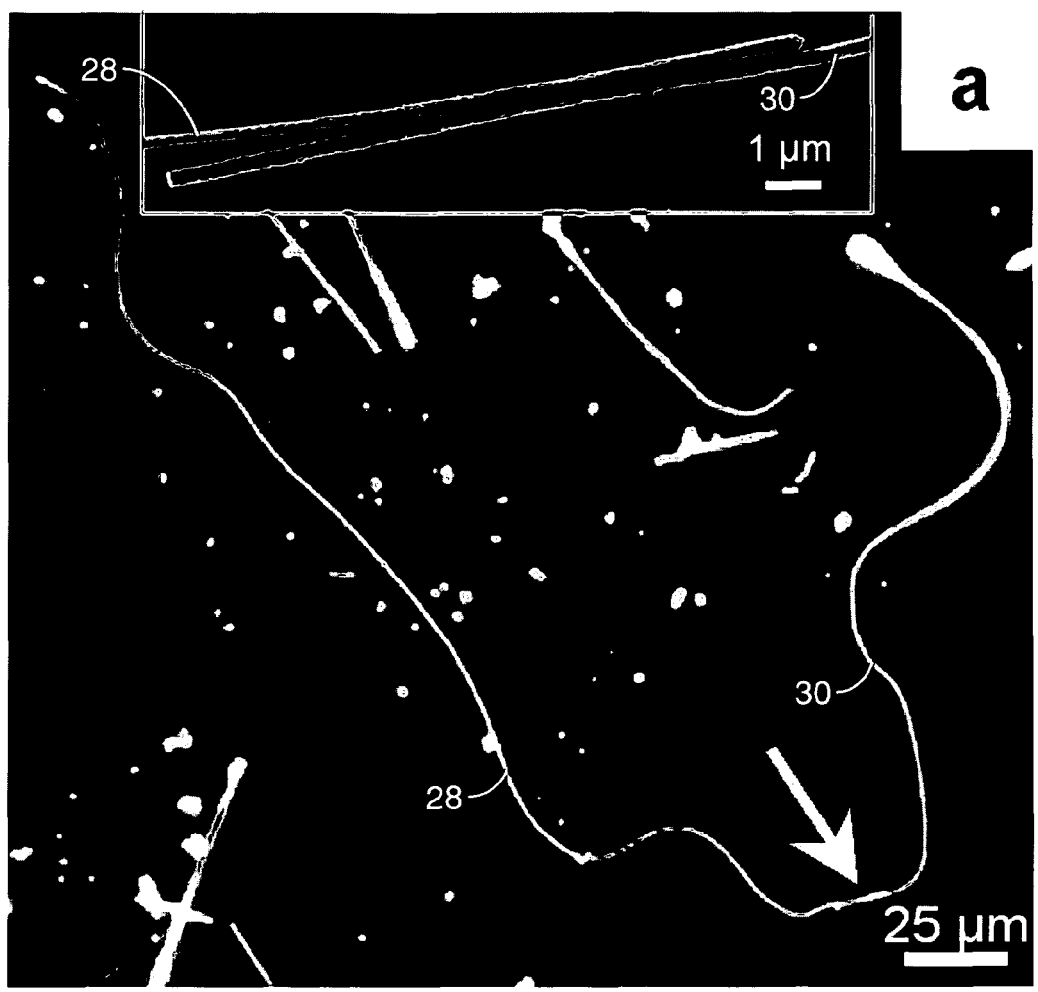
Figure 6B:
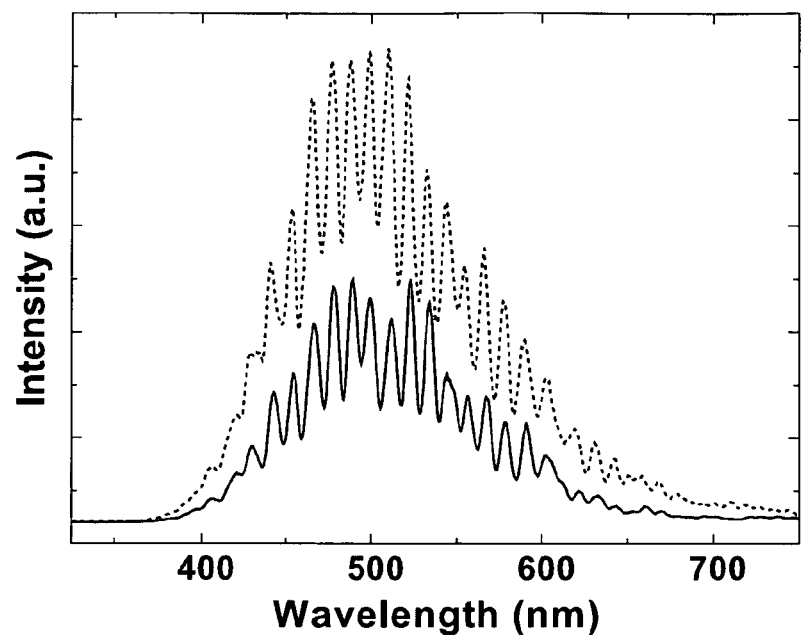
Figure 6C:
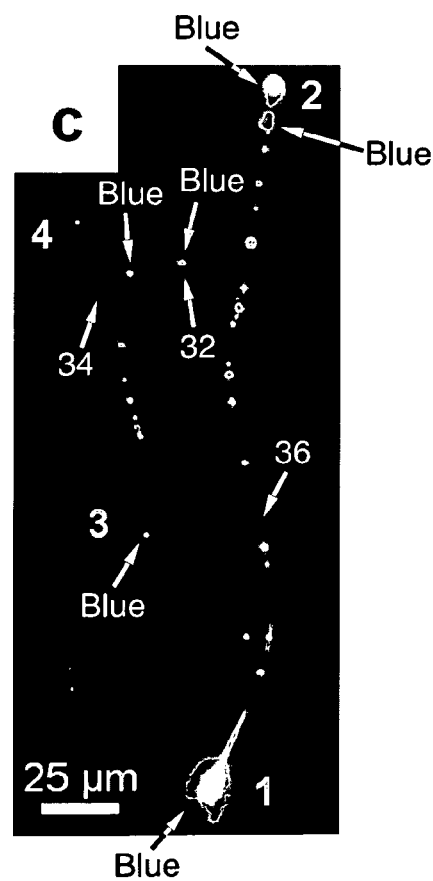

FIG. 6A-C illustrate nanoribbon coupling, optical components and devices.

Figure 7A:
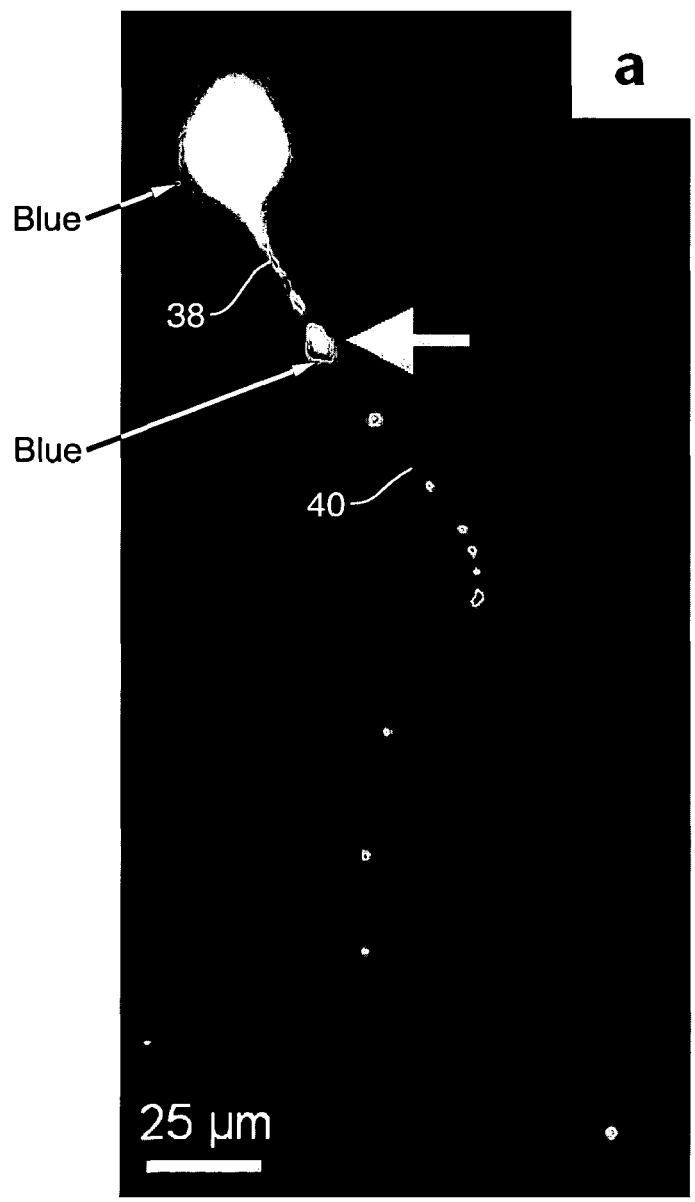
Figure 7B:
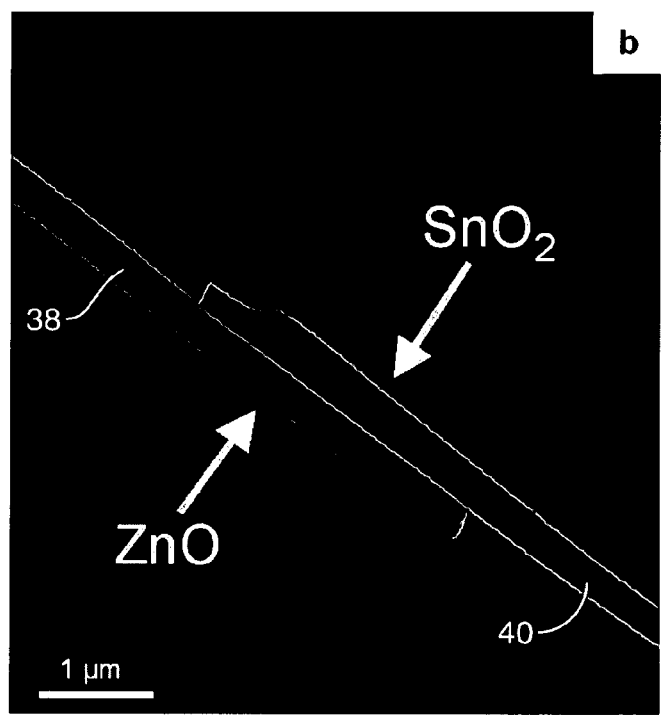
Figure 7C:
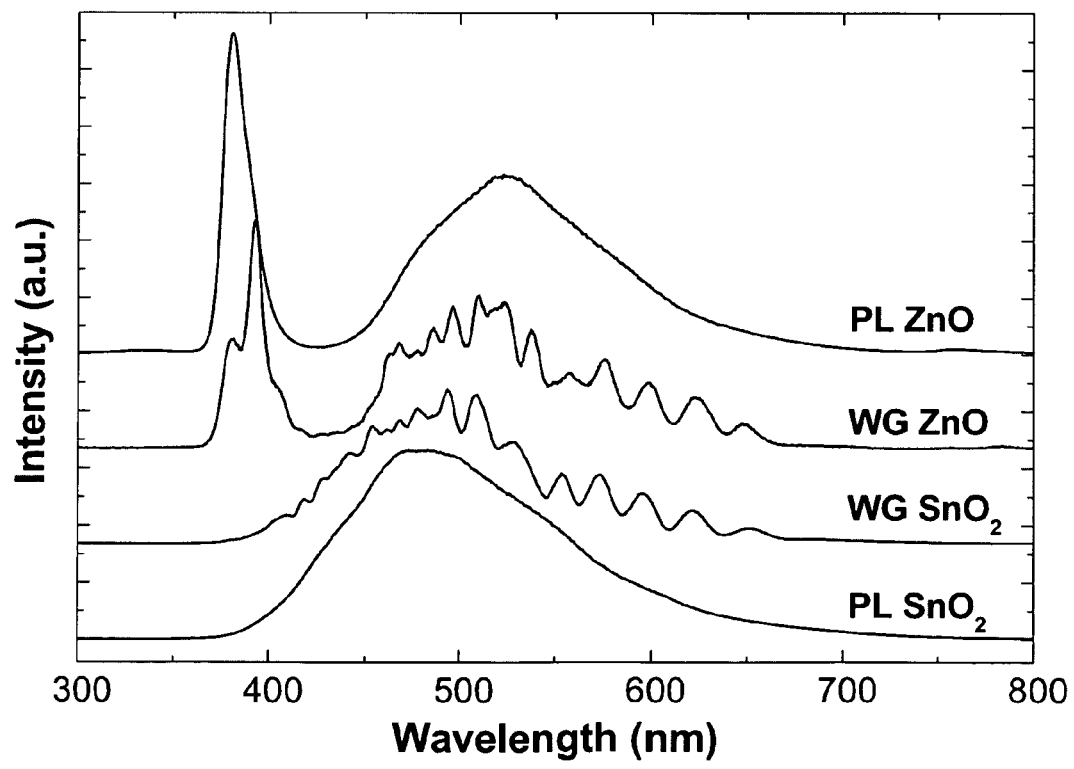

FIG. 7A-C show optical coupling between a ZnO nanowire and a $SnO_2$ nanoribbon waveguide.

Figure 8A:
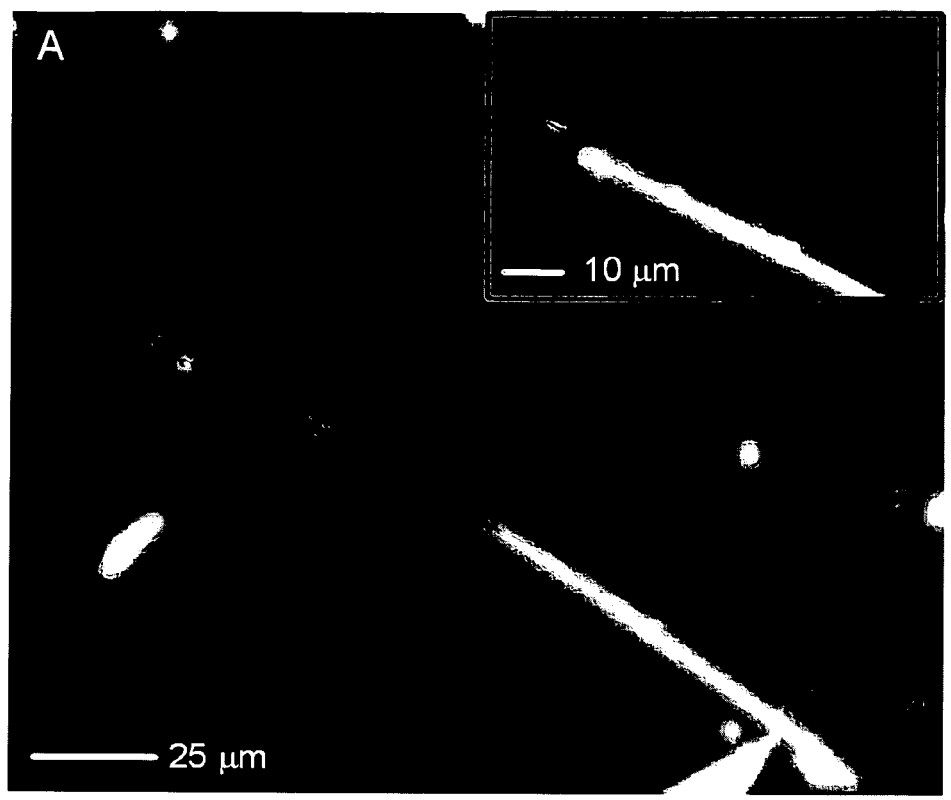
Figure 8B:
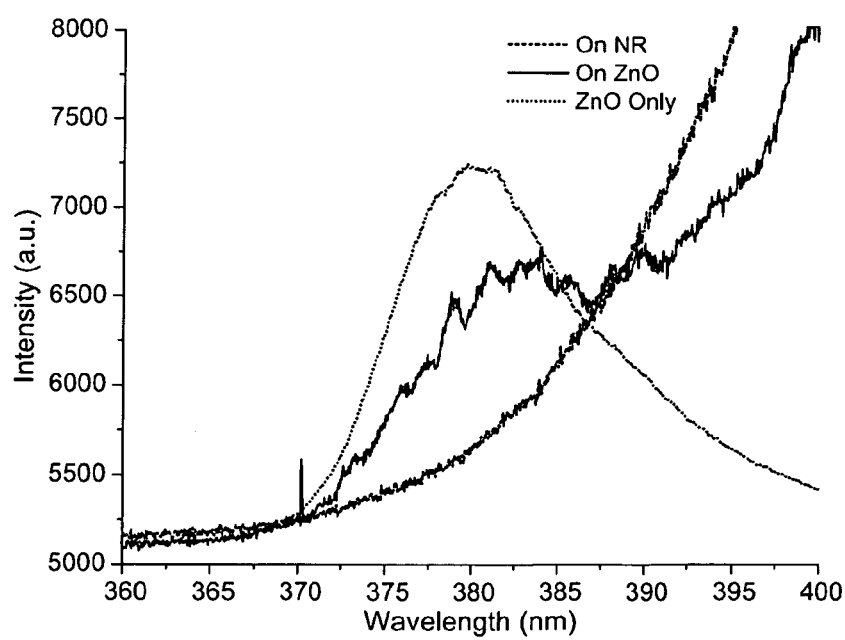

FIG. 8A-B show a hetero-junction created between a single ZnO nanowire and a $SnO_2$ nanoribbon.

Figure 9A:
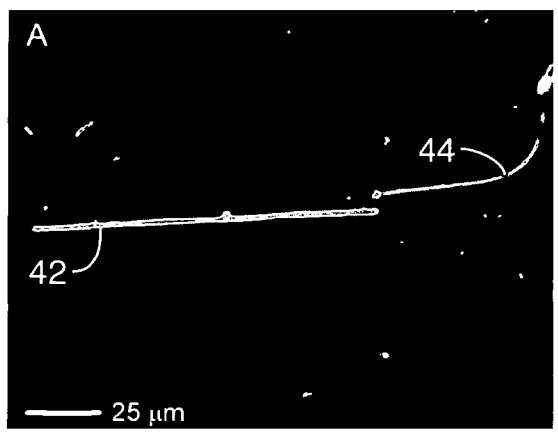
Figure 9B:
Figure 9C:
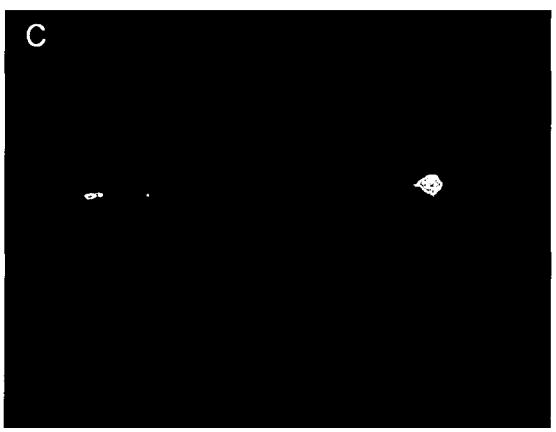

FIG. 9A-C show a $SnO_2/SnO_2$ junction created by coupling two nanoribbon waveguides at their end facets.

Figure 10A:
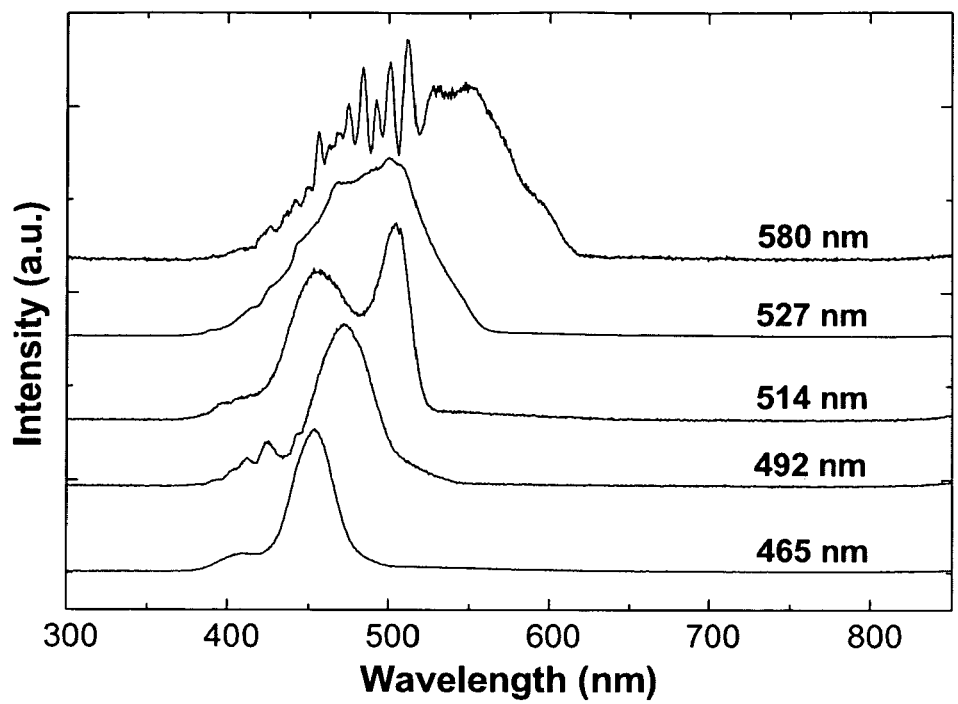
Figure 10B:
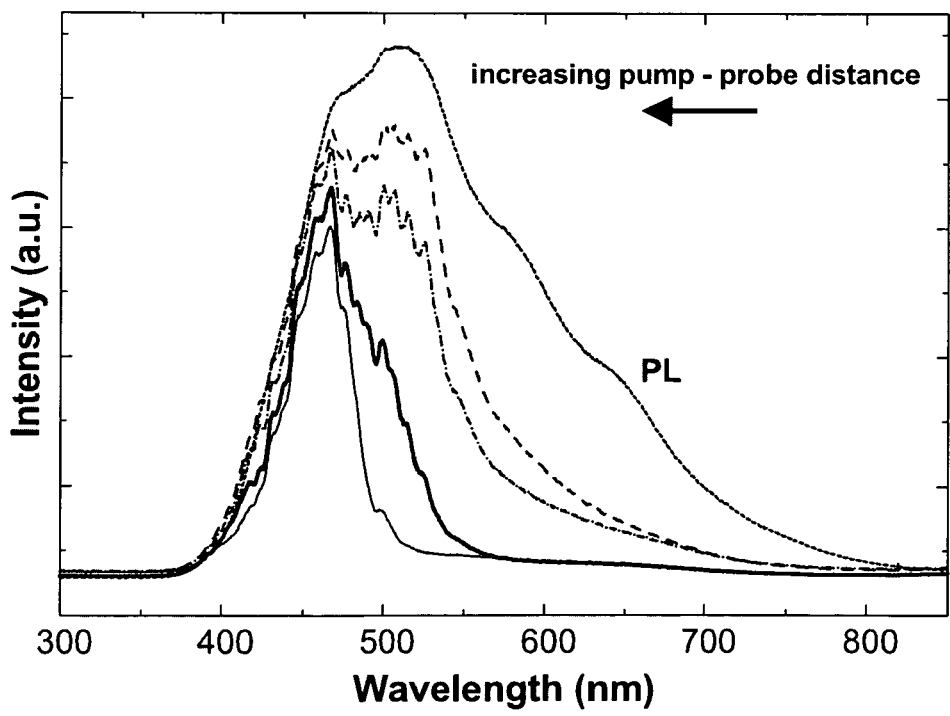

FIG. 10A-B illustrates nanoribbon short-pass filters.

Figure 11A:
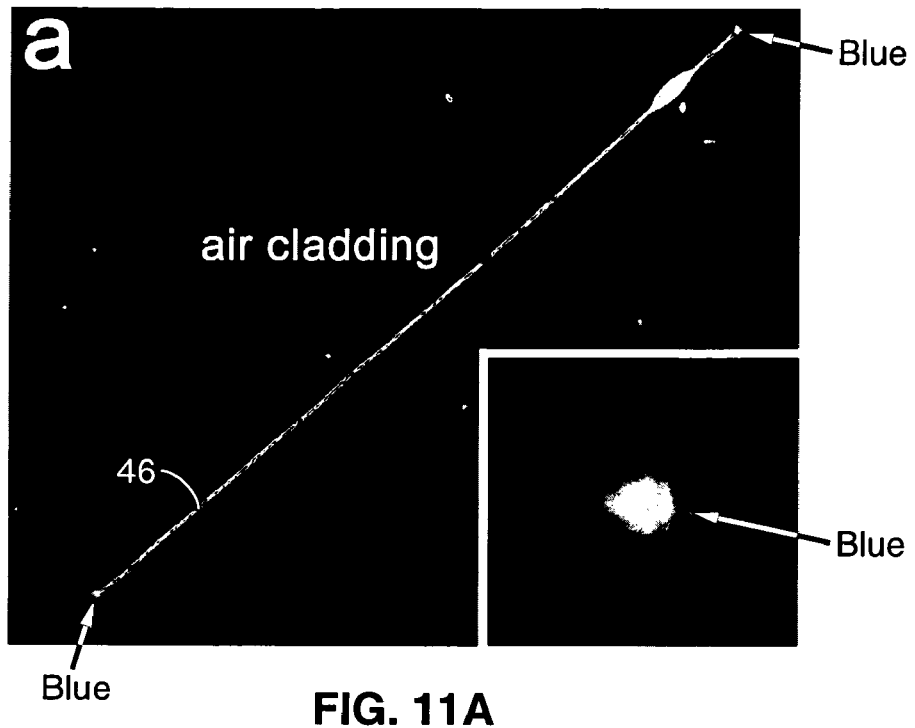
Figure 11B:
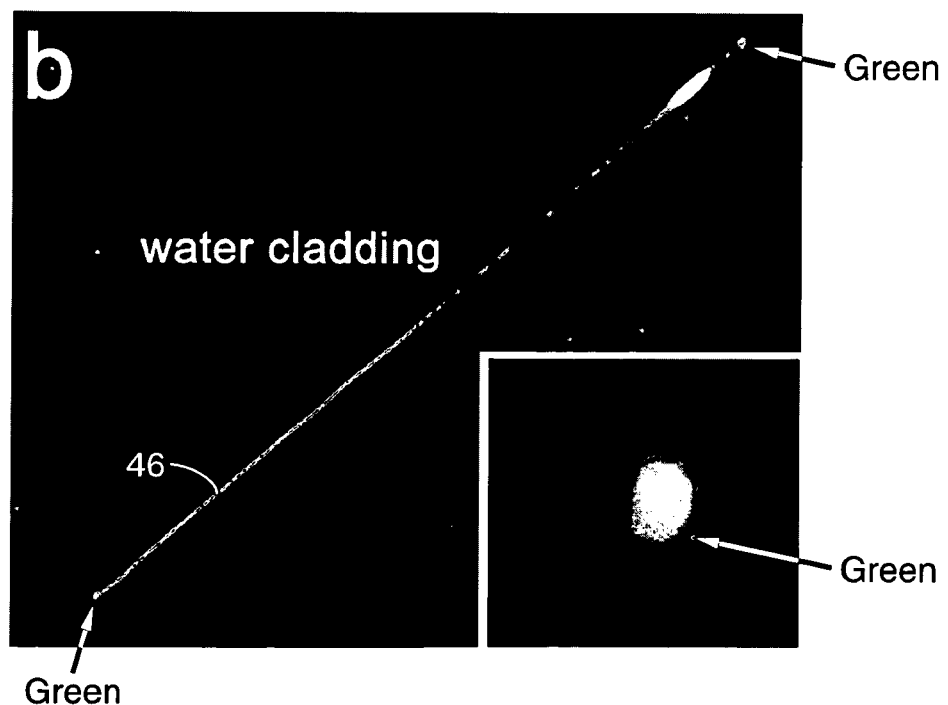
Figure 11C:
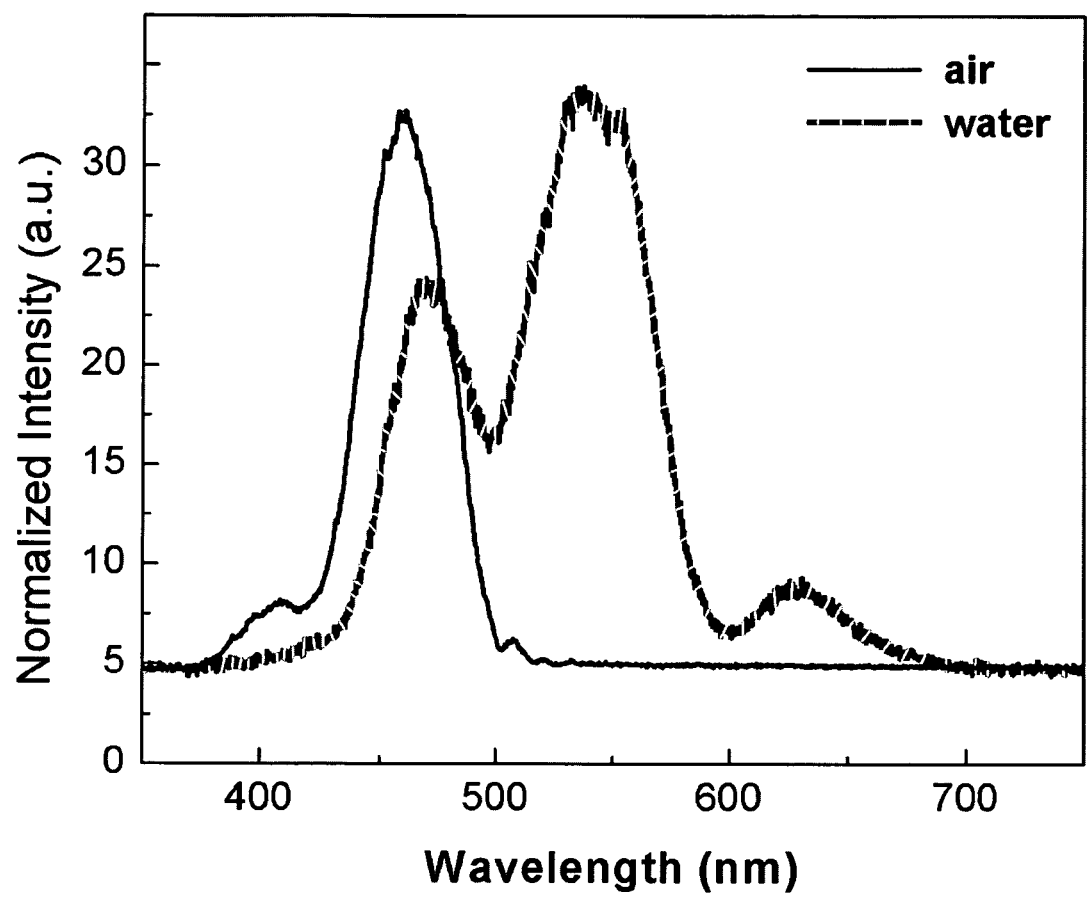

FIG. 11A-C illustrate waveguiding in water.

Figure 12A:
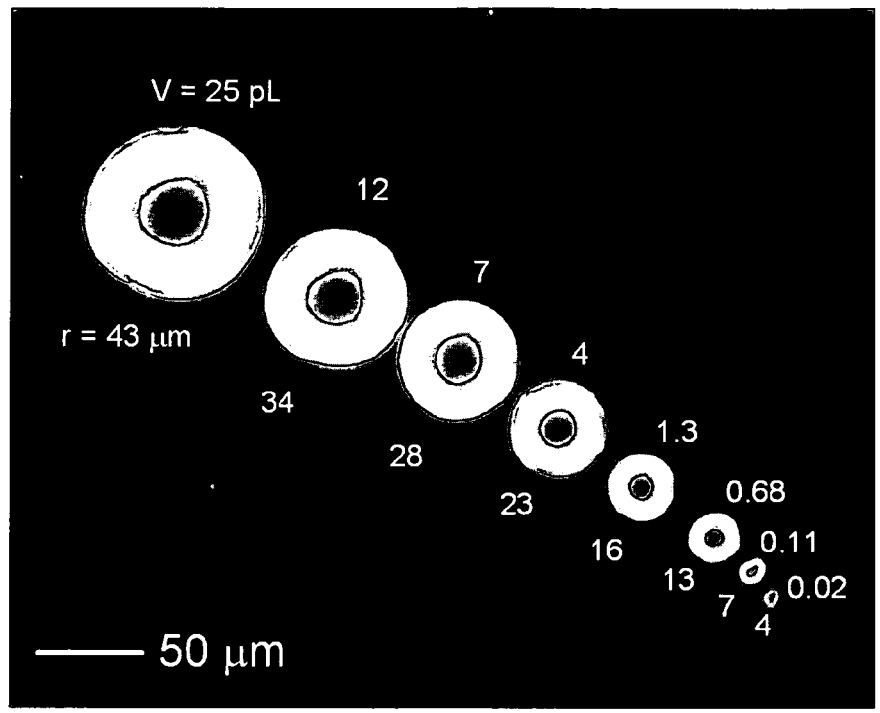
Figure 12B:
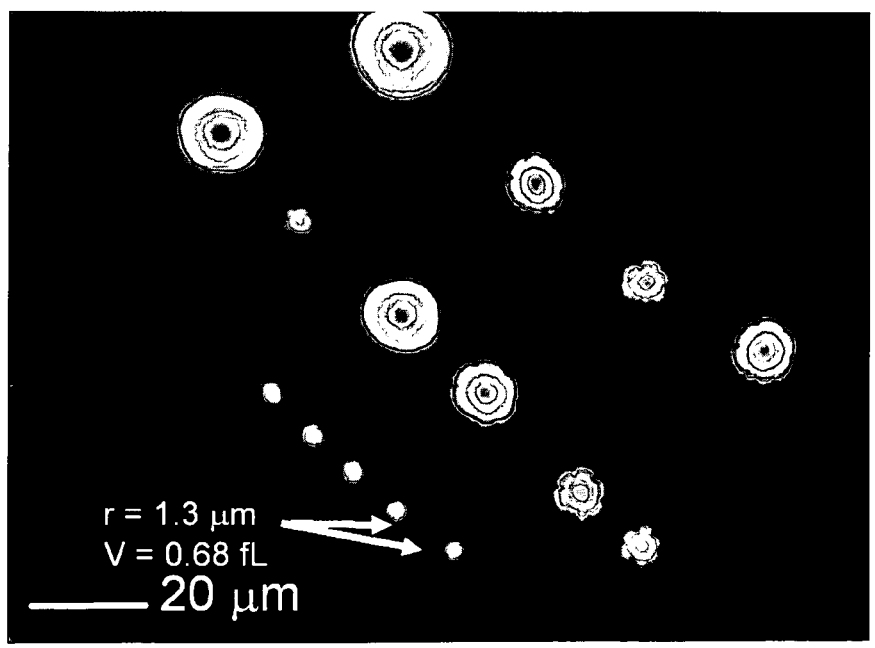

FIG. 12A-B show dark field images of waveguiding in water.

FIG. 13A-D shows fluorescence and absorbance detection of R6G with a nanoribbon cavity.

FIG. 14A-C illustrate the concept of SERS sensing with subwavelength waveguides.

Figure 15:
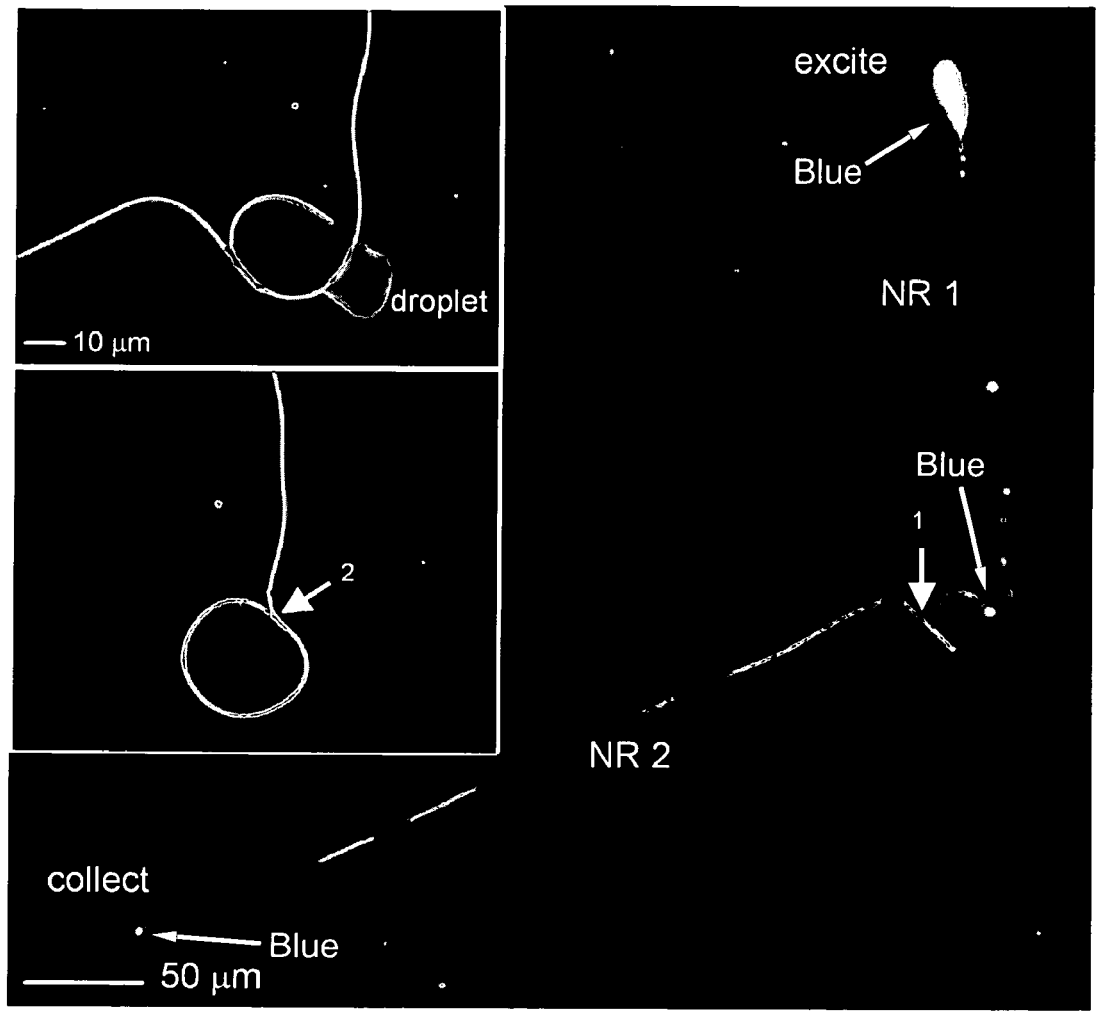

FIG. 15 shows PL/dark-field image of two nanoribbons (NR1 and NR2) evanescently coupled at arrow 1.

Figure 16A:
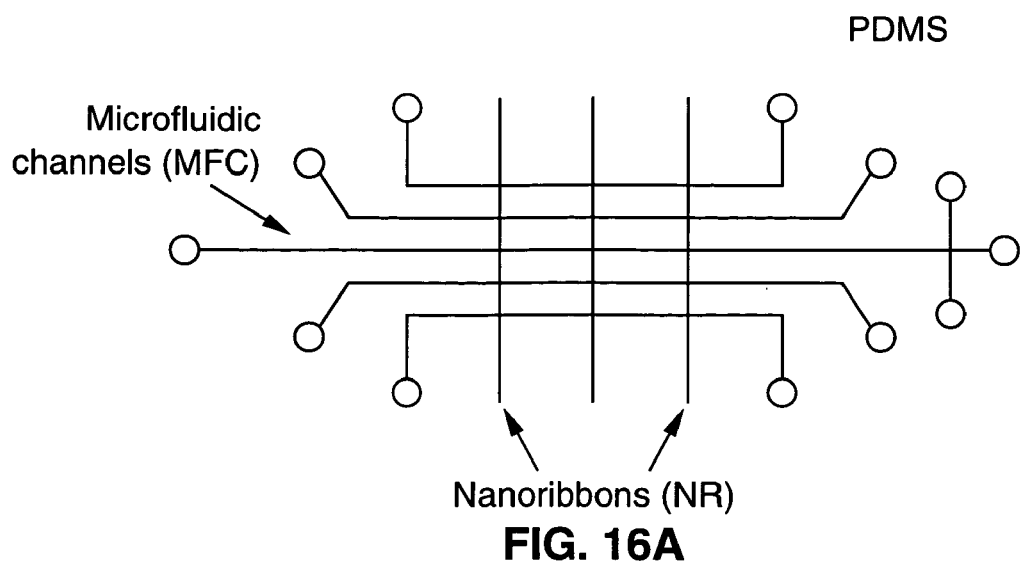
Figure 16B:
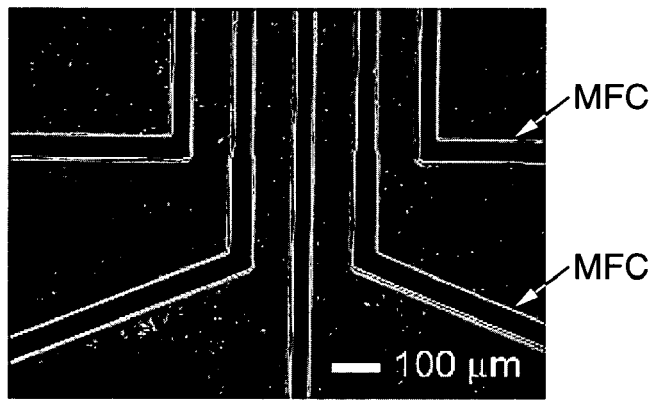
Figure 16C:
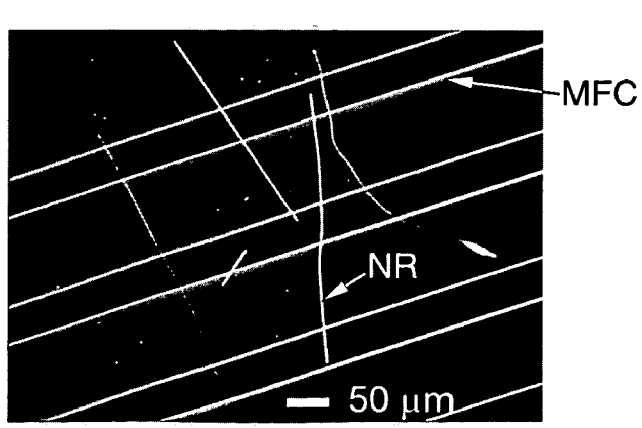

FIG. 16A-C illustrate the integration of waveguides into a fluidic device.

FIG. 17A-F illustrate the routing of GaN PL and lasing emission.

Figure 18A:
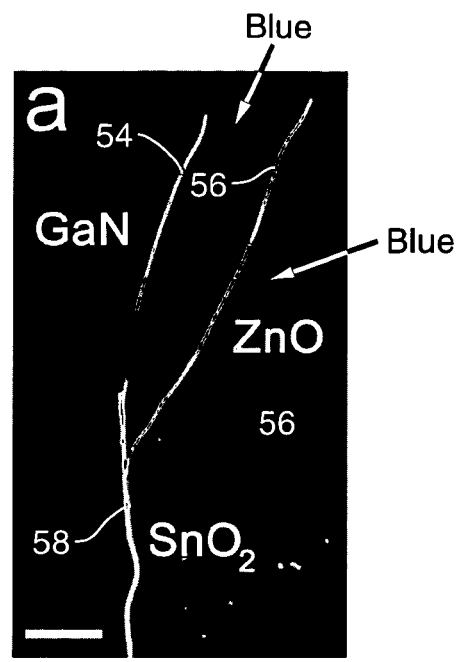
Figure 18B:
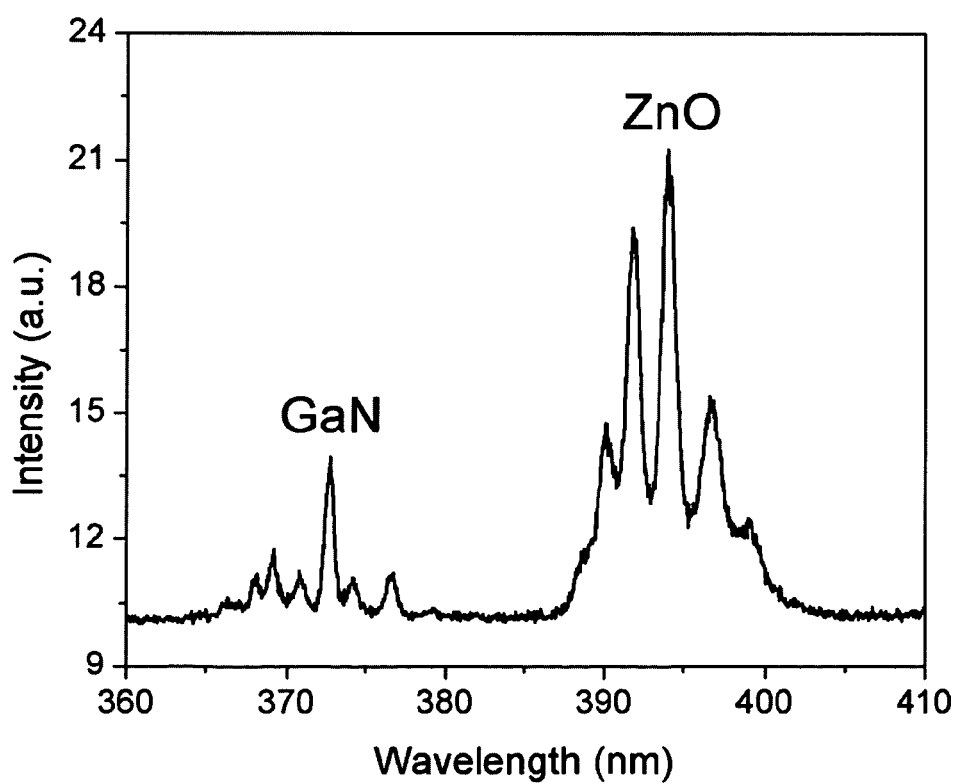

FIG. 18A-B illustrate multi-laser waveguiding.

Figure 19A:
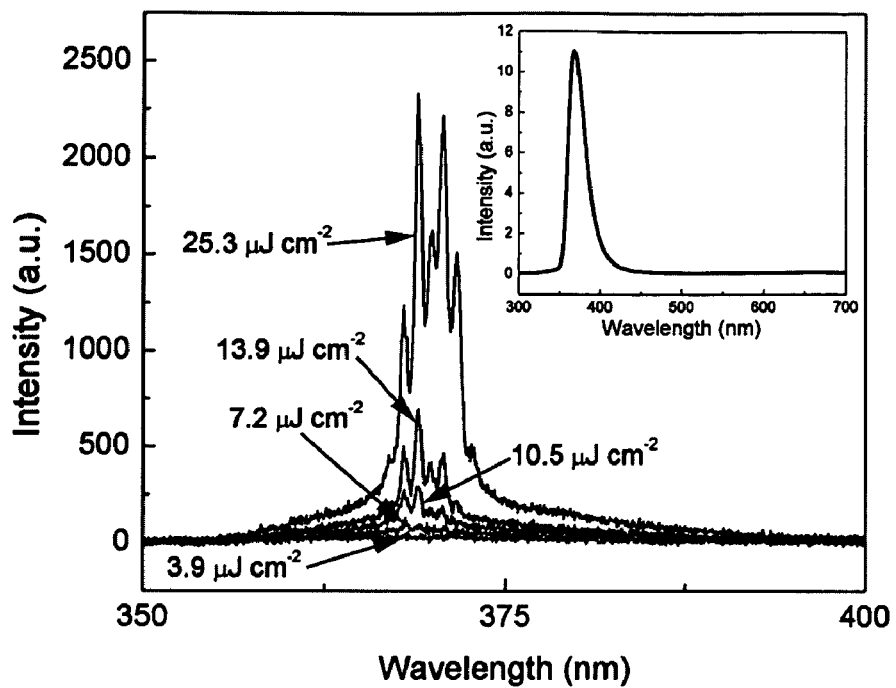
Figure 19B:
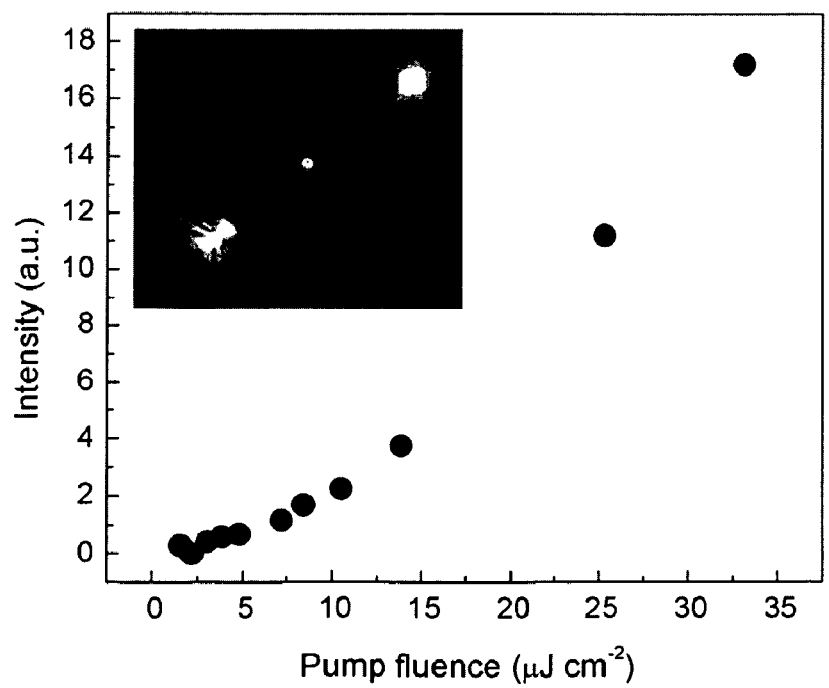
Figure 20A:
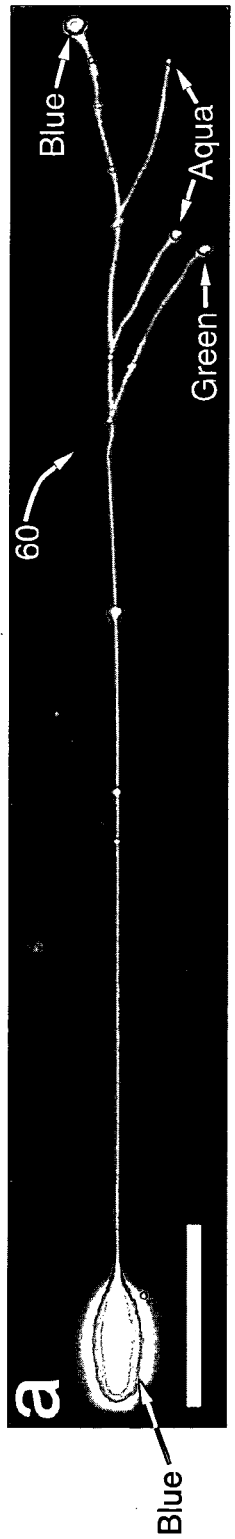
Figure 20C:
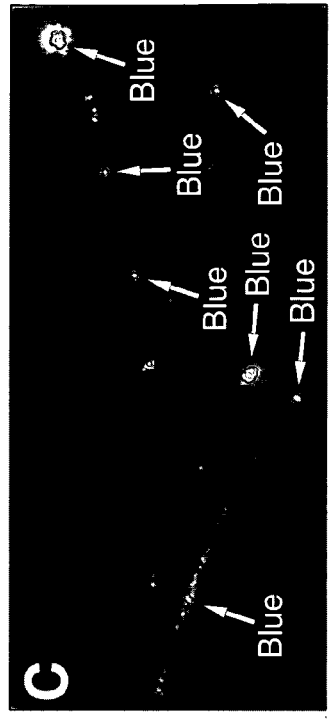
Figure 20E:
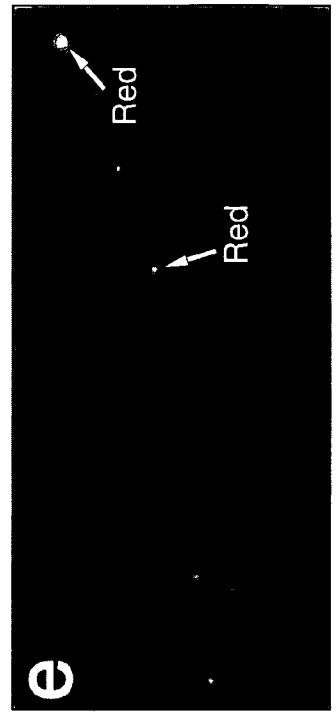
Figure 20B:
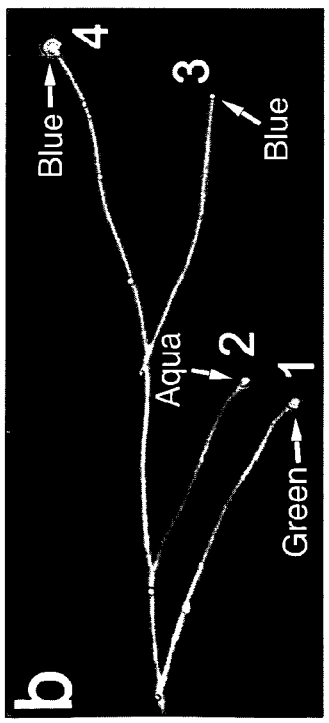
Figure 20D:
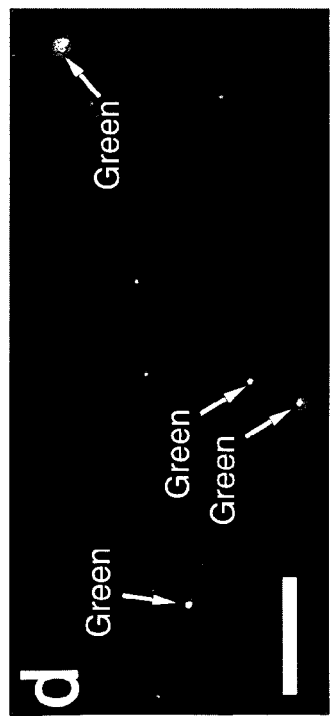

FIG. 19A-B illustrate GaN nanowire lasing.

FIG. 20A-E show color filtering in a nanoribbon network.

Figure 21:
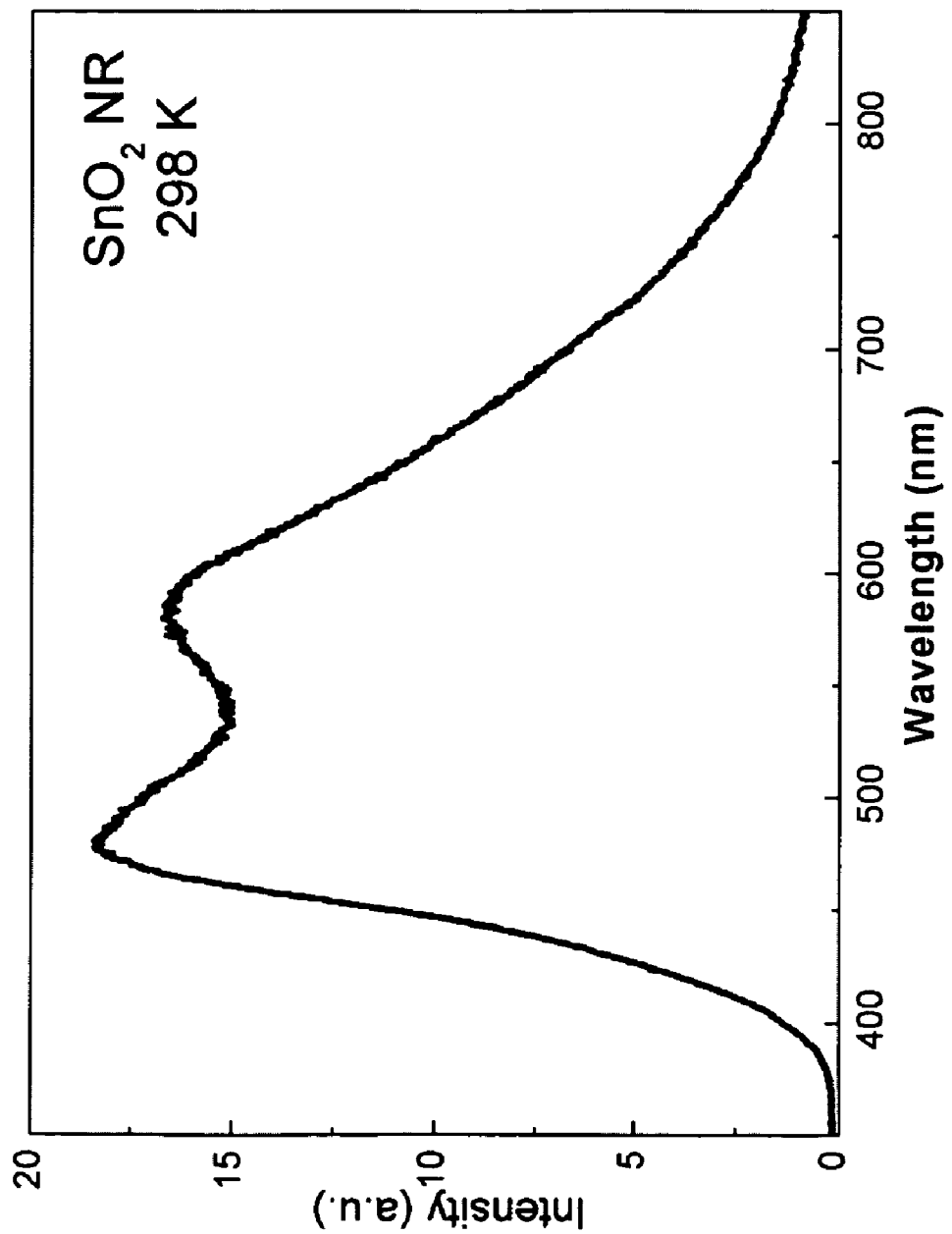

FIG. 21 is a typical PL spectrum of a $SnO_2$ nanoribbon, showing its two defect bands.

Figure 22B:
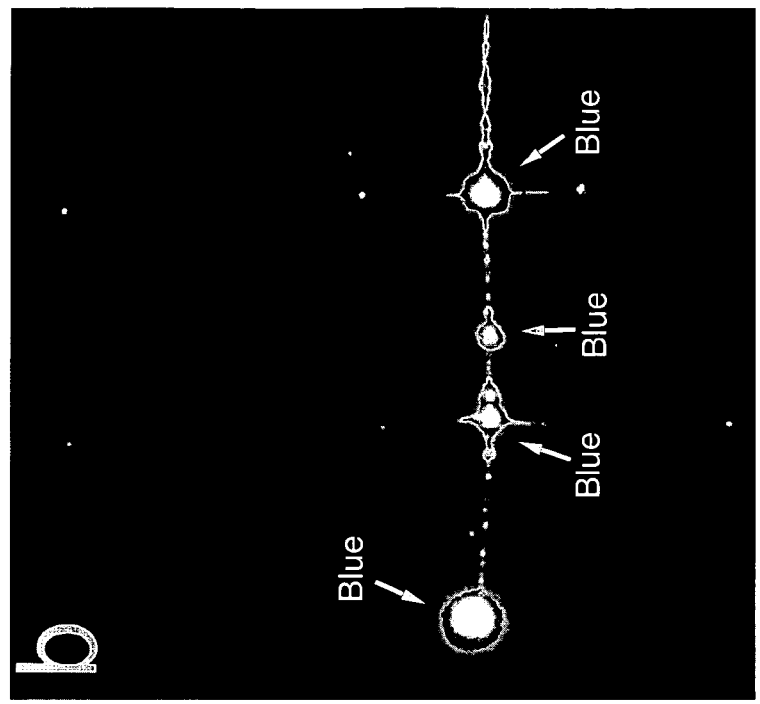
Figure 22A:
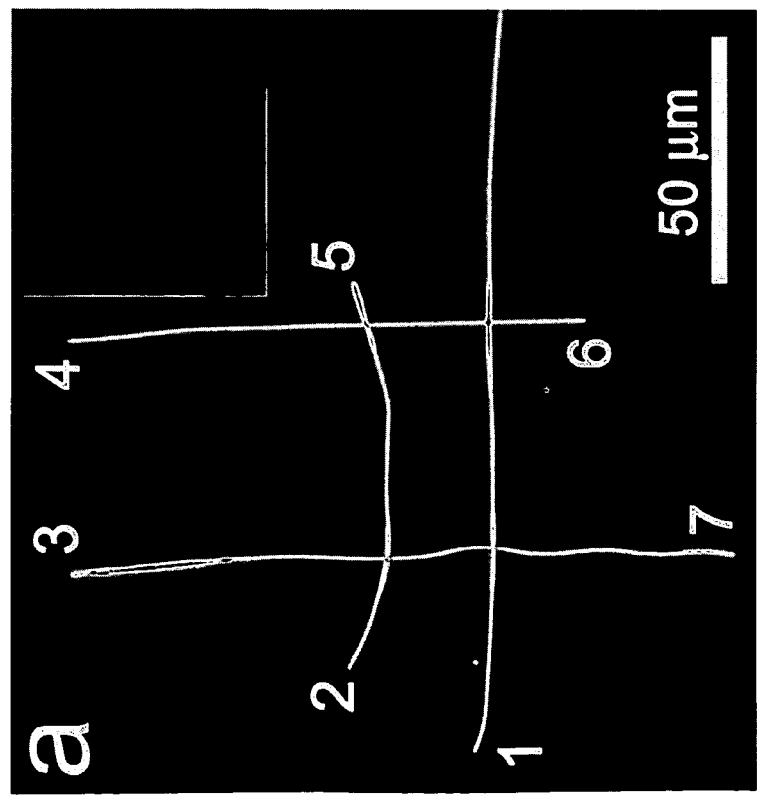

FIG. 22A-B illustrate optical routing in a rectangular nanoribbon grid.

Figure 23A:
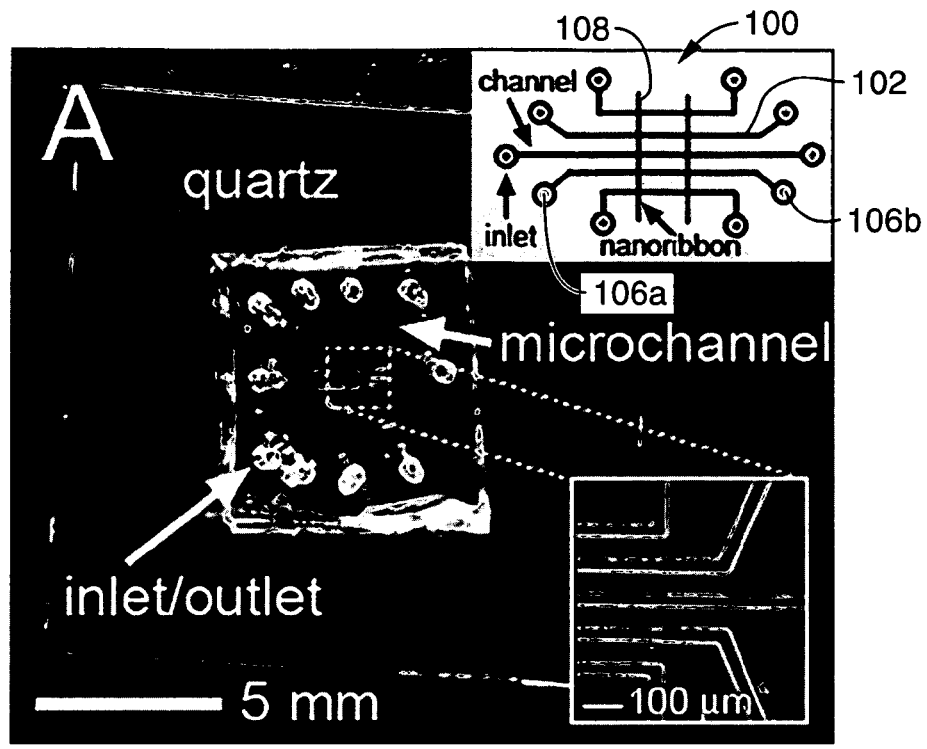
Figure 23B:
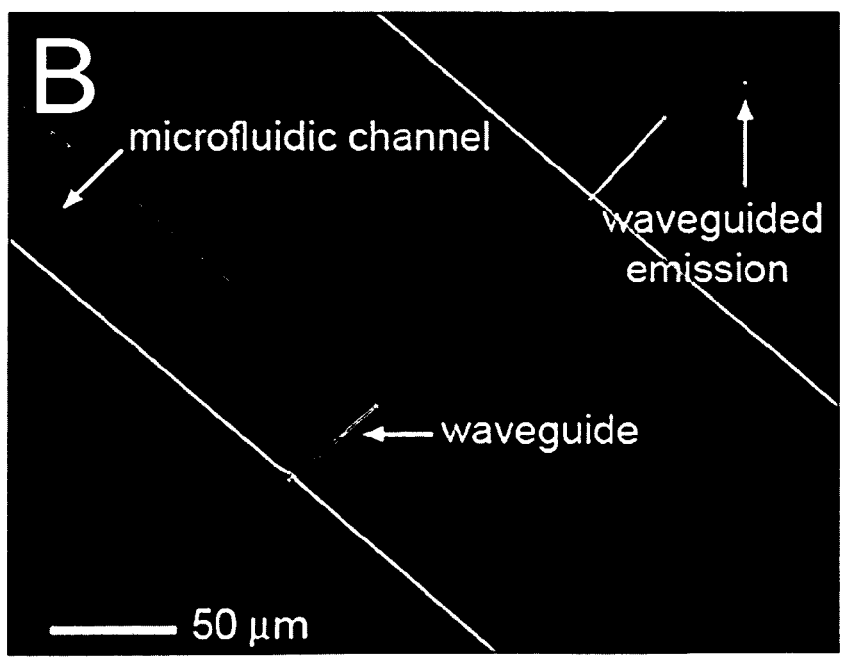
Figure 23C:
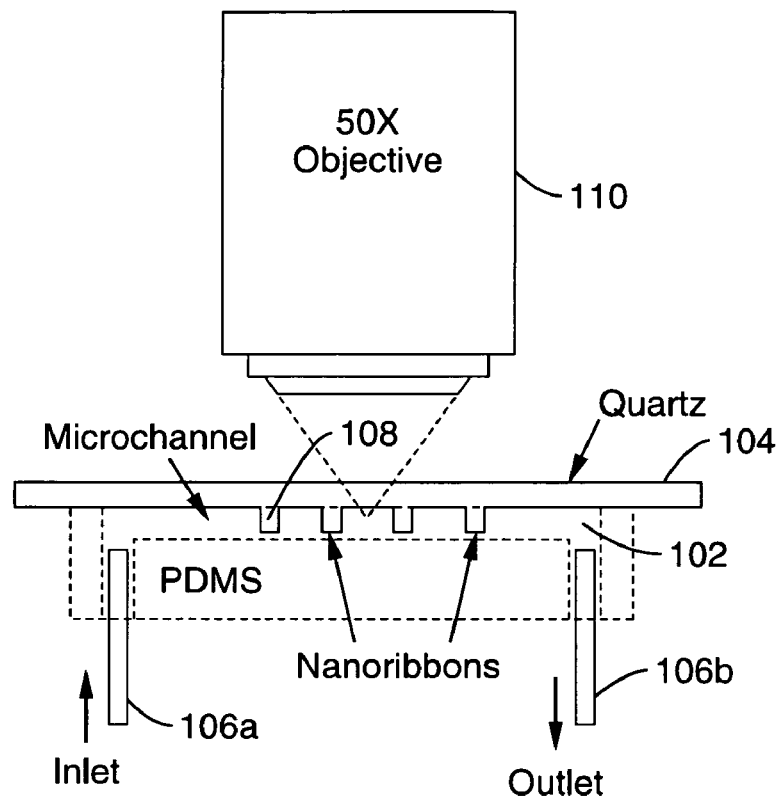

FIG. 23A-C illustrate a device layout of an evanescent field sensor according to the present invention.

FIG. 24A-H illustrate use of evanescent wave sensors in absorbance and fluorescence modes.

Figure 25A:
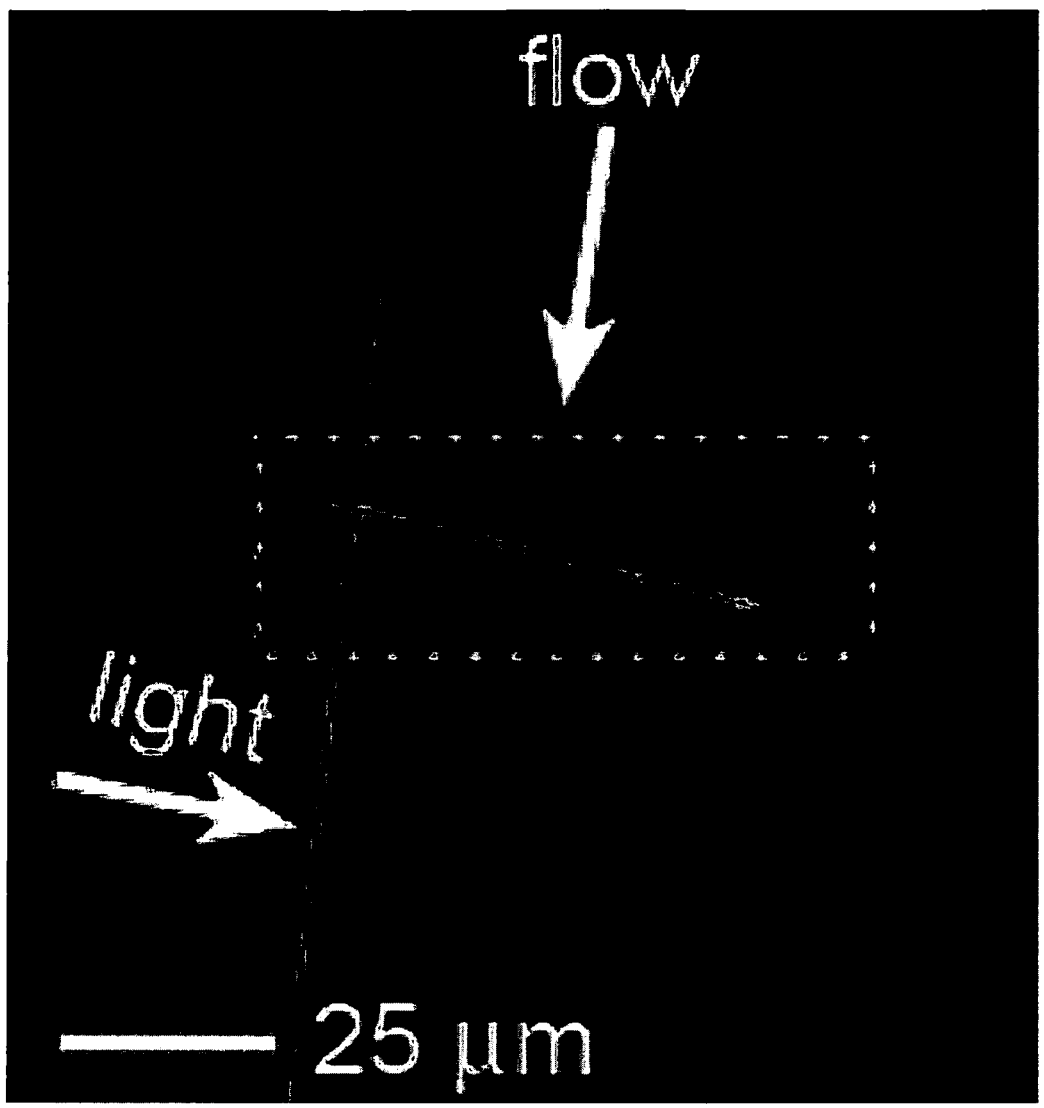
Figure 25B:
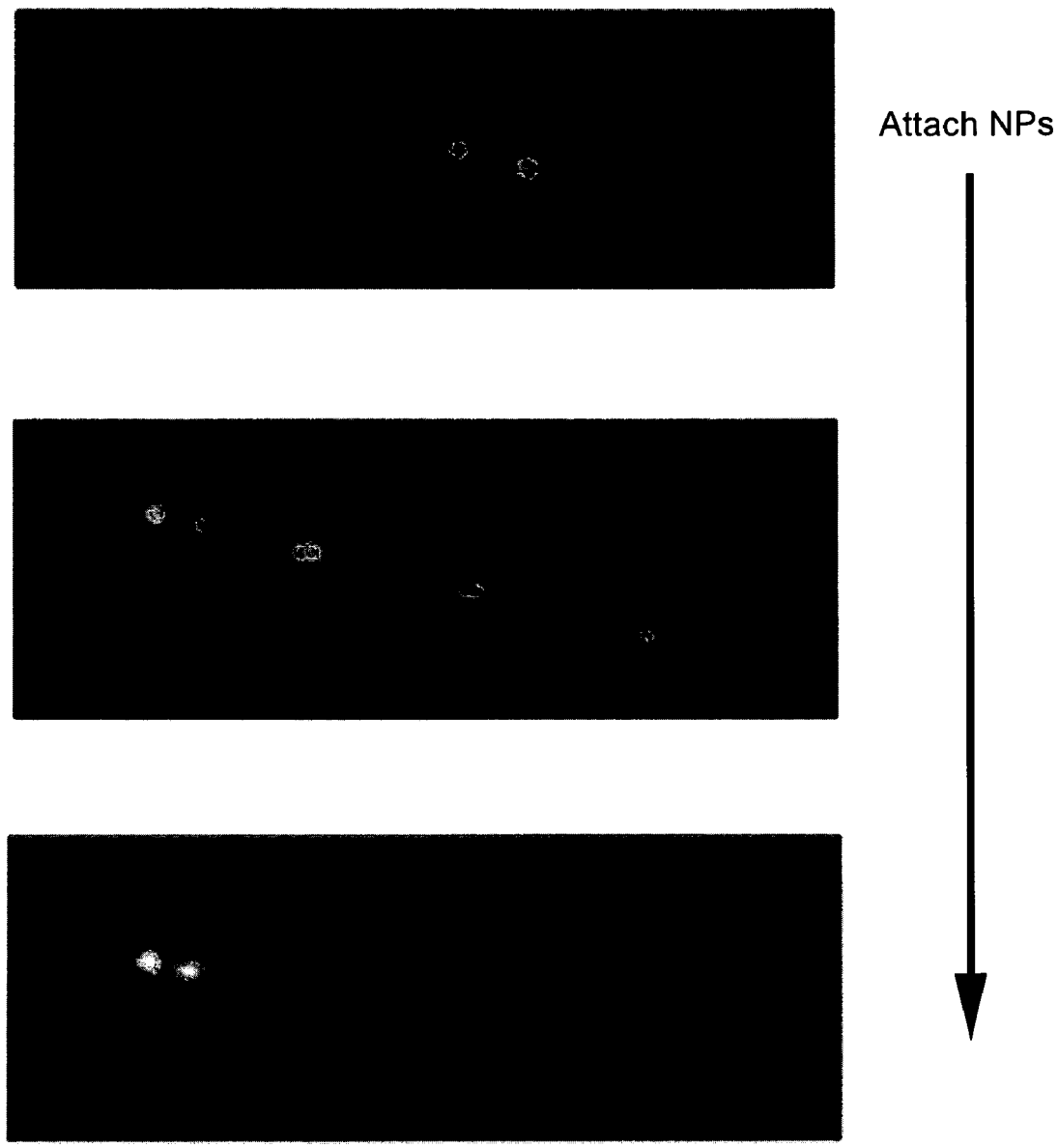
Figure 25C:
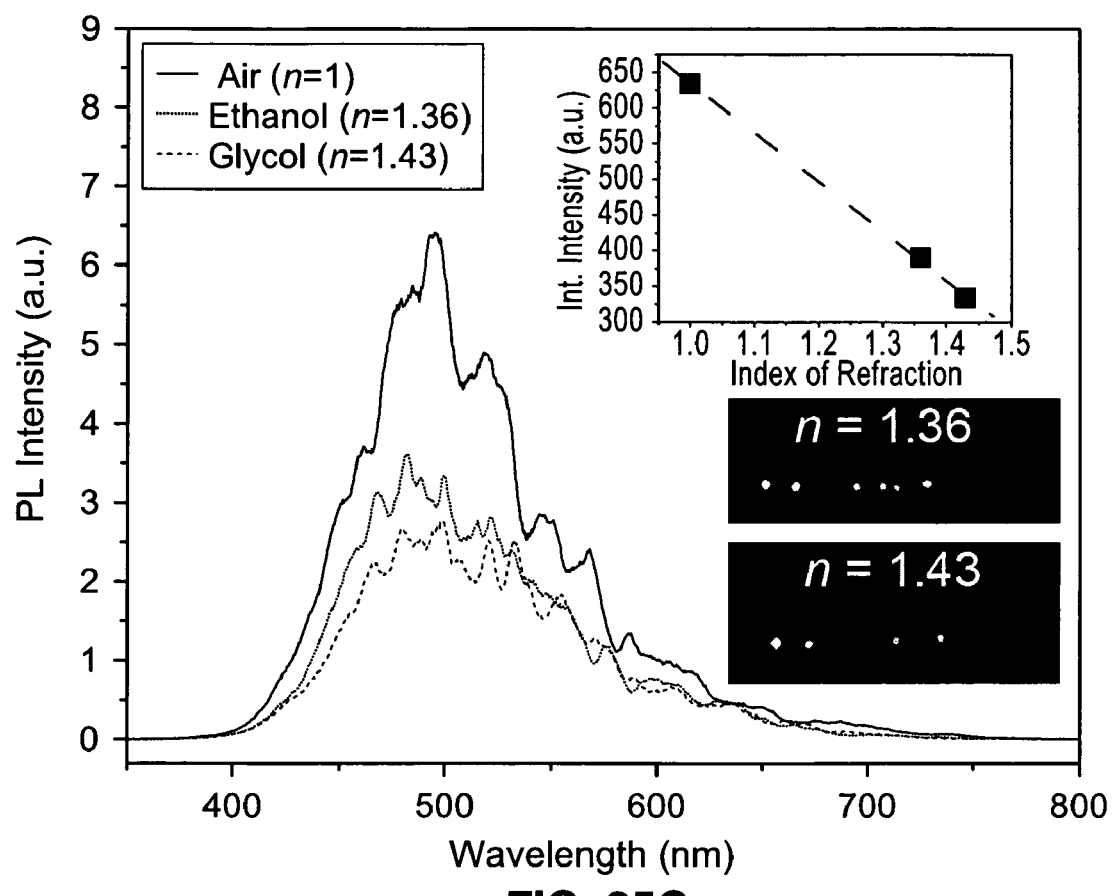

FIG. 25A-C illustrate dielectric scattering and refractive index sensing with silver nanoparticles.

Figure 26A:
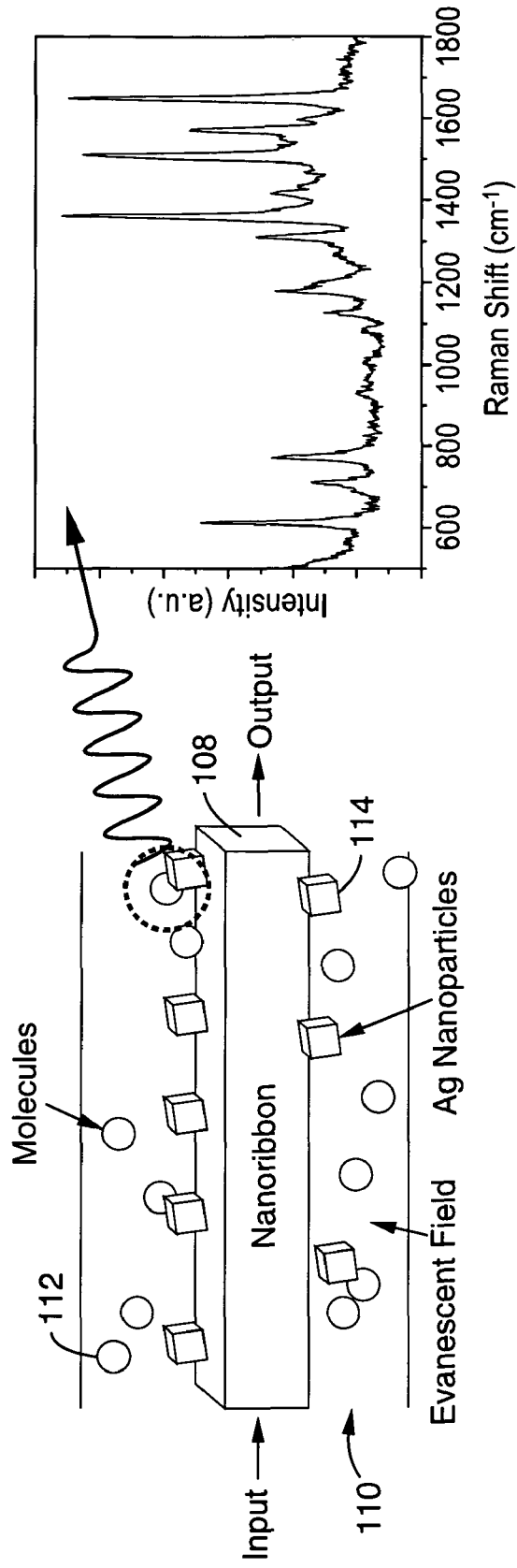
Figure 26B:
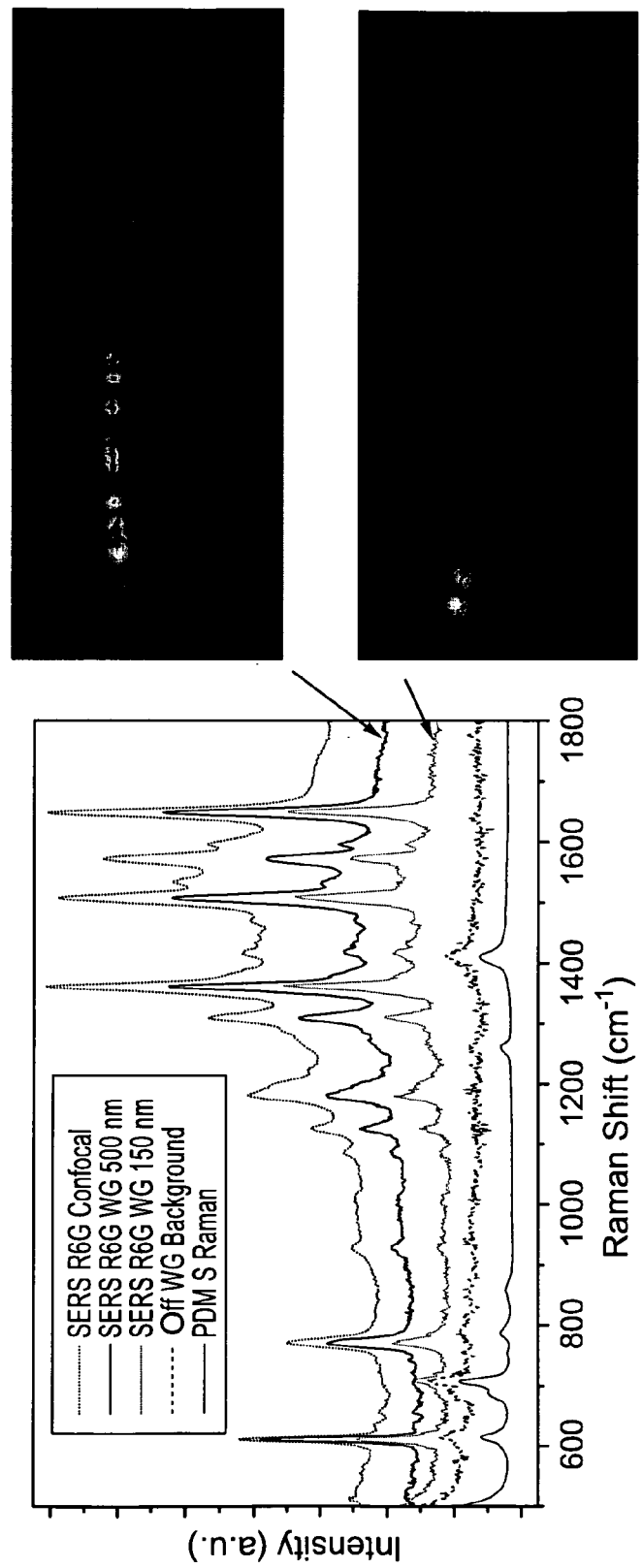
Figure 26C:
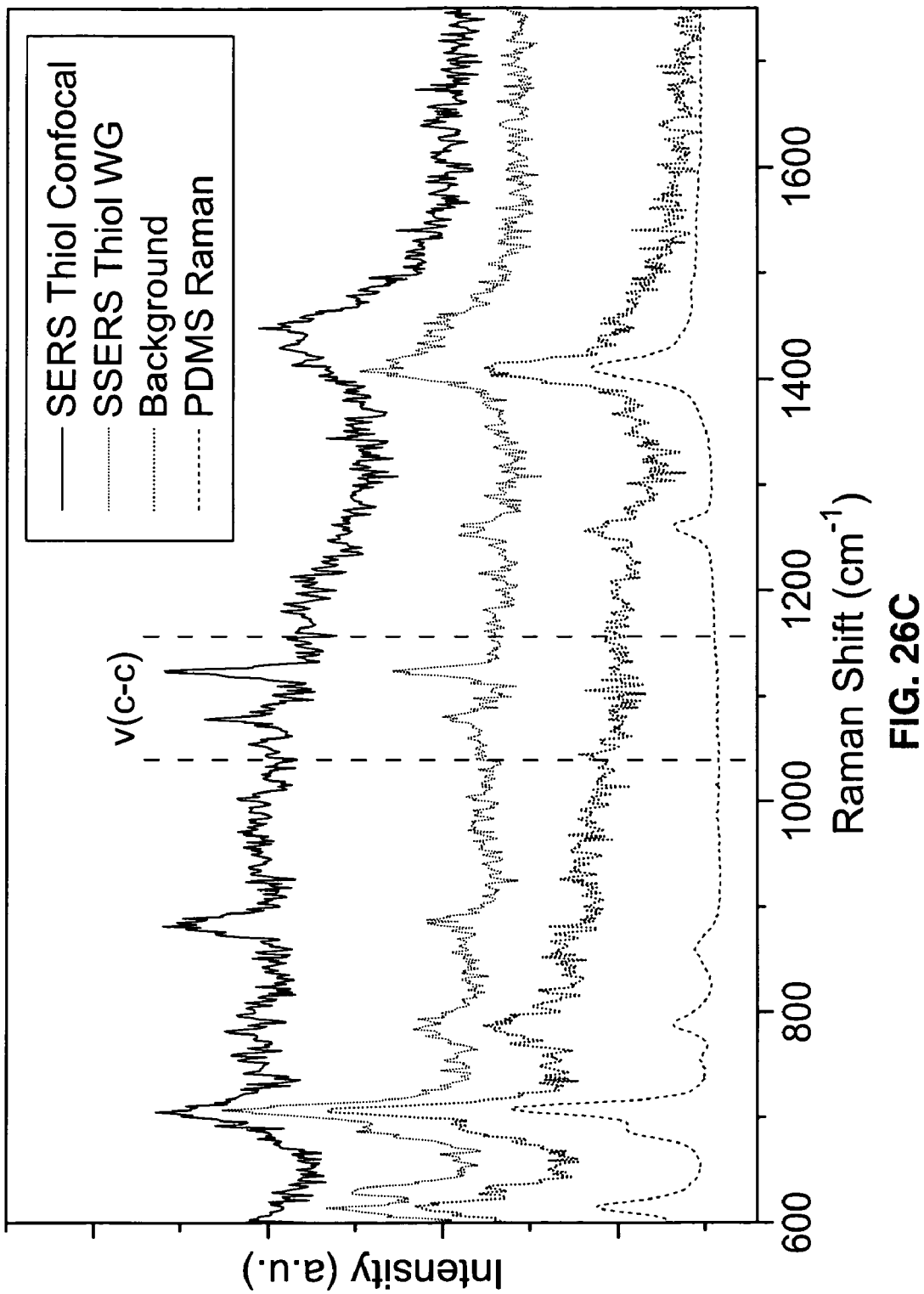

FIG. 26A-C illustrate a nanoribbon evanescent wave SERS sensor.

Figure 27A:
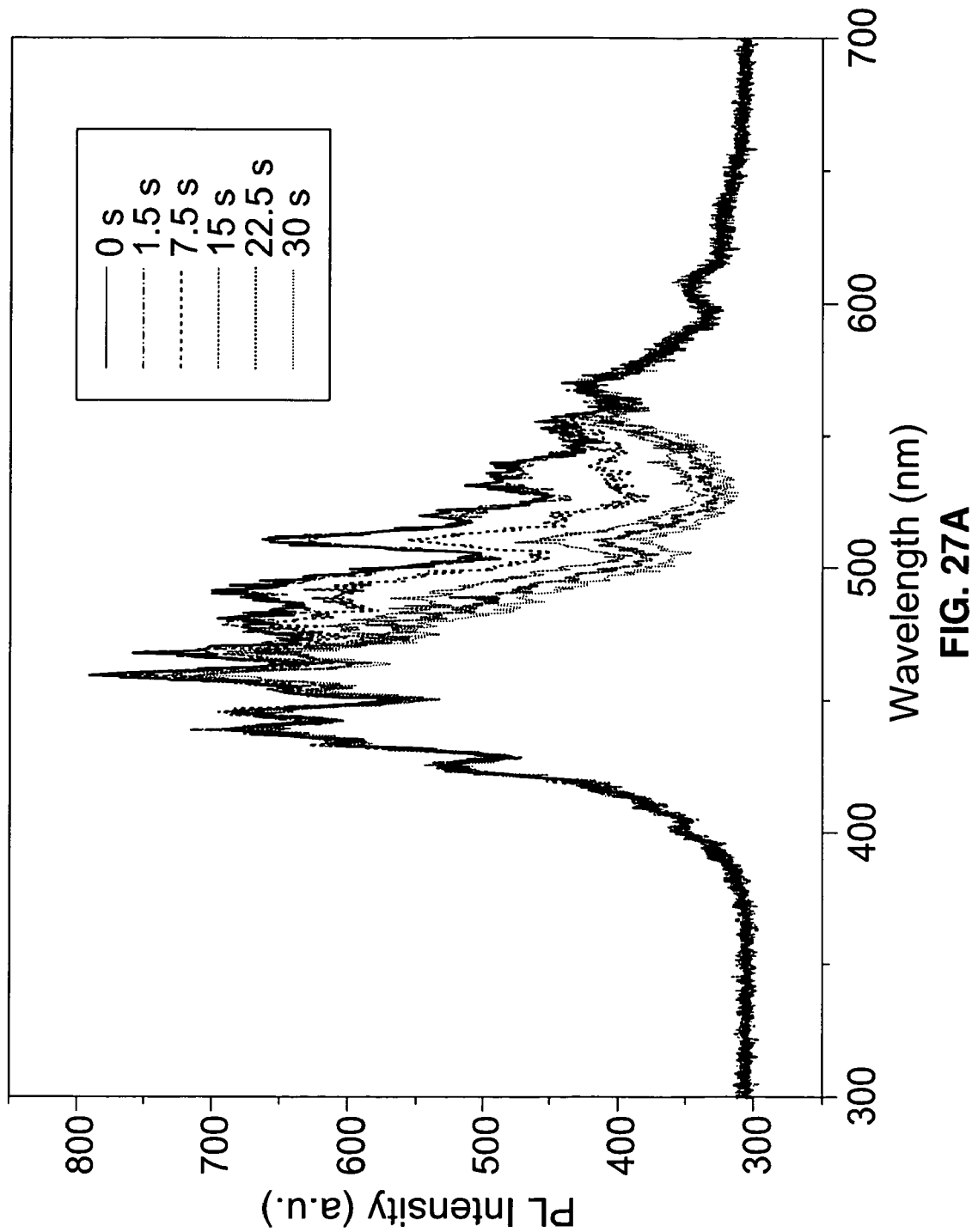
Figure 27B:
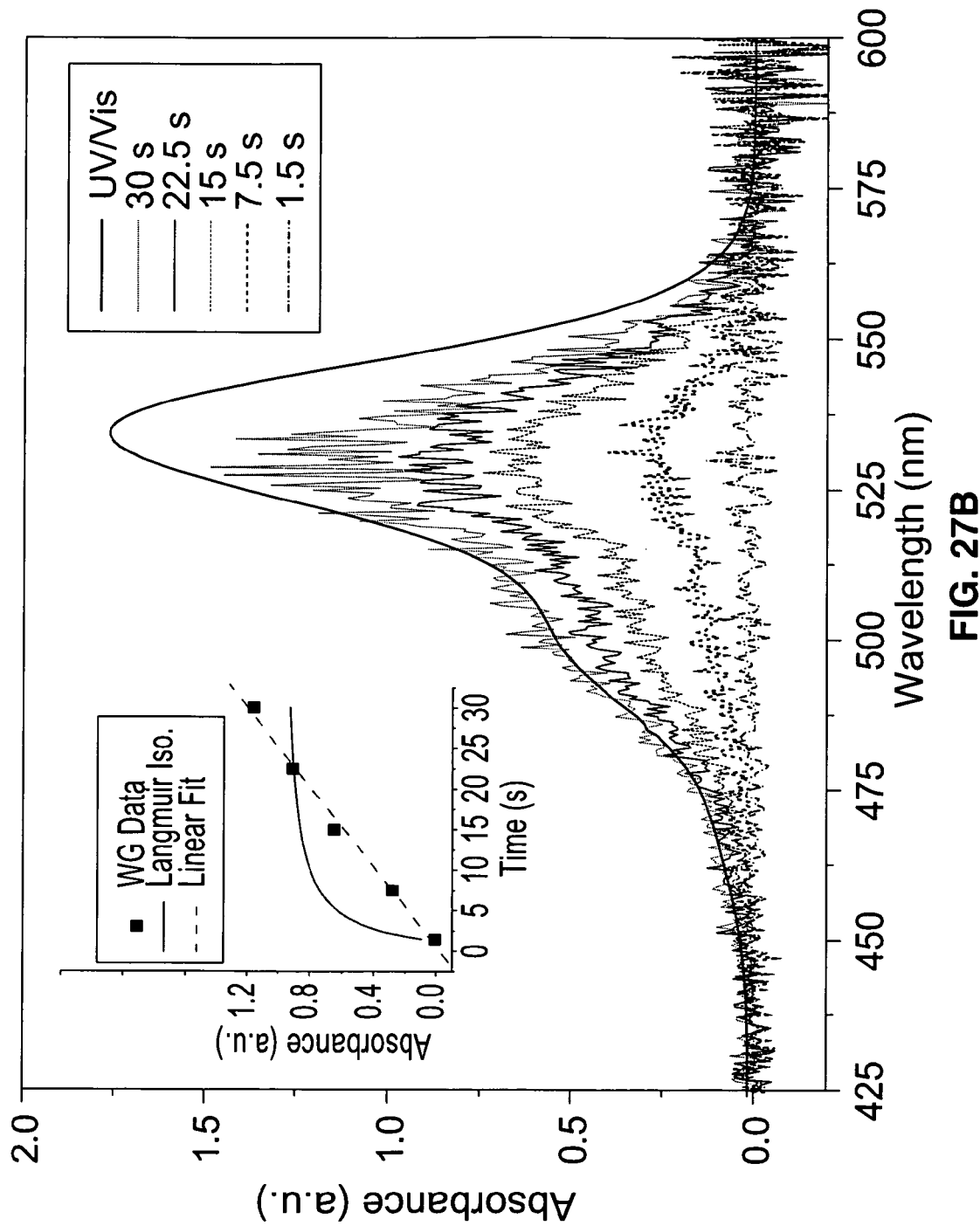

FIG. 27A-B illustrate the absorbance spectra of a positively charged dye, rhodamine 6G.

FIG. 28A-D illustrate two coupled nanoribbons for multi-pass absorption.

DETAILED DESCRIPTION OF THE INVENTION

Subwavelength Optical Waveguides

Nanoscale ribbon-shaped crystals of binary oxides exhibit a range of interesting properties including extreme mechanical flexibility, surface-mediated electrical conductivity, and lasing. However, as part of a recent study of the photoluminescence (PL) of $SnO_2$ nanoribbons in our laboratory, we discovered that nanoribbons with high aspect ratios (>1000) act as excellent waveguides of their visible PL emission. $SnO_2$ is a wide-bandgap (3.6 eV) semiconductor characterized by PL bands at 2.5 eV (green) and 2.1 eV (orange), and finds application in gas sensors and transparent electrodes. For our studies, we used conventional thermal transport techniques to synthesize single-crystalline nanoribbons of $SnO_2$ with lengths of up to 5000 μm. The structures synthesized possessed fairly uniform (+/−10%) rectangular cross-sections with dimensions as large as 2 μm×1 μm and as small as 15 nm×5 nm. Many of the nanoribbons we synthesized were 100 nm to 400 nm wide and thick, which we found to be an optimal size range for efficient steering of visible and ultraviolet light in a subwavelength cavity.

Additionally, we have found that photonic circuit elements can be assembled from, for example, $SnO_2$ nanoribbon and ZnO nanowire waveguides. High aspect ratio nanoribbons/wires with diameters below the wavelength of light (typically 100 nm to 400 nm) were found not only to act as excellent waveguides of both their own internally generated photoluminescence (PL), but also nonresonant UV/visible light emitted from adjacent, evanescently coupled, nanowires or external laser diodes. Furthermore, the length, flexibility and strength of these single-crystalline structures enable them to be manipulated and positioned on surfaces to create various single-ribbon shapes and multi-ribbon optical networks, including ring-shaped directional couplers and nanowire emitter-waveguide-detector junctions. This ability to manipulate the shape of active and passive nanowire cavities provides a new tool for investigating the cavity dynamics of subwavelength structures. Moreover, future advances in assembling the diverse set of existing nanowire building blocks could lead to a novel and versatile photonic circuitry.

Note that the use nanoribbons/wires as optical waveguides is based on the nanoribbons/wires having diameters which are smaller than the wavelength of light. Note also that nanoribbons/wires may not have circular cross-sections. For example, ZnO nanowires typically have a hexagonal cross-section and $SnO_2$ nanoribbons typically have a rectangular cross-section. Therefore, in the case of a non-circular cross-section, the term "diameter" is intended generally to refer to the effective diameter, as defined by the average of the major and minor axis of the cross-section of the structure. However, the term "diameter" is not limited to the foregoing definition and is also intended to encompass dimensions of a nanoribbon/wire which allow for the nanoribbon/wire to function as a subwavelength waveguide.

Nanoribbon Waveguides

Figure 1C:
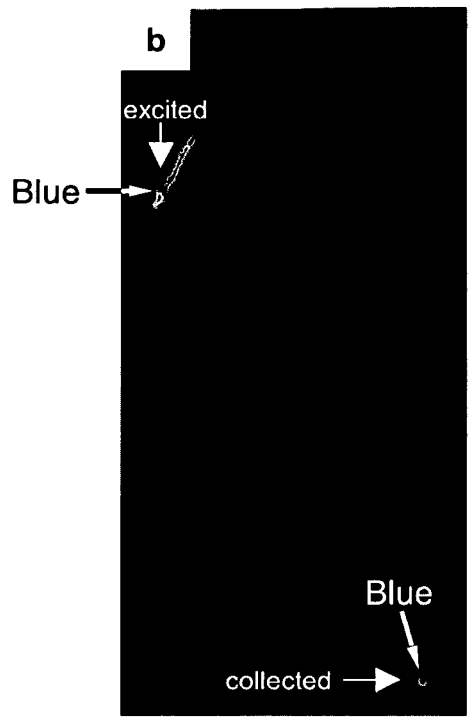
Figure 1C:
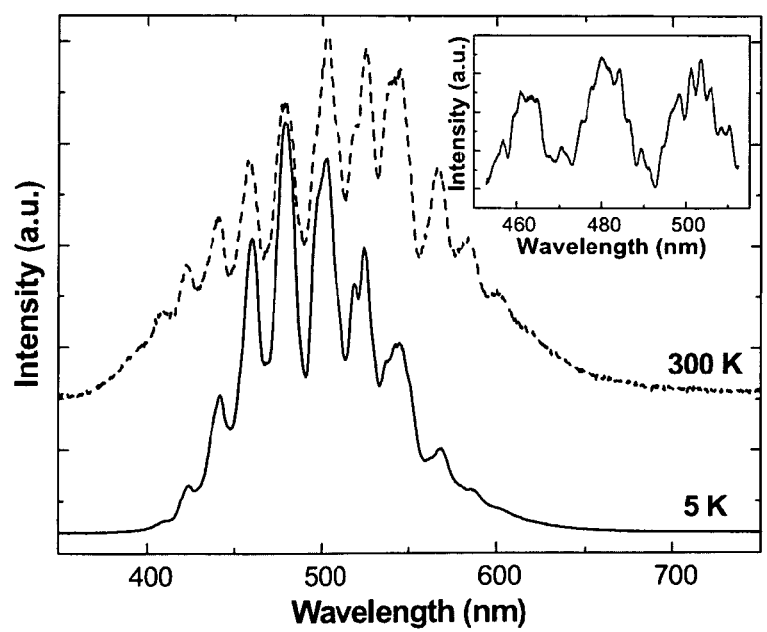

Initially, we studied the waveguiding behavior of individual nanoribbons dispersed on $SiO_2$ and mica substrates using far-field microscopy and spectroscopy. FIG. 1 and FIG. 2 illustrate representative data collected from single nanoribbons with lengths of 715 and 425 µm, respectively.

More particularly, FIG. 1 illustrates optical waveguiding in a 715 µm long $SnO_2$ nanoribbon that we synthesized. FIG. 1A is a dark-field image of a (350 nm wide by 245 nm thick) meandering nanoribbon 10 and its surroundings. The scale bar shown is 50 µm. FIG. 1B is the PL image of the nanoribbon under laser excitation. Here, the laser was focused to a spot size of ~50 µm at a 30° incidence angle at the top end of the nanoribbon. FIG. 1C shows the spectra of the emission from the bottom terminus of the waveguide, collected at room temperature and at 5 K. A higher resolution emission profile (inset) shows fine structure in three of the central peaks. This fine structure was found to be present in every peak.

FIG. 2 illustrates panchromatic waveguiding in a 425 µm long nanoribbon. FIG. 2A is a dark-field image of the nanoribbon 12, which has cross-sectional dimensions of 520 nm×275 nm. The scale bar is 50 µm. FIG. 2B is a PL image with the UV excitation spot centered near the middle of the nanoribbon, showing waveguided emission from both ends. FIG. 2C is a magnified dark-field PL view of the right end of the nanoribbon, with the laser focused on the left end. A wide (~1 µm) nanoribbon 14 lies across the nanoribbon of interest. The inset in FIG. 2C is a scanning electron micrograph of the right terminus of the nanoribbon, showing its rectangular cross-section. The scale bar is 500 nm. FIG. 2D, FIG. 2E and FIG. 2F are digital images of the guided emission 16a, 16b, 16c, respectively, at the output end of the nanoribbon during nonresonant excitation of the input end of the nanoribbon with monochromatic light of wavelengths 652 nm (red), 532 nm (green) and 442 nm (blue) light, respectively. The leftmost emission spots 18a, 18b, 18c in FIG. 2D, FIG. 2E and FIG. 2F, respectively, were caused by scattering at the nanoribbon-nanoribbon junction and were quenched by selectively removing the wide nanoribbon 14 with a micromanipulator.

Figure 2A:
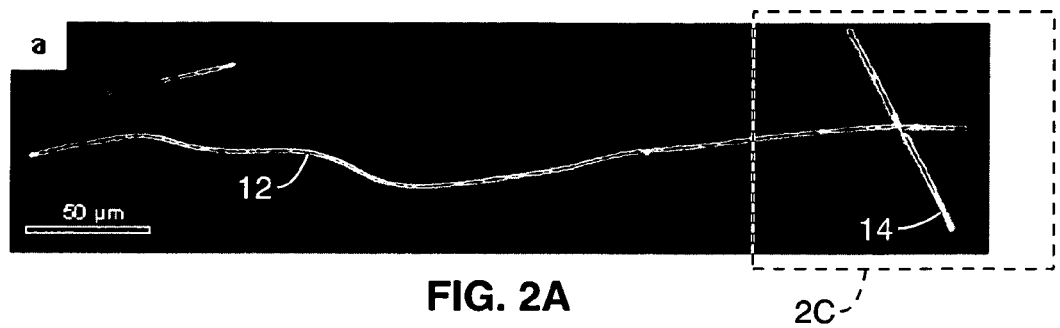
Figure 2B:
Figure 2C:
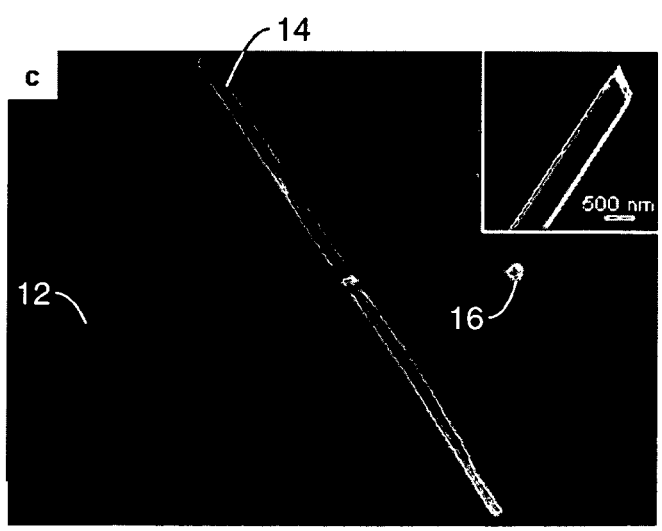

As can be seen, when we tightly focused continuous wave laser light (3.8 eV) onto one end of a nanoribbon, a large fraction of the resulting PL was guided by the nanoribbon cavity to its opposite end, where the PL emanated with high intensity. Quite surprisingly, we found that the nanoribbon mimicked a conventional optical fiber. We also found that nanoribbons that were damaged internally during dispersion or which possessed sizeable 3D surface defects scattered guided light in a series of bright spots along their lengths. Referring to FIG. 2C, contact points between nanoribbons were often dark, although overlying nanoribbons, if thick, sometimes acted as scattering centers.

Referring again to FIG. 1C, we also found that emission spectrum collected from the end of a nanoribbon while exciting its opposite end often featured complex, quasi-periodic modulation. This is due to the transverse modes allowed in a planar waveguide resulting from interference of electromagnetic waves resonating within the rectangular cavity (i.e., an optical mode structure). We found this modulation typically to be confined to the green PL component in cases of simultaneous green and orange emission, which suggests a difference in either the spatial location of PL emission (i.e., bulk vs. surface) or confinement of the two colors in the nanoribbon cavities. In short nanowire waveguides, such modulation is due to longitudinal Fabry-Perot type modes, with a mode spacing $\Delta\lambda$ given by $\Delta\lambda=\lambda^2/\{2L[n-\lambda(dn/d\lambda)]\}$, where $\lambda$ is the wavelength, L is the cavity length, and n is the index of refraction (2.1 for $SnO_2$). The nanoribbons, however, were so long that $\Delta\lambda$ was below the 0.01 nm resolution limit of our instrumentation. In addition, $SnO_2$ cavities are unlikely to show longitudinal modes since the reflectivity of their end facets is low ($\leqq$13%) and there is no gain to compensate for scattering and output-coupling losses. A systematic study of the spectral structure is complicated by the complex dependence of the modes on nanoribbon cross-sectional size and orientation (through bend losses, substrate coupling and variations in refractive index), as well as on light intensity and end facet roughness. We note that the existence of a mode structure indicates that nanoribbon cavities can have high finesse. In addition, as discussed below, the loss at given wavelengths can be modified by distorting the cavity shape.

Figure 2D:
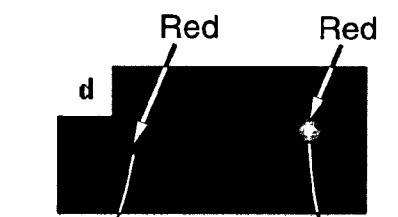
Figure 2E:
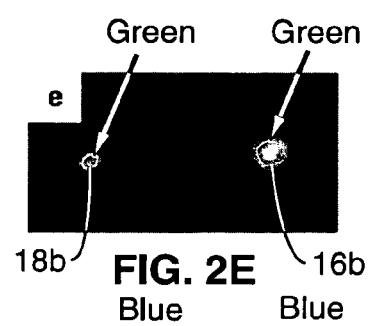
Figure 2F:
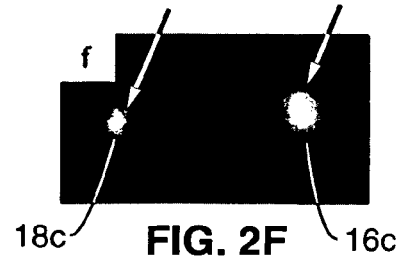

In general, one would expect a subwavelength resonator to show a large optical loss that is highly wavelength dependent, with better confinement of shorter wavelength radiation. To investigate the dependence of optical confinement on wavelength, we illuminated single nanoribbons with monochromatic red, green and blue light at a 30° incidence angle and monitored their end emission. We found that red waveguiding was rare, green waveguiding was common, and blue waveguiding was ubiquitous. We also found that, for a given dielectric material, cavity geometry and wavelength, there exists a critical diameter below which all higher order optical modes are cut off and waveguiding becomes increasingly difficult to sustain. More specifically, by treating a nanoribbon waveguide as a cylinder of $SnO_2$ embedded in air, we found cutoff diameters for higher order transverse modes of about 270 nm, 220 nm and 180 nm for the 652 nm, 532 nm and 442 nm light used in our experiment, respectively. While this approximation simplifies the cavity shape and ignores substrate coupling and other effects, these values are in reasonable agreement with scanning electron microscopy measurements of the sizes of the blue and green waveguides. Most of the nanoribbons in our samples were too thin to propagate red light over distances greater than approximately 100 µm. However, we clearly found that nanoribbons with sufficiently large cross-sectional dimensions as described above would effectively guide wavelengths across the visible spectrum, acting as subwavelength red-green-blue (RGB) optical fibers (e.g., optical transmitters) as shown in FIG. 2D through FIG. 2F.

Wavelength-Dependent Loss

We quantified the wavelength-dependent loss of straight nanoribbons using near-field scanning optical microscopy (NSOM). To do so, nanoribbons were pumped (3.8 eV) at different points along their length relative to a fixed collection probe. We found that losses ranged from 1-8 dB mm$^{-1}$ for wavelengths between 450 nm and 550 nm, depending on nanoribbon cross-sectional area and the density of surface scattering centers. These values are higher than those reported recently for subwavelength silica waveguides, likely due to the relatively rougher nanoribbon surfaces and the extra loss due to substrate coupling. We note, however, that the losses here are better than what is required for integrated planar photonic applications, in which waveguide elements would transmit light over very short distances.

Shape Manipulation

We also found the nanoribbons to be of sufficient length and strength to be pushed, bent and shaped using a commercial micromanipulator under an optical microscope. The large aspect ratio and elastic flexibility of $SnO_2$ nanoribbons allowed us to manipulate the location and shape of individual nanoribbons under the optical microscope using a commercial micromanipulator tipped with sharp tungsten probes. Waveguiding nanoribbons with one end dangling in air could be elastically bent to large angles (e.g., up to about 180°) without kinking or fracturing, which is remarkable for an oxide that is brittle in its bulk form. We were able to fashion straight nanoribbons into wiggles, circles and other shapes by using nanoribbon-substrate forces to prevent elastic recoil.

The dragging, aligning and cutting of single nanoribbons is routine. Here, we used the micromanipulator to selectively remove the overlying nanoribbon in FIG. 2C and quench scattering from that nanoribbon-nanoribbon interface. We later diced the long nanoribbon into three equal segments, creating three excellent waveguides.

FIG. 3 through FIG. 5 illustrate experimental results of our shape manipulation of nanoribbon waveguides. If these crystalline nanoribbon waveguides are to be useful as interconnects in optical circuits, they need to be capable of coupling light from one nano-object to another and to be facilely transportable from one location to another. To realize the latter, we attempted to bend and move the nanoribbons using the micromanipulator.

Figure 3A:
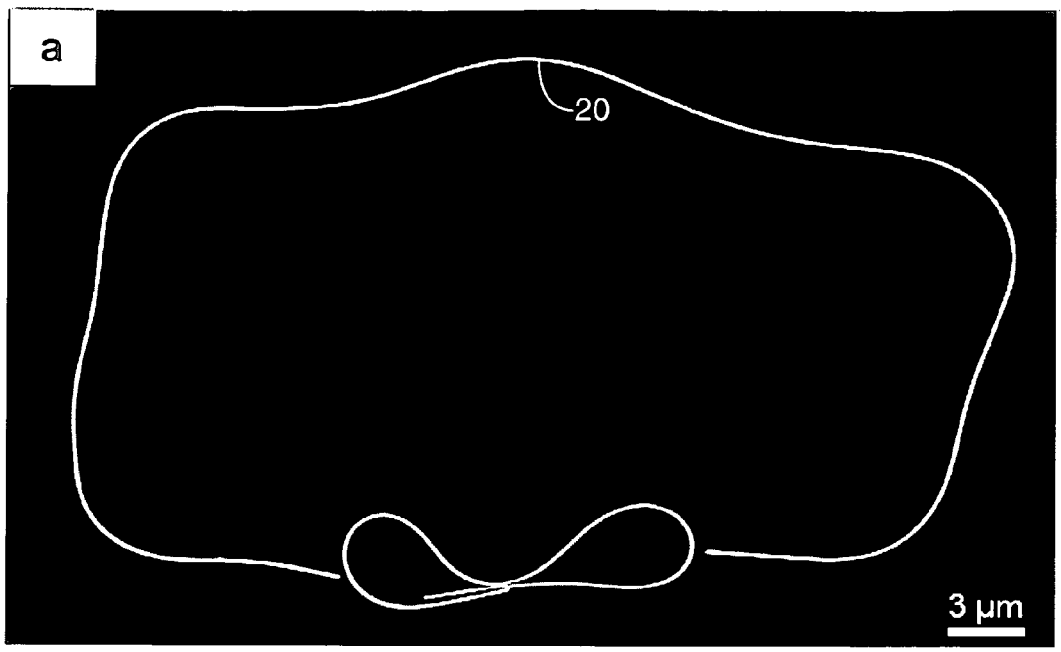
Figure 3B:
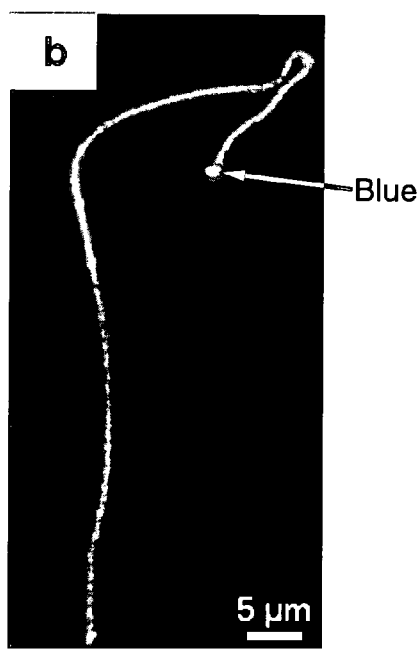
Figure 3C:
Figure 3D:
Figure 3E:
Figure 3F:
Figure 3G:
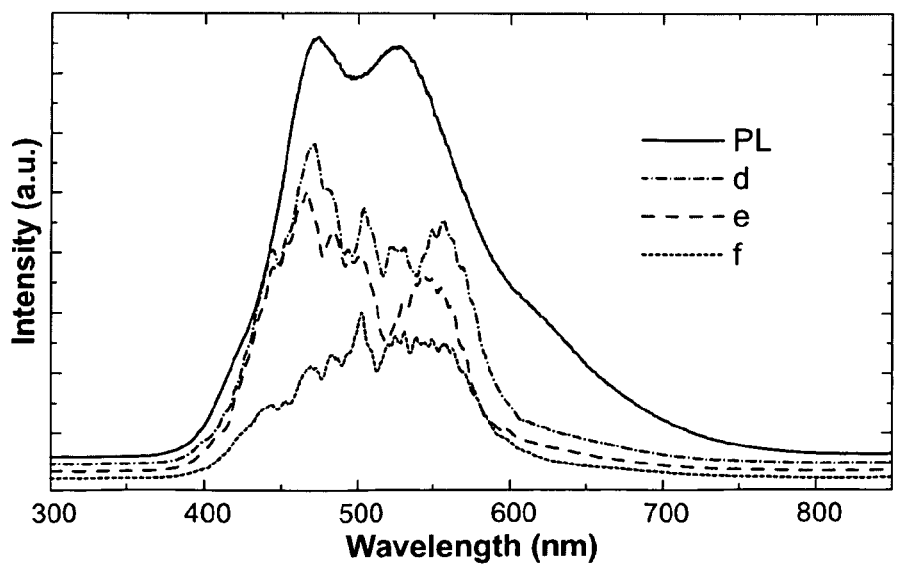

FIG. 3A is an SEM image of a simple shape 20, demonstrating the high level of positional control afforded by the micromanipulator. This shape was created from a single straight nanoribbon of dimensions 400 nm×115 nm that was cut into two pieces and then assembled. FIG. 3B and FIG. 3C are optical images of the emission end of a long nanoribbon (aspect ratio ~5200), showing the minimal effect of curvature on waveguiding. FIG. 3B is a black and white rendering of a true color photograph taken after crafting a single bend. FIG. 3C is a black-and-white dark-field/PL image captured after an S-turn was completed. We found that blue light could be guided around 1 μm radii curves with low loss. The SEM image in the inset of FIG. 3C resolves the bent geometry. FIG. 3D through FIG. 3F are a series of dark-field images and FIG. 3G is the corresponding guided PL spectra for a single nanoribbon 22 bent into different shapes. Collection was at the right end of the nanoribbon in each case. An unguided PL spectrum of the nanoribbon is included for reference. Spectra are normalized and offset for clarity.

It will be appreciated that freestanding nanoribbons can be repeatedly and elastically curved into loops with radii as small as 5 μm, which is remarkable for a crystal that is brittle in its bulk form. On appropriately chosen surfaces, single nanoribbons are easily fashioned into a variety of shapes with the help of nanoribbon-substrate forces to prevent elastic recoil as shown in FIG. 3A. Careful manipulation is normally nondestructive to the nanoribbon cavities. In practice, this manipulation method is applicable to nanostructures that are free to move and visible using dark-field microscopy, including, at the lower size limit, short nanowires (e.g., 40 nm×3 μm) and even large nanocrystals. Though an inherently slow serial process, it is faster and more versatile than similar approaches using, for instance, scanning probes or in situ scanning electron microscopy manipulation. We can create networks of nanoribbon waveguides and build functioning optoelectronic devices by assembling individual nanowire elements one at a time.

Manipulation also makes it possible to investigate the shape-dependent waveguiding of single nanoribbon cavities. For example, we fashioned a tight S-turn in one end of a long, thin nanoribbon (dimensions: 785 μm×275 nm×150 nm) to illustrate the robust nature of optical steering in these structures as shown in FIG. 3B and FIG. 3C. Losses around the bends were small and did not noticeably reduce light output from the end of the nanoribbon. In general, we found that twists and bends with radii of curvature as small as 1 μm do not disrupt the ability of these subwavelength waveguides to channel light across hundreds of microns.

We also observed that bending a nanoribbon, even slightly, can dramatically change the mode structure of its output light as shown in FIG. 3D through FIG. 3G. This is most likely because a change in cavity curvature and/or cavity-substrate coupling alters the interference pattern of propagating waves, resulting in the enhancement of some modes and the partial quenching of others. Our data also indicate that the emission pattern from a typical nanoribbon is spatially heterogeneous, as shown previously in ZnO nanowires. As a consequence, the far-field spectrum changes somewhat with collection angle, though not enough to account for the complex modal variations seen in response to distortions of the cavity shape.

FIG. 4 shows an approximately 600 μm long nanoribbon 24 slightly suspended above the substrate, which undergoes physical manipulation by an etched tungsten probe. FIG. 4A, FIG. 4C, FIG. 4D and FIG. 4F are dark-field images during the bending process, from no bend (FIG. 4A) to a >90° angle (FIG. 4F), illustrating the extreme flexibility of the nanoribbons. FIG. 4B, FIG. 4E and FIG. 4G are PL images taken at different bend angles. The excitation source was focused on the top terminus of the nanoribbon and light was guided through the bends to emerge at the bottom terminus. FIG. 4H illustrates spectra taken at the bottom terminus as a function of arbitrary bend angle. The curves identified as Bend 1, 2, and 3 in FIG. 4H correspond to the images in FIG. 4C, FIG. 4D and FIG. 4F, respectively. The mode structure was found to be significantly dependent on the size and shape of the cavity.

Figure 4A:
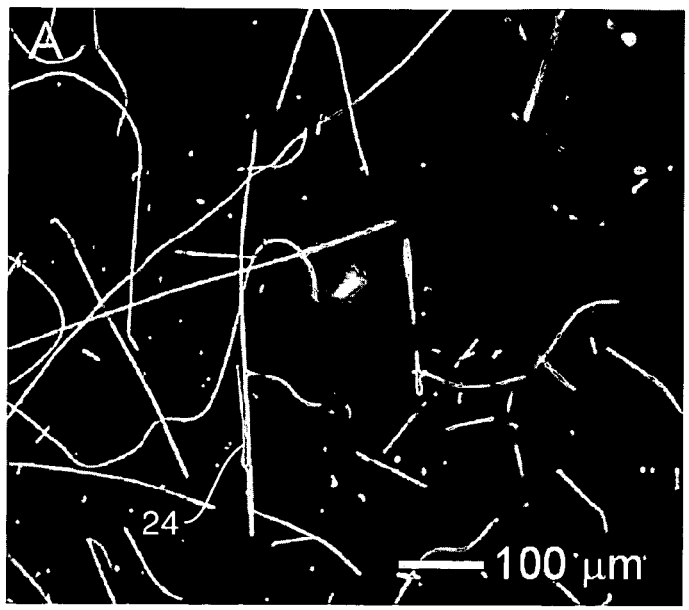
Figure 4B:
Figure 4C:
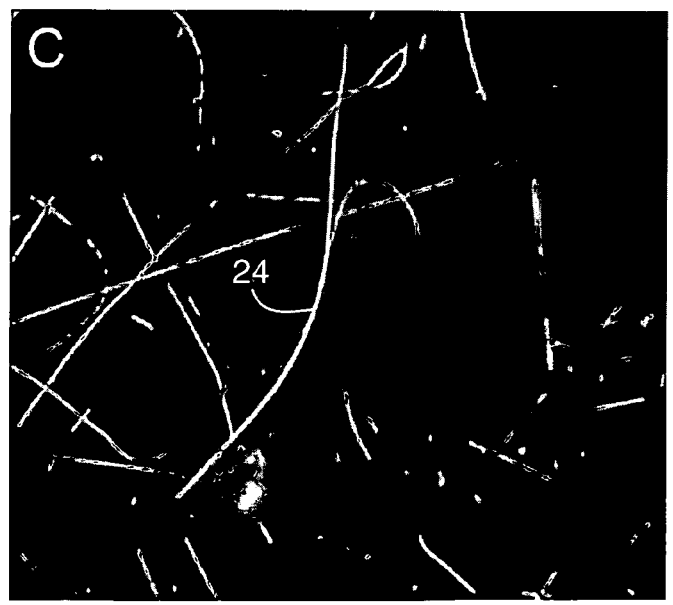
Figure 4D:
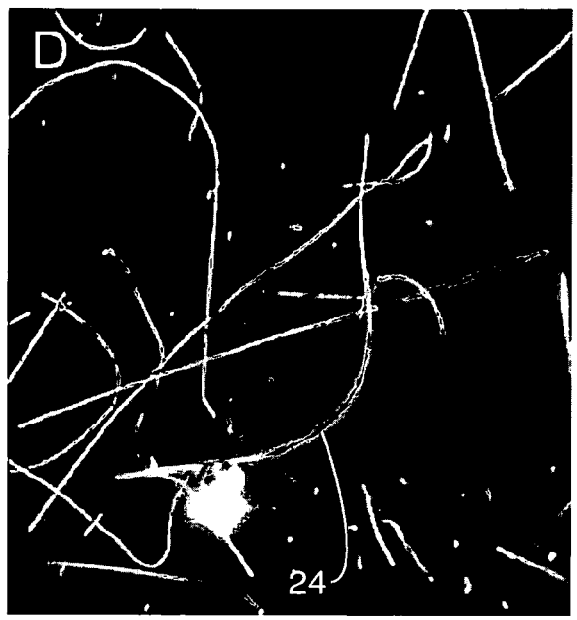
Figure 4E:
Figure 4F:
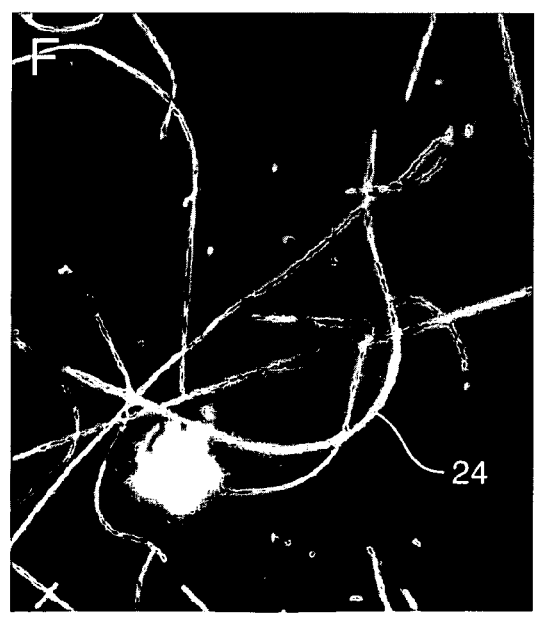
Figure 4G:
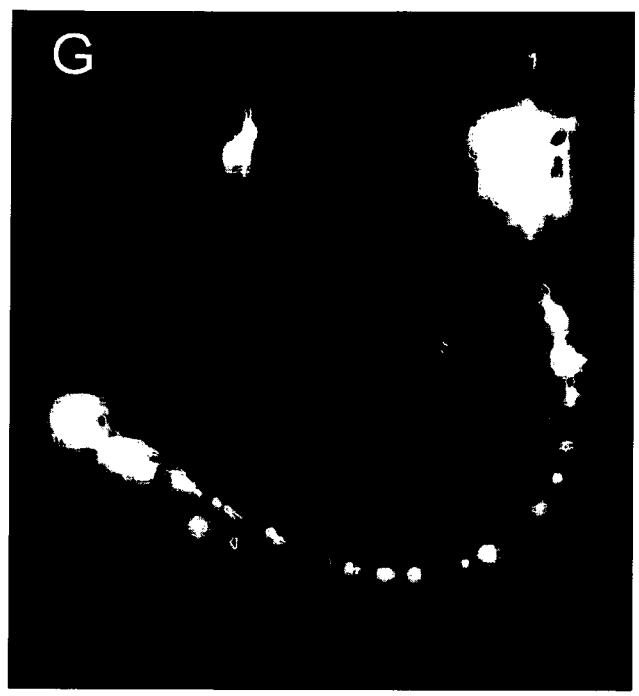
Figure 4H:
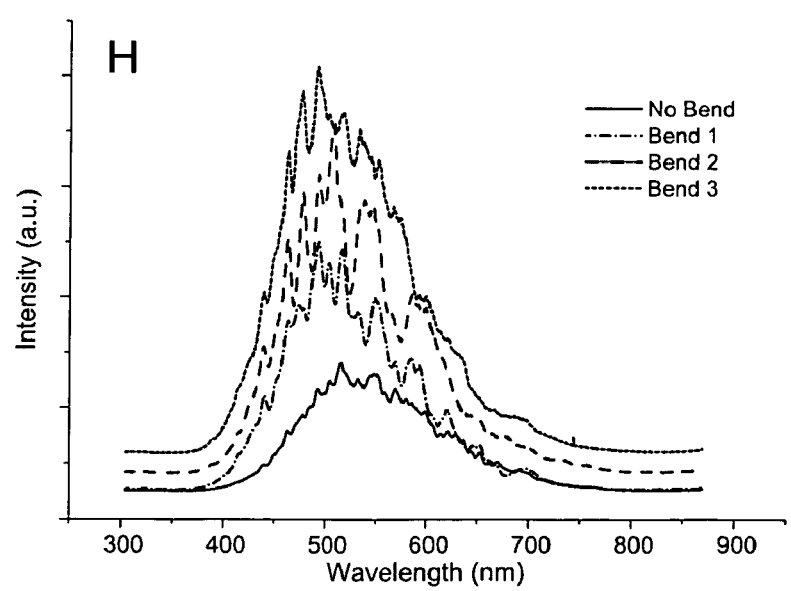

The dark field images (FIG. 4A, FIG. 4C, FIG. 4D and FIG. 4F) were taken during the process of bending a nanoribbon that was slightly suspended above the substrate. This was the first direct indication of the degree of flexibility of these oxide nanostructures. The corresponding PL images (FIG. 4B, FIG. 4E, and FIG. 4G) provide additional information on the waveguiding behavior of the cavity as the nanoribbon is bent to angles >90°. In addition to the optical images, spectra were taken from the waveguided terminus of the nanoribbon. FIG. 4H shows the resulting emission profiles as a function of arbitrary bend angle. It is apparent that the mode structure emerges as the semi-linear nanoribbon begins to take physical shape, and leads to the possibility of using these nanoribbons as high quality (Q) factor cavities. To further pursue and explore the limitations of physically perturbing these nanoribbons, we focused on thinner nanoribbons that still exhibited outstanding waveguiding properties.

FIG. 5 clearly demonstrates the potential of these structures in nano-photonic circuits. FIG. 5A and FIG. 5C are dark-field images taken before (FIG. 5A) and after (FIG. 5C) manipulating the cavity shape of a nanoribbon 26. The flexibility of the nanoribbon allows it to maintain its shape integrity even after the tungsten probe is removed. FIG. 5B and FIG. 5D are PL images of the shapes in FIG. 5A and FIG. 5C, respectively. Even with two sharp bends, the nanoribbon successfully guided the defect emission from the left coupling end to the right terminus with minimal loss occurring at the bend apexes. FIG. 5E and FIG. 5F are dark-field/PL (FIG. 5E) and PL (FIG. 5F) images of a new nanoribbon that had its bottom terminus pinned up against itself by the manipulator's tip. The excitation spot is just visible at the top of the PL image and the bottom terminus is denoted by the bright spot just above the tungsten probe. Even under extreme curvatures of radius, these nanoribbons were found to maintain their physical structures and waveguiding properties.

Figure 5A:
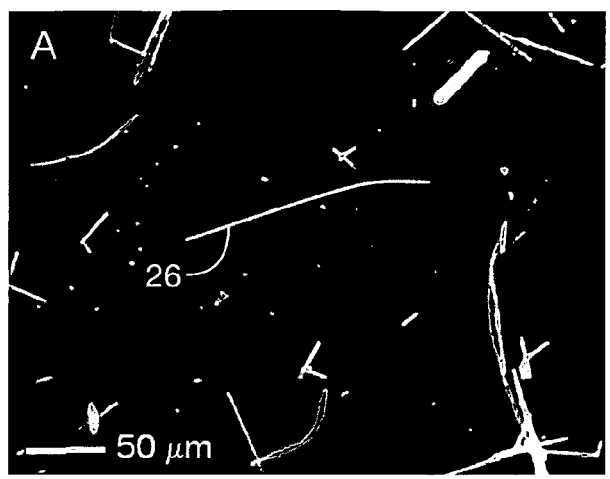
Figure 5B:
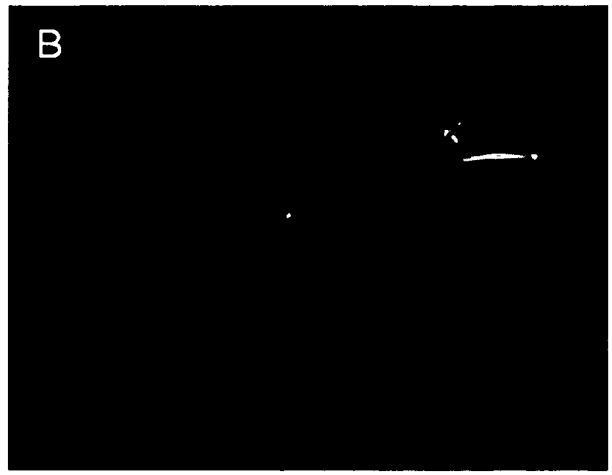
Figure 5C:
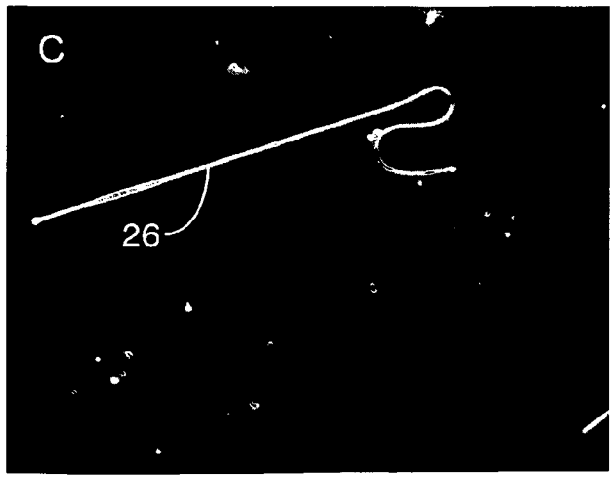
Figure 5D:
Figure 5E:
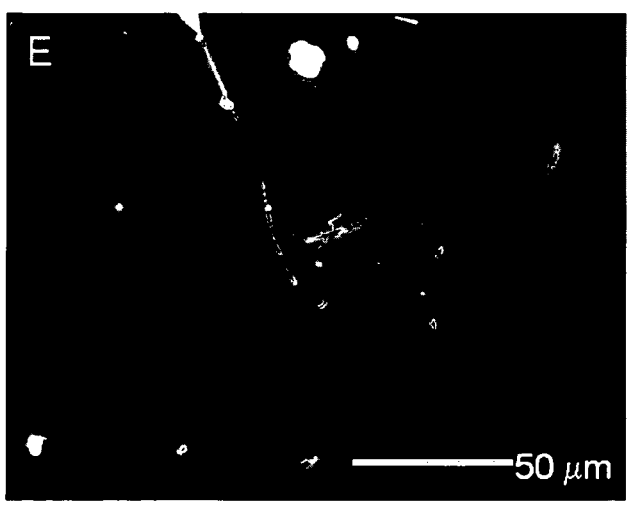
Figure 5F:
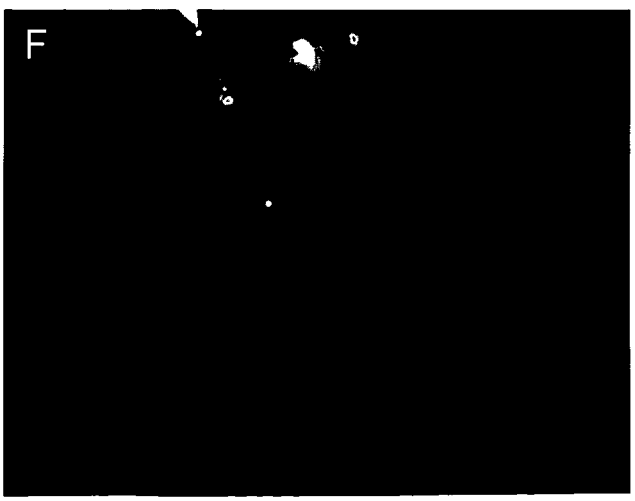

The dark-field images (FIG. 5A and FIG. 5C) and corresponding PL images (FIG. 5B and FIG. 5D) show before and after illustrations of how these nanoribbons can be torqued into sharp wiggles and curves, while still maintaining the low loss properties of the originally shaped nanoribbon. FIG. 5E and FIG. 5F reveal that this physical manipulation can be taken even further. Here, the end terminus of a new nanoribbon is actually pinned up against itself with the manipulator probe, leaving an exceptionally small radius of curvature (<5 µm) kink in the nanoribbon. Even with the tight bend and physical contact with itself, the nanoribbon did not exhibit any significant light loss due to scattering centers or cavity leakage. For conventional silica fibers, this poses a major problem. With a lower dielectric material, light confinement drastically breaks down as critical angles are surpassed. In addition, any physical contact with a material of like refractive index causes severe energy loss. Tin oxide, however, can achieve a higher internal confinement due to its higher index of refraction, nearly double that of silica (2.3 to 1.4), and its unequivocal property of minimizing loss at like-refractive index interfaces.

Nanoribbon Optical Couplers and Filters

Referring now to FIG. 6 through FIG. 9, nanoribbon waveguides can be coupled together to create optical networks that may form the basis of miniaturized photonic circuitry. The approximate size of a nanoribbon can be inferred from the color of its guided PL; namely, large nanoribbons are white, while small nanoribbons are blue. When a nanoribbon of average size is pumped nearer to one end, it shines blue at the far end and green at the near end, demonstrating the higher radiation losses for longer wavelengths. Referring also to FIG. 10, this effect makes nanoribbons excellent short-pass filters with tunable cutoffs based on path length. We have identified nanoribbon filters spanning the 465 nm to 580 nm region that feature steep cutoff edges and virtually zero transmission of blocked wavelengths.

Since light diffracts in all directions when it emerges from a subwavelength aperture, nanoribbons must be in close proximity, and preferably in direct physical contact, to enable the efficient transfer of light between them. We tested various coupling geometries and found that a staggered side-by-side arrangement, in which two nanoribbons interact over a distance of several micrometers, outperforms direct end-to-end coupling, which relies on scattering between end facets. Staggered nanoribbons separated by a thin air gap can communicate via tunneling of evanescent waves. It is also possible to bond two nanoribbons together by van der Waals forces, often simply by draping one over another, to create a robust optical junction.

FIG. 6 is illustrative of nanoribbon coupling, optical components and devices. FIG. 6A is a black-and-white dark-field/PL image of two coupled nanoribbons 28, 30 (both nanoribbons are 750 nm×250 nm, 630 µm total length). Light is incident on the right terminus of the right nanoribbon 30 and collected at the left terminus of the left nanoribbon 28. The arrow denotes the location of the junction. The SEM image in the inset of FIG. 6A resolves the junction layout. FIG. 6B illustrates raw emission spectra of the left nanoribbon 28 before (upper curve) and after (lower curve) forming the junction. The addition of the second nanoribbon and the junction lowered the output light intensity by only 50%, while its modulation was retained. FIG. 6C is a black and white rendering of a true color PL image of a three-ribbon ring structure that functions as a directional coupler. The ring nanoribbon 32 (135 µm×540 nm×175 nm) is flanked by two linear nanoribbons 34, 36 (34 at left, 120 µm×540 nm×250 nm; 36 at right, 275 µm×420 nm×235 nm). Light input at branch 1 exits preferentially at branch 3 (as shown), while light input at branch 2 exits branch 4.

Note that FIG. 6A and FIG. 6B illustrate an example of two-ribbon coupling. However, more functional geometries, such as Y-junctions, branch networks, Mach-Zehnder interferometers and ring oscillators can also be constructed. The three-ribbon ring structure illustrated in FIG. 6C operates by circulating light that is injected from one branch around a central cavity, which can be tapped by one or more output channels to act as an optical hub. With further integration, it should be possible to create optical modulators based on nanoribbon assemblies that utilize the electro-optic effect for phase shifting.

Single-crystalline nanoribbons are intriguing structures with which to manipulate light, both for fundamental studies and photonics applications. As passive elements, they are efficient UV/visible waveguides and filters that can be assembled into optical components, networks and devices. Being semiconductors or, in their doped state, transparent metals, oxide nanoribbons are well suited to combine simultaneous electron and photon transport in active nanoscale components. Key challenges to the wider use of these materials include narrowing their size dispersity and developing better parallel assembly schemes for nanowire integration. Answering the former challenge depends on gaining control over the poorly understood vapor-solid process that is typically used in nanoribbon synthesis.

FIG. 7 illustrates successful optical coupling between a ZnO nanowire 38 and a $SnO_2$ nanoribbon waveguide 40. FIG. 7A is a black and white rendering of a true color dark-field/PL image of the nanowire 38 (56 µm long, at top, pumped at 3.8 eV) channeling light into the nanoribbon 40 (265 µm long, at bottom). The arrow denotes the location of the junction. FIG. 7B is an SEM image of the nanowire/nanoribbon junction. FIG. 7C illustrates spectra of the coupled structures taken at different excitation and collection locations. From top to bottom: unguided PL of the ZnO nanowire; waveguided emission from the ZnO nanowire collected at the bottom terminus of the nanoribbon; waveguided emission from the $SnO_2$ nanoribbon excited just below the junction and collected at its bottom terminus; unguided PL of the $SnO_2$ nanoribbon. Note that the emission from the ZnO nanowire is modulated during its transit through the nanoribbon cavity.

FIG. 8 illustrates another example of a hetero-junction created between a single ZnO nanowire and a $SnO_2$ nanoribbon. FIG. 8A is a dark-field image of the junction after pushing a ZnO nanowire up to the end facet of the $SnO_2$ nanoribbon. The inset in FIG. 8A is a magnification of the active coupling region showing the short (~6-7 μm) ZnO nanowire and the upper terminus of the $SnO_2$ nanoribbon. The total length of the nanoribbon was ~600 μm. FIG. 8B shows spectra collected at the passive end (bottom terminus) while pumping either the ZnO nanowire (On ZnO) or the $SnO_2$ nanoribbon directly (On NR). A profile of the band gap emission collected over the ZnO nanowire (ZnO Only) is included for reference. The Modulation in the "On ZnO" spectrum is a direct result of the broad emission from the ZnO propagating through a high Q-factor $SnO_2$ cavity.

The 50× dark-field image and 100× dark-field inset of FIG. 8A pictorially demonstrate the basic components of an active/passive nanophotonic device. However, to ensure that we had devised a complete junction between the two nanosystems, we optically pumped the ZnO nanowire active end and collected at the passive $SnO_2$ nanoribbon end. As seen in FIG. 8B, ZnO band gap emission created from the pump source was directed across the intervening air space by the ZnO cavity and into the neighboring $SnO_2$ waveguide. The light output from the ZnO nanowire emerged at the distant end of the nanoribbon and clearly showed a modulated emission profile similar to the PL line shape seen in FIG. 4. This provides good evidence that the light was in fact waveguided across hundreds of microns by the nanoribbon cavity. To build like-material junctions, we employed a similar manipulation scheme as described above. Two waveguiding nanoribbons were coupled with their long axes collinear to each other by physically sliding a larger nanoribbon directly adjacent to the far end of a smaller nanoribbon.

FIG. 9 illustrates a $SnO_2/SnO_2$ junction created by coupling two nanoribbon waveguides 42, 44 at their end facets. FIG. 9A and FIG. 9B are dark-field images before (FIG. 9A) and after (FIG. 9B) completing a junction between a large 42 (~1 μm) and small 44 (~400 nm) diameter nanoribbon. FIG. 9C is a PL image of the same nanoribbon junction and end terminus shown in FIG. 9B demonstrating that multi-junction networks between $SnO_2$ nanoribbon waveguides can be realized.

The dark-field images in FIG. 9A and FIG. 9B capture the junction before and after successfully adjoining the two nanoribbons. The PL image in FIG. 9C verifies that light traveling down the small nanoribbon can be directly coupled into a secondary like-cavity. We are now building all-nanowire optical circuits that operate via electron injection rather than optical pumping. The oxide waveguides serve as important interconnects between active light sources, such as LEDs and lasers, and optical detectors based on photoconducting nanowires.

The optical loss of several nanoribbon waveguides was measured by systematically varying the distance between UV excitation (50 μm spot size) and PL collection in the near-field. We estimate a loss of about 2 dB mm$^{-1}$ at a wavelength of 550 nm for a nanoribbon with a 400×150 nm$^2$ cross-section, which is significantly greater than losses reported recently for subwavelength silica waveguides.

As can be seen from the forgoing, due to their extraordinary length, high flexibility and strength, nanoribbon waveguides are excellent materials with which to study the interplay between mechanics, microstructure and optical confinement in nanoscale cavities. They can be manipulated and assembled to serve as photonic interconnects between single nano-objects, such as nanowire lasers, in optical circuits and devices.

Furthermore, nanoribbon waveguides can be used as filter devices. For example, FIG. 10 illustrates the use of nanoribbons as short-pass filters. FIG. 10A shows room temperature PL spectra of five different nanoribbons, each 200 μm to 400 μm long, with 50% intensity cut-off wavelengths ranging from 465 nm to 580 nm. Cross-sectional dimensions of the 465 nm, 492 nm, 514 nm, 527 nm and 580 nm filters were 310 nm×100 nm (0.031 μm$^2$), 280 nm×120 nm (0.037 μm$^2$), 350 nm×115 nm (0.04 μm$^2$), 250 nm×225 nm (0.056 μm$^2$), and 375 nm×140 nm (0.053 μm$^2$), respectively. The spectra were normalized and offset for clarity. FIG. 10B shows a series of normalized emission spectra taken of a single nanoribbon (315 μm×355 nm×110 nm) as the pump spot was scanned away from the collection area. The unguided PL curve was obtained at a pump-probe separation of 50 μm. Larger separations resulted in a progressive loss of the long wavelengths.

EXAMPLE 1

$SnO_2$ nanoribbon waveguides were synthesized by the chemical vapor transport of SnO powder in a quartz tube reactor operating at 1100° C. and 350 Torr of flowing argon (50 sccm). Milligram quantities of nanoribbons were collected on an alumina boat near the center of the reactor and deposited onto clean substrates by dry transfer. Long ZnO nanowires were grown via oxidation of Zn metal in a quartz furnace at 800° C. and 760 Torr of flowing oxygen/argon, as described in the literature, and also dispersed by dry transfer. InP nanowires produced by a laser-assisted vapor-liquid-solid process (using Au catalyst) were sonicated into ethanol solution and transferred to the surface by drop-casting. Contacts to InP were fabricated by electron beam lithography and thermal evaporation (100 nm Ti), followed by rapid thermal annealing at 475° C. in $N_2/H_2$ for one minute.

EXAMPLE 2

Optical measurements were carried out using a dark-field microscope outfitted with a cryostat (Janis X-100). The PL excitation source was a HeCd laser operating at 325 nm. Laser pointers (532 and 652 nm) and the HeCd laser (442 nm) provided nonresonant illumination. The size of the laser spot was ~50 μm for all measurements. Spectra were collected with a fiber-coupled spectrometer (SpectraPro 300i, Roper Scientific) and liquid $N_2$ cooled CCD detector. Images were captured using both a microscope-mounted camera (CooIS-NAP, Roper Scientific) and a handheld digital camera (PRD-T20, Toshiba). Loss measurements were made with a commercial NSOM setup operating in collection mode, with 325 nm excitation. For nanoribbon manipulation, we used a three-axis commercial unit tipped with tungsten probes (10 μm ends).

As described above, photonic circuit elements can be assembled from $SnO_2$ nanoribbon and ZnO nanowire waveguides. High aspect ratio nanoribbons/wires with diameters below the wavelength of light (typically 100 nm to 400 nm) were shown to act as excellent waveguides of both their own internally generated photoluminescence (PL) and non-resonant UV/visible light emitted from adjacent, evanescently coupled, nanowires or external laser diodes. The length, flexibility and strength of these single-crystalline structures enabled them to be manipulated and positioned on surfaces to create various single-ribbon shapes and multi-ribbon optical networks, including ring-shaped directional couplers and nanowire emitter-waveguide-detector junctions. This ability to manipulate the shape of active and passive nanowire cavities provides a new tool for investigating the cavity dynamics of subwavelength structures. Moreover, future advances in assembling the diverse set of existing nanowire building blocks could lead to a novel and versatile photonic circuitry.

Waveguiding in Liquids

Quite surprisingly, we have also found that these one-dimensional (1D) nanostructures can guide light through liquid media. The fact that light can be delivered through these cavities in solution offers a unique application for high dielectric (n≧2) waveguides in fluidic sensing and probing. Waveguiding in liquids is especially important for integrated on-chip chemical analysis and biological spectroscopy in which small excitation and detection volumes are required. Subwavelength nanostructures can be assembled to probe molecules in a fluorescence or absorption scheme, both of which utilize the decaying light field outside of the cavity to induce photon absorption. The waveguide is strongly coupled to emitted photons near the cavity, allowing the generated fluorescence to be directed back to the point of injection. Also, the nanoscale dimensions of the waveguides afford small liquid volumes (~picoliters) to be sensed and presage the way for miniaturized optical spectrometers.

Here, we also build upon the initial demonstration of nanowire/ribbon photonic assembly with several proof-of-principle illustrations of optical routing between coupled nanowires. We first show that it is possible to deliver individual nanosecond light pulses from lasing GaN and ZnO nanowires through a nanoribbon waveguide; pulsed light must be transmissible if nanowire photonic devices are to be useful in communications or computing. Simple networks of $SnO_2$ nanoribbons are then used to separate white light and route individual colors based on a short-pass filtering effect. We also describe an optical crossbar grid made of two pairs of orthogonal nanoribbons that conducts light through abrupt 90° angles and provides a dramatic example of the nature of optical confinement in these subwavelength cavities. The fact that the waveguiding ability of our freestanding, flexible nanowires and nanoribbons survives in liquid media suggests a role for nanowire light delivery in microfluidics and biological applications.

Subwavelength Waveguides as Optical Probes and Sensors

High dielectric subwavelength waveguides have a considerable advantage for confining light in liquids over low dielectric waveguides such as silica-based structures. The low index contrast between the solution (cladding) and silica core ($n_{silica} \approx 1.45$) hinders efficient propagation of the light wave. FIG. 11 compares the photoluminescence (PL)/dark-field images of a $SnO_2$ nanoribbon (dimensions: 365 nm×105 nm×265 μm) resting on a silicon oxide surface (1 μm thermal oxide) waveguiding in air (n=1) and water (n=1.33). The PL is generated with a CW HeCd laser (325 nm). FIG. 11 also shows how the guided PL spectrum of this thin nanoribbon changes when it is immersed in water.

FIG. 11A is a combined PL/dark-field image of the nanoribbon 46 on a dry oxide surface. The inset shows a magnified view of the blue end emission. FIG. 11B shows the same nanoribbon in a water environment, under a quartz coverslip. The inset shows resultant green emission. FIG. 11C shows the spectra of the two situations. The large red shift of the empirical cutoff wavelength (from 483 nm in air to ~570 nm in water) is caused by the decrease in refractive index profile between the substrate and the cap medium. The more homogeneous cladding index improves wave confinement in the nanoribbon core. The effect was reversible by evaporating the water.

As can be seen from FIG. 11C, the spectra of the guided PL spectrum broadens to longer wavelengths when it is covered by pure water. Such a red shift would be anomalous for a fiber with a cladding of homogeneous refractive index, where one expects the replacement of air (n=1) by water (n=1.33) to increase losses and result in a blue shift of the mode cutoff. However, when a slab or strip waveguide exists in an asymmetric cladding environment (that is, when $n_{waveguide} > n_{subtrate} > n_{cover}$), as it does here, raising the index of the cover reduces its asymmetry with the substrate and improves confinement.

Intuitively, the replacement of air (n=1) with water (n=1.33) on three sides of a nanoribbon should increase its optical loss and hinder waveguiding, especially for longer wavelengths. One would expect a narrowing of the guided spectrum (a blue shift of the cutoff wavelength). Instead, we found that the spectrum broadens to the red and the end emission changes from blue in air to green in water. This surprising result, which seems to suggest that a smaller index profile between core and cladding results in better, not poorer, confinement, is likely a consequence of the smaller difference in refractive index between water and the $SiO_2$ substrate than between air and the substrate. The less anisotropic water-silica cladding shifts the modal power nearer to the center of the nanoribbon and thereby reduces overall radiative loss. Ribbons that were too large to show a cutoff for PL were unaffected by immersion in water.

To demonstrate controlled manipulation of small volume, substrate supported, liquid droplets, we placed an approximately 5 μL droplet of 1,5-pentanediol on a silica substrate and then used a commercial micromanipulator, equipped with an etched tungsten probe (tip diameter ~400 nm), to dice the large droplet into small volumes as shown in FIG. 12. FIG. 12A shows a dark-field image of various sized droplets of 1,5-pentanediol on a silicon substrate (with a 1 μm thermal oxide). The radii and corresponding volumes are displayed by each droplet. FIG. 12B is a magnified dark-field image of smaller droplets (<1 fL). The radii and corresponding volumes (down to ~20 fL) are labeled on the dark-field image in FIG. 12A. Even smaller volumes (<1 fL) can be achieved with this method as shown in FIG. 12B. An alternative method to producing small volumes would be to use microfluidic channels to mold the shape of the solution.

Ribbon waveguides can also sense molecules, proteins or larger biological entities in solution by means of either an emission or absorption mechanism as mentioned above. In the former, a nanoribbon provides local excitation for fluorophores passing through the cone of scattered light at its output end, and the emission is collected by a fiber or microscope.

Referring to FIG. 13, to demonstrate this fluorescence scheme, we embedded the tip of a nanoribbon 48 in an approximately 3 pL to 5 pL droplet of 1 mM Rhodamine 6G laser dye (R6G) in 1,5-pentanediol (n=1.45). FIG. 13 shows fluorescence and absorbance detection of R6G with a nanoribbon cavity. FIG. 13A is a fluorescence image of a droplet of 1 mM R6G in 1,5-pentanediol excited by blue light from a nanoribbon waveguide 48 (240 nm by 260 nm by 540 μm). The nanoribbon crosses the frame from upper left to lower right. A notch filter was used to block the excitation light. The left inset of FIG. 13A is a dark-field image showing the droplet and the bottom half of the nanoribbon. The right inset of FIG. 13A is a magnified view of the droplet emission, showing the light cone and evanescent pumping of the dye along the nanoribbon length. FIG. 13B shows the spectra taken of the droplet region (direct) and the fluorescence coupled back into the nanoribbon (guided). The red shift of the guided emission is a microcavity effect. FIG. 13C is a dark-field image of the nanoribbon with a droplet deposited near its middle (absorbance geometry). The nanoribbon was UV pumped on one side of the droplet and probed on the other side, as indicated. FIG. 13D shows the spectra of the guided PL without liquid present and with droplets of pure 1,5-pentanediol and 1 mM R6G. The arrow indicates the absorption maximum of R6G.

Figure 13A:
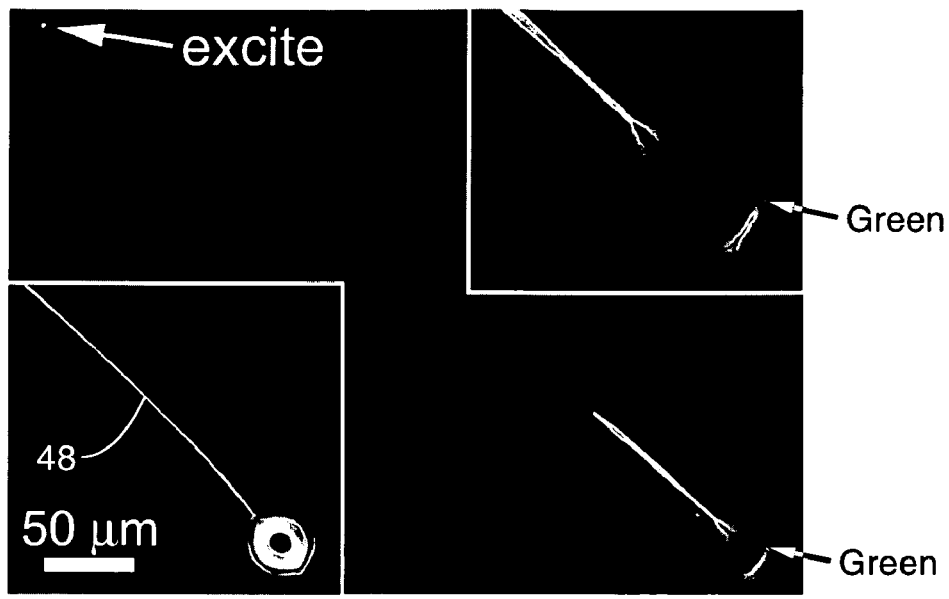
Figure 13B:
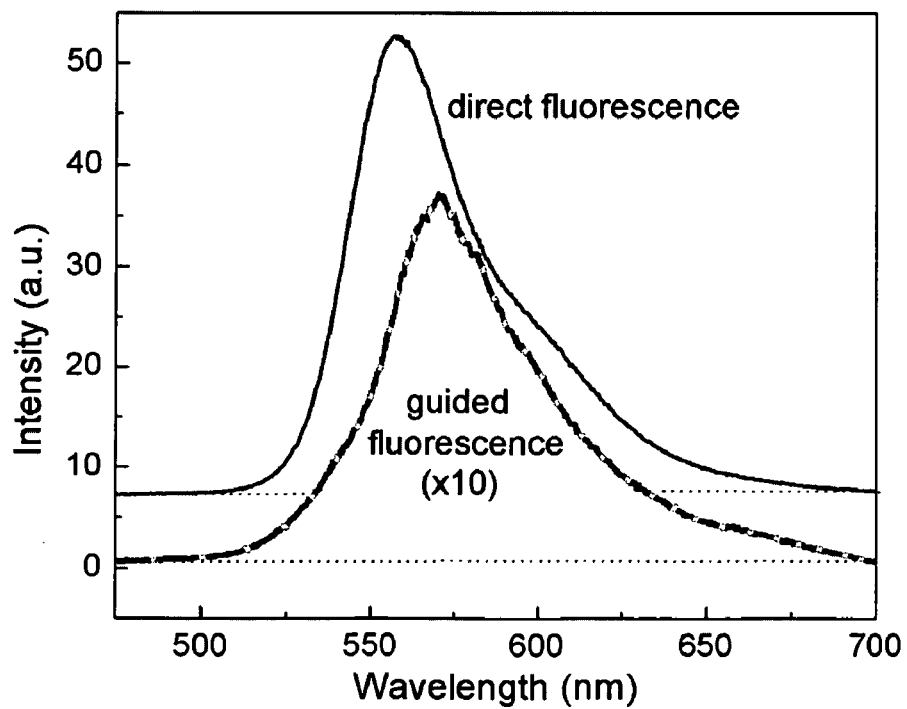

As can be seen, blue light (442 nm) launched into the far end of the nanoribbon resulted in strong fluorescence from within the droplet, where the R6G emission mapped out the spatial intensity distribution of the waveguide output as a cone of light (FIG. 13A and Inset). A fraction of this fluorescence was captured by the nanoribbon cavity and guided back to its far end, demonstrating that these waveguides are capable of routing signals both from and to liquids. Spectra acquired from both ends of the nanoribbon are shown in FIG. 13B. The guided fluorescence is red-shifted and somewhat sculpted by its passage through the nanoribbon. However, there is little trace of the heavy mode imprinting evident in, for example, FIG. 17F discussed below.

FIG. 13B also shows strong fluorescence originating from the segment of the nanoribbon wet by the droplet through capillary action. Here, dye molecules in proximity to the nanoribbon surface are excited in a subwavelength version of total internal reflection fluorescence (TIRF). In normal TIRF, excitation of a macroscopic waveguide (such as a microscope coverslip) generates an evanescent field of light that decays exponentially with distance from the waveguide surface, limiting the depth of excitation to a distance of ~100 nm and enabling the local probing of structures such as cell membranes. Because subwavelength fibers can carry a larger fraction of their modal power outside of the core, they enhance the intensity of this evanescent field and increase its penetration depth into the surroundings, making proportionally more power available to excite nearby molecules. Calculations indicate that roughly thirteen to fifteen percent of the electric field intensity exists outside of the nanoribbon for the wavelength of light used in this experiment. In this case, the radial field intensity decays to ten percent of its maximum value at the center of the waveguide by about 135 nm into the liquid solution. Since TIRF detection sensitivity scales with the fractional power present in the waveguide cladding, one-dimensional nanostructures are promising waveguides for local fluorescence sensing using this approach.

Figure 13C:
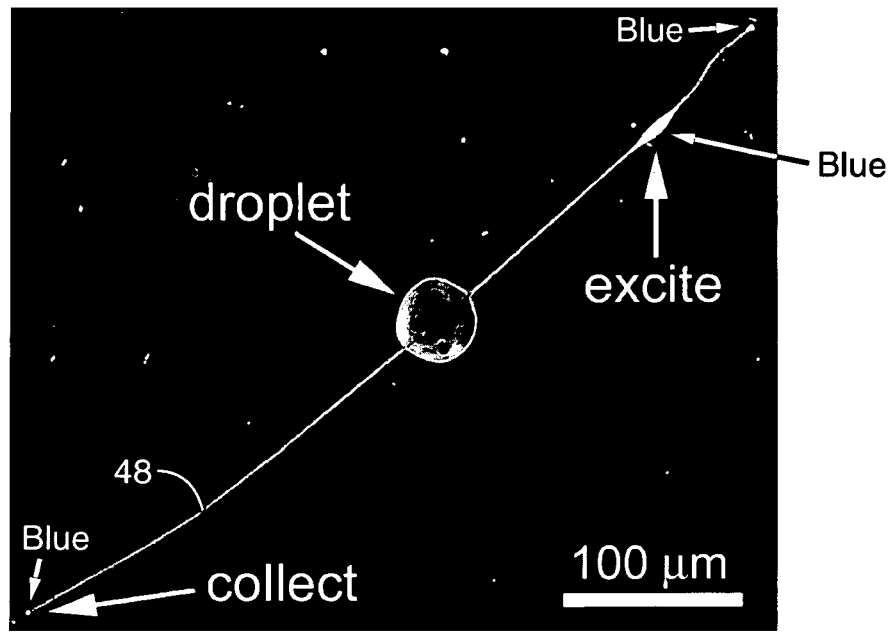
Figure 13D:
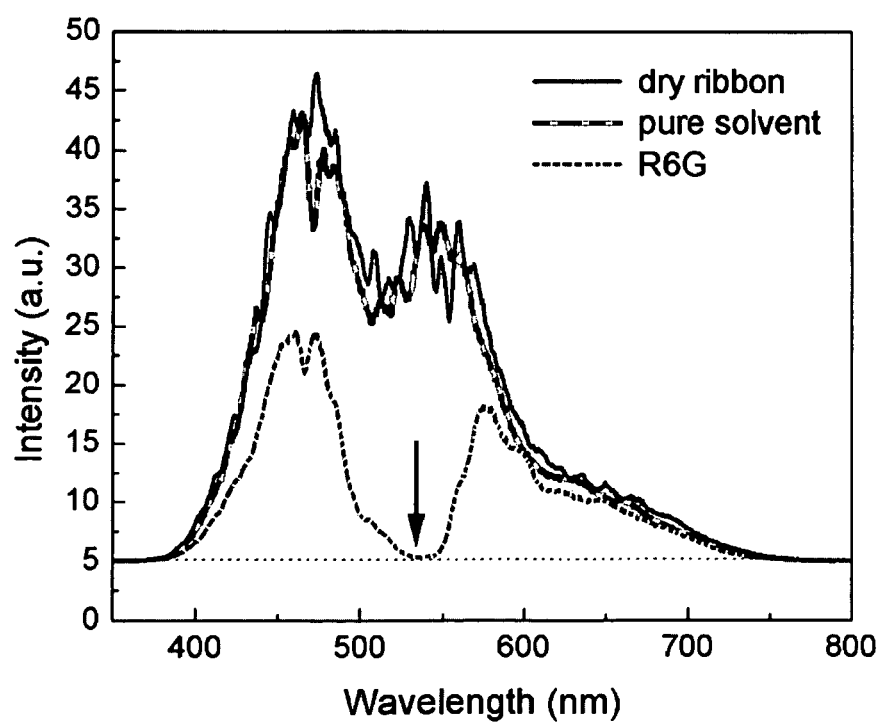

Another way that 1D nanostructures may be used for optical detection in solution relies on producing an absorption spectrum of molecules located on and near the nanoribbon surface. Absorbance detection, while inherently less sensitive than fluorescence methods, is applicable to a wider range of molecules and avoids the complications of fluorescent tagging. We launched white PL down a long nanoribbon (260 nm×240 nm×540 µm) onto the midpoint of which a ~1 pL droplet of 1 mM R6G ($\alpha_{max}$=535 nm) was deposited (FIG. 13C). Dye molecules in the droplet imprinted their absorption signature onto the propagating PL wave (double-Gaussian beam), completely quenching transmission through the nanoribbon around the R6G absorption maximum (FIG. 13D). Considering the dye concentration, droplet size and spatial extent of the evanescent field, we estimate that less than forty attomoles of dye (~24 million molecules) were probed in this experiment. We have experimentally shown that sensitivities down to 50 µM (~35,000 molecules) are easily attainable. We were able to detect dye concentrations as low as 1 µM (24,000 molecules) using the same nanoribbon and a comparable path length of ~50 µm (not shown). Since this absorbance approach also utilizes the evanescent fraction of the guided field, smaller nanoribbons should again provide greater sensitivity. Other options for improvement include altering the cavity shape to increase the probe length (as discussed below), functionalizing the nanoribbon surface for selective biosensing and launching multiple wavelengths for the simultaneous detection of analytes with different electronic transitions. The next steps are to integrate subwavelength 1D nanostructures into microfluidic devices and to apply them as flexible probes in the study of live cells.

A third way that subwavelength nanoribbons/wires can be used for chemical/biological sensing relies on the surface enhanced Raman spectroscopic (SERS) effect. Surface-enhanced Raman scattering occurs when an analyte molecule is probed in proximity to a metal surface (usually Cu, Ag or Au) that serves to massively enhance the local electromagnetic field through resonance with the surface plasmons of the metal. The resulting Raman signal of the analyte can be enhanced by a factor of up to $10^{14}$, which allows single-molecule sensing in many cases. The nanoribbons/wires described here were fashioned into subwavelength SERS fibers by decorating their surfaces with a high density of silver nanoparticles. By exposing the nanoparticles-coated nanoribbon/wire to an analyte solution while injecting monochromatic light down the nanoribbon/wire, it is possible to detect the SERS signal of the analyte molecule. This concept allows "fingerprint" identification of analyte molecules based on their SERS vibrational signatures, using a subwavelength waveguide for light introduction and confinement. FIG. 14A shows a schematic picture of this concept, while FIG. 14B and FIG. 14C show an image of a nanoribbon (NR) coated with 40 nm silver nanoparticles attached by exposing the nanoribbon to a flowing nanoparticle solution. The particles are seen to scatter the waveguided light very effectively. By then exposing the structure to an analyte solution of interest, it is possible to generate a SERS signal. The device is reusable by simply dissolving the Ag nanoparticles in an acidic solution (e.g., $HNO_3$) and then reintroducing fresh Ag particles.

The devices shown thus far all operate under single pass geometries. Multi-pass structures would increase sampling lengths and ultimately lead to a more sensitive spectrometer. FIG. 15 shows a PL/dark-field image of two nanoribbons (NR1 and NR2) evanescently coupled at arrow 1. The top inset is a magnified dark-field image of the coupled nanoribbons with a glycol droplet designating where the analyte would sit in this configuration. The bottom inset is a dark-field image of NR1 with NR2 removed showing a coupled ring structure (junction—denoted be arrow 2) that would serve as a multi-pass beam path in a subwavelength optical spectrometer.

FIG. 15 illustrates that ring shapes can be easily fashioned using our manipulation capabilities to create a subwavelength cavity shape that would sample an analyte repetitively. The glycol droplet (top inset) serves to identify where the analyte would sit in this particular configuration. The PL/dark-field image shows a two nanoribbon device evanescently coupled (arrow 1 denotes the junction), illustrating the first step to design a multi-pass spectrometer based on free-standing 1D nanostructures. The bottom inset was taken after manipulating the end of NR1 into a ring structure (arrow 2 denotes the junction) showing the second step for creating a multi-cycle instrument. Additional work is necessary to fully realize better sensitivity from these advanced designs, but previous results on coupling efficiencies suggest up to an order of magnitude increase from a multi-pass geometry.

We note that the fabrication of a practical subwavelength fiber spectrometer as introduced above would benefit from a more controlled flow-cell type microfluidic design in which the sensing nanoribbon/wire is integrated with microfluidic channels for solution introduction. We have built such an integrated device using a poly-dimethylsiloxane (PDMS) stamp patterned with flow channels to control analyte flow past an embedded nanoribbon/wire waveguide. With this microfluidic design, we can pulse multiple analyte solutions past a well-defined section of a sensing nanoribbon/wire, permitting reuse of the sensor for biological and other liquid-based monitoring uses. FIG. 16 shows the microfluidic channels (MFC) of a PDMS stamp bridged by multiple nanoribbons (NR). This is shown schematically in FIG. 16A. FIG. 16B is an image showing microfluidic channels in detail and FIG. 16C is an image showing several nanoribbons bridging the microfluidic channels shown in FIG. 16B. This microfluidic layout is important for the practical use of these structures for fluorescence, absorbance and SERS sensing.

It should be noted that the ideas and principles set forth herein for chemically synthesized 1D semiconductor nanostructures are entirely compatible with existing lithography techniques. State-of-the-art electron beam and other lithography methods currently offer better size control, reproducibility, and processing speeds to produce subwavelength optical probes and spectrometers than the serial approach discussed here. Future experiments will include lithographically defined structures on various support substrates to discern the limits of detection using nanoscale optics.

In terms of present industrial efforts and interests in small volume detection, NanoDrop© Technologies has developed a UV/Vis spectrometer (ND-1000) based on patented sample retention technology. The instrument is generally used to detect 1 μL to 2 μL nucleic acid aliquots with a sample detection limit of 2 ng/μL (dsDNA). The path length for the Xe flash lamp (220 nm to 750 nm) is held relatively fixed at 1 mm. The major advantages of a subwavelength spectrometer over the commercially available unit is smaller volume size (~$10^6$ times smaller), shorter path lengths (~10 times shorter), and possibly higher sensitivity with the advanced multi-pass geometries.

Optical Routing with Nanoribbons and Nanowire Assemblies

The manipulation of optical energy in structures smaller than the wavelength of light is key to the development of integrated photonic devices for computing, communications and sensing. We assembled small groups of freestanding, chemically synthesized nanoribbons and nanowires into model structures that illustrate how light is exchanged between subwavelength cavities made of three different semiconductors. The strength of the optical linkages formed when nanowires are brought into contact depends both on their volume of interaction and angle of intersection. Using simple coupling schemes, lasing nanowires can launch coherent pulses of light through nanoribbon waveguides that are up to several millimeters in length. Also, inter-wire coupling losses are low enough to allow light to propagate across several right-angle bends in a grid of crossed nanoribbons. The fraction of the guided wave power traveling outside the nanowire/nanoribbon cavities is utilized to link nanowires through space and to separate colors within multi-ribbon networks. In addition, we find that nanoribbons function excellently as waveguides in liquid media and provide a unique way to probe molecules in solution or in proximity to the waveguide surface. Our results lay the groundwork for photonic devices based on assemblies of active and passive nanowire elements and presage the use of nanowire waveguides in microfluidics and biology.

EXAMPLE 3

SnO$_2$ nanoribbons were synthesized by the chemical vapor transport of SnO at 1100° C. in flowing argon. ZnO nanowires were grown as epitaxial arrays on sapphire substrates by the oxidation of metallic zinc at 800° C., using gold as a catalyst. GaN nanowires were made by the chemical vapor transport of gallium in a NH$_3$/H$_2$ mixture at 900° C., with nickel as the catalyst. The SnO$_2$ nanoribbons were dry transferred en masse to oxidized silicon substrates (600 nm SiO$_2$, Silicon Sense Inc.). A triple-axis micromanipulator tipped with a tungsten probe (~400 nm tip diameter) was used to remove individual ZnO and GaN nanowires (chosen by their PL spectra) from their growth substrates and then deposit them with the nanoribbons.

EXAMPLE 4

Nanoribbons and nanowires were manipulated with the probe under a dark-field microscope. A HeCd laser provided continuous wave (CW) resonant illumination (325 nm), while the fourth-harmonic of a Nd:YAG laser (266 nm, 8 nm, 10 Hz) was used for pulsed pumping. Laser diodes (652 nm and 532 nm) and the HeCd laser (442 nm) supplied visible light for the filtering and fluorescence demonstrations. The lasers were focused to a beam diameter of approximately 50 μm, giving a CW power density of approximately 175 W/cm$^2$ and a pulsed energy density of approximately 10 μJ/cm$^2$. Spectra were acquired with a fiber-coupled spectrometer (gratings at 150 and 1200 grooves/mm, SpectraPro 300i, Roper Scientific) and liquid N$_2$-cooled CCD setup. Black-and-white and color images were recorded with two microscope-mounted CCD cameras (CoolSnap fx and CoolSnap cf, Photometrics).

Many of the nanoribbons/wires described herein operated as single-mode fibers for some of the experimental wavelengths, while others were multi-mode. For reference, the approximate single-mode cutoff diameters of a cylindrical step-index fiber in air are 140 nm (λ=365 nm) and 265 nm (λ=600 nm) for SnO$_2$, 112 nm (λ=365 nm) for GaN, and 140 nm (λ=380 nm) and 220 nm (λ=510 nm) for ZnO.

In the liquid experiments, large droplets (~5 μL) of water or various alcohols were transferred to the oxide surface by pipette. The solvent droplets were then diced into smaller volumes (as small as 100 fL) and positioned on the surface using the manipulator.

Nanoribbon and Nanowire Sizes Were Determined with a Scanning Electron Microscope (SEM)

FIG. 17 and FIG. 18 document several experiments that were performed with a single nanoribbon in various combinations with GaN and ZnO nanowires.

FIG. 17 illustrates the routing of GaN PL and lasing emission. FIG. 17A is a dark-field optical image of a coupled GaN nanowire 50 and SnO$_2$ nanoribbon 52. The label A denotes the location of the junction. FIG. 17B shows direct excitation of the SnO$_2$ nanoribbon at location B generates white PL that is guided to the ends of the SnO$_2$ cavity. Some of the light is scattered by a large particle found at C. The inset in FIG. 17B is a magnified view of the bottom emission spot. FIG. 17C is a magnified view of the junction area. The inset in FIG. 17C is a SEM image showing that the two structures are staggered over 9 μm and touch for approximately 2 μm. FIG. 17D shows direct CW excitation of the GaN nanowire generates UV band-edge emission at 365 nm and a small amount of visible defect emission at 650 nm. The cavity is too thin to permit the confinement of red light, but (Inset) a UV camera detects strong waveguiding of the UV PL. FIG. 17E is an optical image of the routing of UV laser pulses from nanowire to nanoribbon. Here, the GaN cavity was pumped above its lasing threshold by a pulsed 266 nm source (itself invisible to this detector). FIG. 17F shows spectra comparing the GaN PL and lasing emission before and after passage through the nanoribbon cavity. The broad pseudo-Gaussian spontaneous emission peak (top) is broken into a series of sharp modes during its transit through the nanoribbon (WG PL). Likewise, the lasing emission at moderate pump power, which shows multiple modes (GaN lasing), is severely modulated by the mode structure of the $SnO_2$ cavity (bottom). Spectra are normalized and offset for clarity.

Figure 17A:
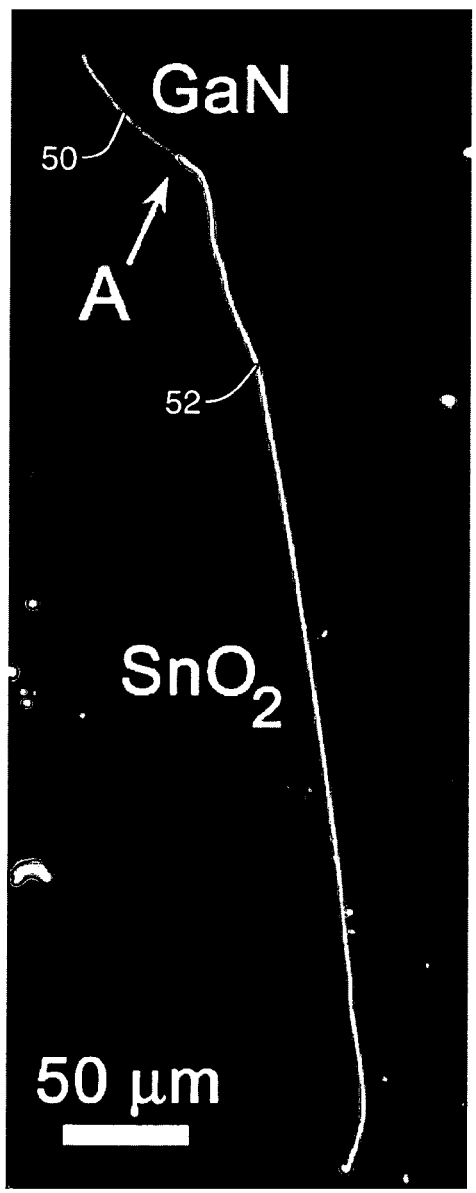
Figure 17B:
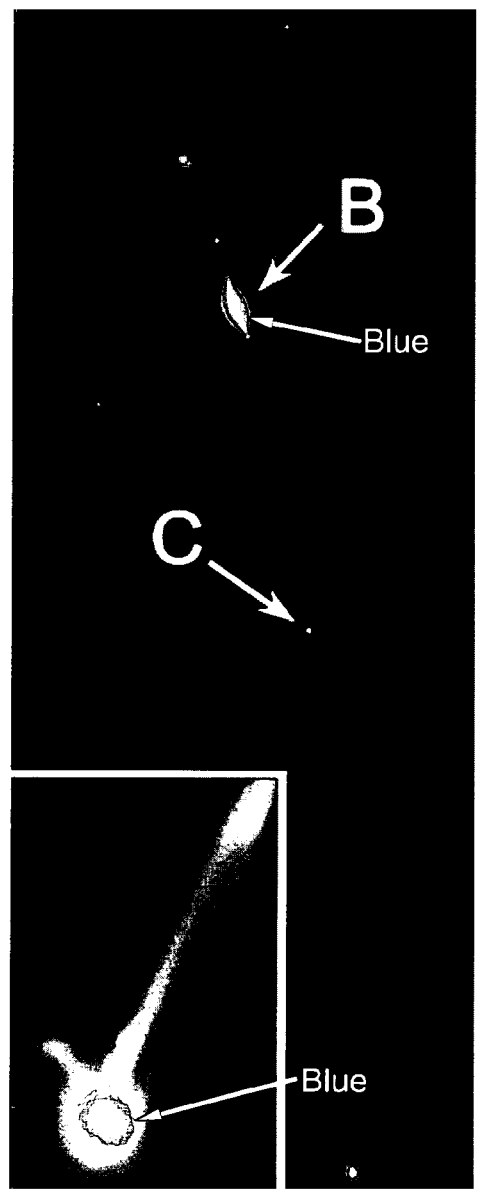
Figure 17C:
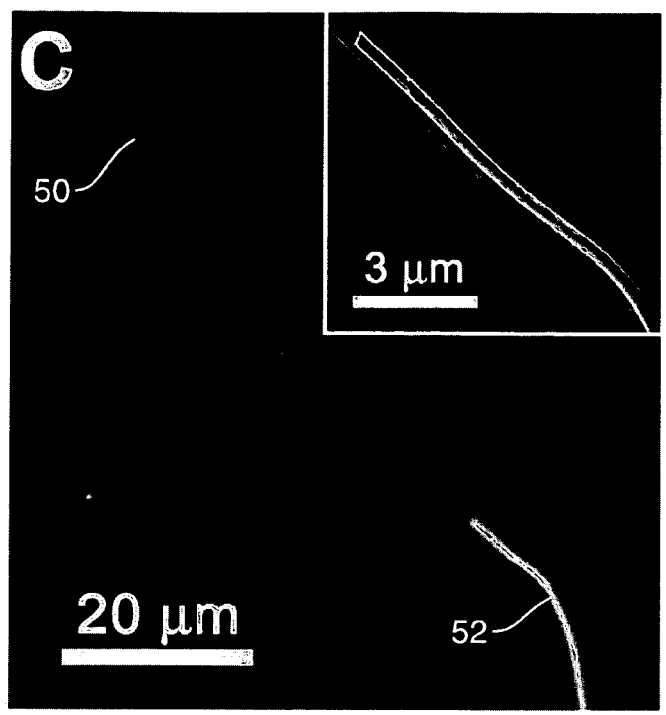
Figure 17D:
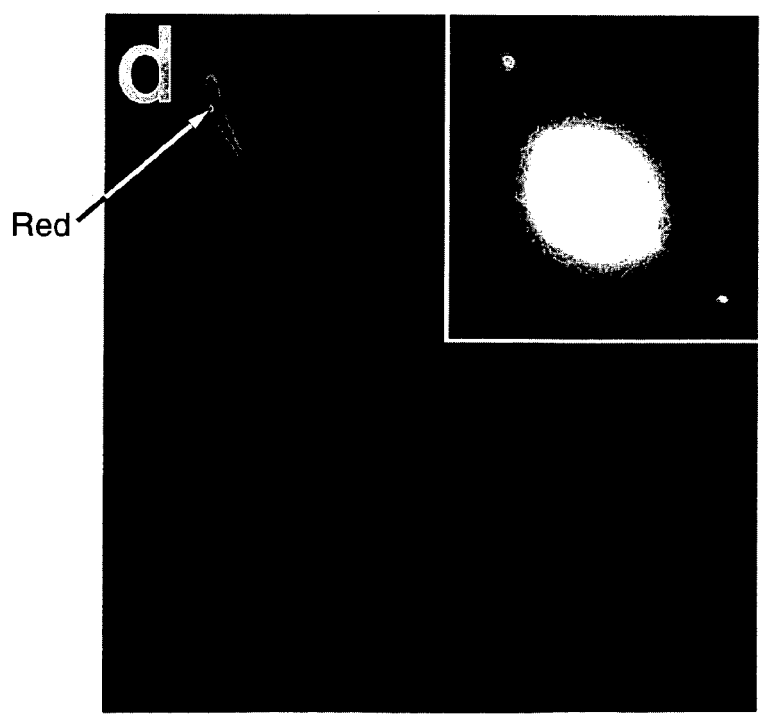

As can be seen, FIG. 17A shows a GaN nanowire (130 nm by 65 μm) that has been coupled to a $SnO_2$ nanoribbon (240 nm by 260 nm by 460 μm) with the micromanipulator. The magnified SEM view of the GaN—$SnO_2$ junction (Inset, FIG. 17B) indicates that the two structures are in physical contact over an interaction length of approximately 2 μm. This staggered-bonded configuration provides good optical coupling between the cavities and some degree of inter-wire adhesion (via electrostatic forces), which aids in the construction of multi-wire networks. Butt-end coupling is also effective, and it is possible for us to detect the transfer of light between nanowire cavities that are weakly coupled across an air gap of up to several hundred nanometers (not shown). If two nanoribbons are crossed instead of staggered, the coupling losses decrease with shallower intersection angles, which has also been observed recently for crossed CdS nanowires.

To demonstrate the routing of continuous wave light, we excited the GaN nanowire with the focused beam of a HeCd laser operating at 325 nm. Band-edge PL from the GaN cavity was channeled through the $SnO_2$ nanoribbon to emerge primarily at its far end. A fraction of the light was also scattered by imperfections along the length of the nanoribbon (i.e., attached particles or macroscopic step edges). Far-field spectra collected from the output end of the nanoribbon (FIG. 17F) show that the quasi-Gaussian PL band of GaN is imprinted with the mode structure of the $SnO_2$ cavity during its transit. This mode structure is not longitudinal (Fabry-Perot) in nature, as it is for shorter nanowires; instead, it is a complex interference pattern dependent on nanoribbon shape and cross-sectional dimensions, among other factors.

Moreover, referring also to FIG. 18, it is possible to simultaneously guide the output of two (or more) nanolasers by coupling multiple ZnO and GaN nanowires to the same nanoribbon, opening up the possibility of performing nonlinear wave mixing within single nanocavities. FIG. 18A is a dark-field image of a GaN nanowire 54 and a ZnO nanowire 56 coupled to the same nanoribbon 58. The scale bar is 10 μm. FIG. 18B shows the spectrum of guided light collected at the far end of the nanoribbon when both nanowires were pumped above their lasing thresholds by the same train of optical pulses. The nanoribbon is the same used in FIG. 13 and FIG. 17.

Note that in contrast to their continuous wave emission, the pulsed emission of ZnO and GaN is nearly devoid of visible PL since the defect bands experience no gain. This is experimental verification that coherent optical pulses can be transferred between nanowires and steered hundreds of micrometers from their source. With high frequency electrical pumping, nanowire laser/waveguide combinations could be used to transduce and shuttle packets of electro-optical information within future computing and communications devices.

Figure 17E:
Figure 17F:
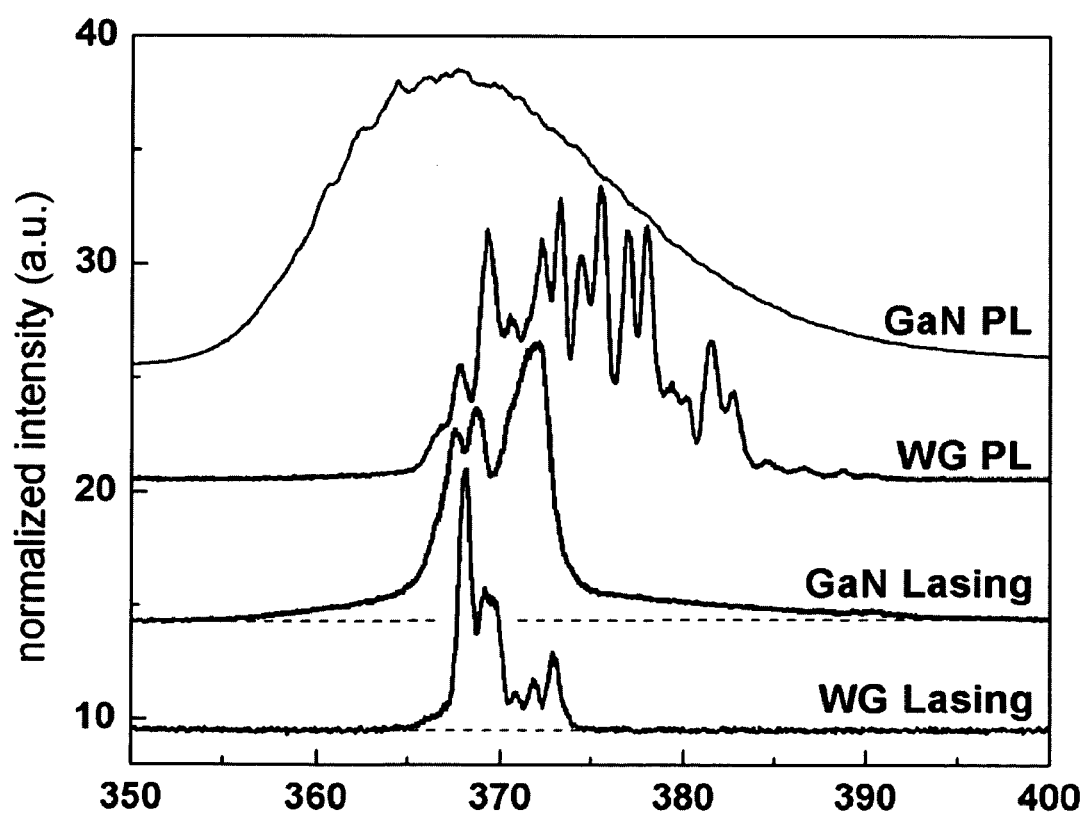

FIG. 19 illustrates GaN nanowire lasing. FIG. 19A shows a series of emission spectra at different pump fluence for an isolated GaN nanowire with a diameter of 150 nm and length of 45 μm. The inset in FIG. 19A shows the PL spectrum. FIG. 19B shows the energy curve for the same nanowire. Typical thresholds for GaN NW lasing were 5 μJ to 15 μJ $cm^{-2}$. The inset in FIG. 19B is an image of lasing emission from a different GaN nanowire, showing its pronounced spatial pattern. By pumping the GaN nanowire above its lasing threshold (~5 μJ/$cm^2$) with pulsed UV excitation, we were able to send single optical pulses from the nanowire laser through the nanoribbon waveguide (FIG. 17E). The spectrum of several thousand accumulated pulses (FIG. 17F) shows a series of sharp modes (FWHM=0.8 nm) slightly red-shifted from the band edge of GaN. These are the Fabry-Perot type lasing modes of the GaN nanowire resonator, modulated in intensity by the nanoribbon cavity. We have obtained similar results with junctions between nanoribbons and lasing ZnO nanowires.

Referring now to FIG. 20 and FIG. 21, since diffraction losses in a subwavelength cavity increase markedly with wavelength, a nanoribbon waveguide preferentially confines the bluer portion of any non-monochromatic beam. As a result, nanoribbons act as short-pass filters with cutoff wavelengths that are determined by their cross-sectional dimensions and overall length.

FIG. 20 shows color filtering in a nanoribbon network 60. FIG. 20A is a dark-field image of a four-ribbon assembly as it guides white PL generated at the pump spot (left) and separates it into a different color at the end of each nanoribbon (right). The scale bar is 50 μm. FIG. 20B is a magnified view of the emission region. The branch nanoribbons 1-3 in FIG. 20B emitted green, aqua and blue light because of their progressively smaller cross-sections (350 nm by 140 nm, 260 nm by 175 nm and 210 nm by 135 nm, respectively). Their 50% cutoff wavelengths were determined by near-field scanning optical microscopy (NSOM) to be 543 nm, 502 nm and 478 nm. The stem nanoribbon is 260 nm by 240 nm by 390 μm. FIG. 20C shows that non-resonant blue light is transmitted to the end of all four nanoribbons, while FIG. 20D shows that green light is much more strongly guided by nanoribbon 1 than by nanoribbon 3 and FIG. 20E shows that red light is filtered out by all three branches. The scale bar is 20 μm.

As can be seen from FIG. 20, we assembled a simple network comprising four nanoribbons of different sizes to show how such a structure may be used to separate colors. When excited at 325 nm, the large nanoribbon that formed the stem of the network 60 emitted white light composed of two broad $SnO_2$ PL bands centered at 495 nm and 590 nm, as can be seen from FIG. 21 which is a typical PL spectrum of a $SnO_2$ nanoribbon showing its two defect bands. Varying amounts of the stem emission then flows into the three shorter and consecutively thinner branch nanoribbons, separating the white light into green, aqua and blue components (ribbons 1-3). Alternatively, when monochromatic red light was launched into the stem only the stem nanoribbon lit up, while green light was guided strongly (weakly) by the largest (smallest) branch and blue light passed through all three branches as well as the stem (FIG. 20B-20D). Although this color filtering effect works only in short-pass mode, and so cannot, for instance, isolate the pure red component of a white beam, it may prove useful in such tasks as removing visible contamination from UV pulses or providing local excitation for fluorophores with narrow absorption bands, such as quantum dots.

Referring to FIG. 22, to test the limits of inter-cavity optical coupling, we assembled four nanoribbons into a rectangular grid (46 μm long by ~25 μm wide) featuring X-junction vertices with small contact areas (<0.15 $μm^2$) (FIG. 22A and Inset). FIG. 22A is a dark-field image of the four-ribbon structure, with the input channel extending off the frame to the right and the output channels labeled 1-7. The nanoribbons vary in size from 300-400 nm on a side. (FIG. 22A and Inset). A SEM image of the junction at the lower right vertex. FIG. 22B is a PL image as the input channel is pumped at 325 nm. Light is guided to the seven output ends with different intensities and colors as described below.

The structure was designed with one long channel for light input and seven short output channels that could be monitored simultaneously. As shown in FIG. 22B, direct excitation of the input channel triggered emission from all seven of the nanoribbon outputs, with the following intensity distribution: $1 \gg 6 > 4 \approx 7 > 3 > 5 > 2$. This is exactly the sequence one would expect after considering the trajectory of the incoming light and the intensity of scattering at the four nanoribbon-ribbon junctions. The light trajectory is important here since the low reflectivity of their end facets makes nanoribbons poor resonators (with an ideal finesse of ~1.3). As such, most photons do not make multiple passes and light flow is highly directional. The right-angle intersections present significant obstacles to inter-cavity waveguiding by total internal reflection. At the same time, they act as quasi-isotropic scatterers that feed light between nanoribbons. Nanoribbon-to-ribbon losses, although nearly maximized in this geometry, are still low enough for the activation of channels 2 and 3, which require photons to negotiate two right-angle junctions and transit three separate cavities. When we added a ZnO nanowire laser to the input channel and used it to launch light into the grid, emission was detected from all channels but 2 and 3; the number of injected photons was simply too small to illuminate the parallel nanoribbon. Nanowire grids have already been employed to implement rudimentary electronic logic. Integrated optical logic and all-optical switches present exciting prospects, and our results show that grids of nanowires should be capable of routing signals for such tasks.

Due to their high refractive indices ($n \geq 2$), the nanoribbons and nanowires discussed here function well as waveguides in water and other liquids. This is a considerable advantage over subwavelength silica waveguides, which cannot efficiently confine visible light in liquids because of a low dielectric contrast ($n_{silica} \approx 1.45$). Waveguiding in liquids is especially important for integrated on-chip chemical analysis and biological spectroscopy in which small excitation and detection volumes are required.

As can be seen, chemically synthesized nanoribbon and nanowire waveguides have two unique and potentially useful features for subwavelength photonics applications. First, nanowires push subwavelength optical fibers beyond silica. The scores of materials that can now be made in nanowire form include active, passive, nonlinear and semiconducting inorganic crystals, as well as a wide variety of polymers. Simultaneous photon, charge carrier and spin manipulation is possible within and between nanowires of different compositions. Also, many of these materials have higher refractive indices than silica-based glasses, permitting light of a given wavelength to be confined within thinner structures for denser integration. This enables waveguiding in liquids and makes it possible to extend subwavelength guiding to telecommunications wavelengths using, for example, an approximately 300 nm diameter Si or GaP nanowires. Second, nanowires are freestanding, mechanically flexible elements that can be manipulated on surfaces or used as mobile probes in fluids. As such, they offer a type of versatility difficult to achieve with lithographically-defined structures that are permanently affixed to their substrates.

The disadvantages of nanowire photonics include (i) the paucity of parallel assembly methods for accurately arranging large groups of nanowires into useful structures; (ii) relatively high inter-wire coupling losses compared to monolithic waveguides formed by lithography (coupling losses could be greatly reduced if branched, multi-component nanowires were developed to replace the staggered or crossed nanowire cavities used here); (iii) the lesser geometric perfection of nanowire assemblies relative to the precise shapes and sizes definable with lithography. Geometric imprecision introduces some uncertainty in the resulting light propagation and adds complexity to nanowire experiment/theory comparisons. However, despite these limitations, nanowires and their assemblies provide an important new platform for photonics studies and applications that is only beginning to be investigated.

It will be appreciated that the subwavelength waveguide described herein can be used as a functional element in photonic circuits such as optical networks, optical filters, optical directional couplers, emitter-waveguide-detector junctions, optical probes, optical sensors, optical routers, optical junctions, optical modulators, optical Y-junctions, optical branch networks, Mach-Zehnder interferometers, optical ring oscillators, nanolasers, optical phase shifters, fluidic sensors, fluidic probes, microfluidic devices, optical spectrometers, and optical crossbar grids. Those skilled in the art will also appreciate that the nanostructures described herein can be fabricated and incorporated into devices, systems and structures using various techniques known in the art. Additionally, reference is made to U.S. Pat. No. 6,882,051, entitled "NANOWIRES, NANOSTRUCTURES AND DEVICES FABRICATED THEREFROM" issued on Apr. 19, 2005, which is incorporated herein by reference in its entirety, and to U.S. Patent Application Publication No. US 2004/0131537 A1, entitled "FUNCTIONAL BIMORPH COMPOSITE NANOTAPES AND METHODS OF FABRICATION" published on Jul. 8, 2004, also incorporated herein by reference in its entirety.

Optical Sensors

As discussed above, subwavelength waveguides can be used as optical probes and sensors. In this section, we describe a novel optical sensing platform that utilizes the evanescent field of a single-crystalline nanoribbon waveguide to perform absorbance, fluorescence and surface enhanced Raman spectroscopy (SERS) on sub-picoliter volumes of solution. We obtained the chemical specificity of SERS by decorating the waveguide with silver nanocubes to enhance the field around the nanoribbon. The waveguide sensors showed excellent chemical resistance and can withstand cleaning cycles in strong acid, making the devices reusable. These results open up the possibility of engineering hand-held, photonic sensors capable of detecting and identifying chemical species in solution. We demonstrated this by directly exciting molecules (i.e., absorbance and/or fluorescence) with the evanescent field or by scattering light off metallic nanoparticles immersed in the evanescent field to enhance local Raman modes. Our nanowire optical sensing platform complements nanowire field effect sensors with the ability to monitor optical attenuation across the wire element. However, the use of photons instead of electrons allows optical spectroscopy to be carried out on the analyte.

To simplify the material manufacturing we chemically synthesized optical waveguides with sub-200 nm diameters to expose a substantial amount of the guided optical intensity to the surrounding matrix. This field was strong enough to optically interrogate molecular species without disrupting the operation of the waveguide.

FIG. 23A-C illustrate a device layout of an evanescent field sensor 100 according to the invention. FIG. 23A is a photograph of a device showing the PDMS microfluidic sensing channels 102 and supporting quartz coverslip 104 (shown in FIG. 23C). The lower inset is a magnified dark-field image of the five microfluidic sensing channels 102. The upper inset is a schematic diagram showing the inlet/outlet ports 106*a*, 106*b* and location of the waveguides 108. FIG. 23B is a dark-field/luminescence image of a single $SnO_2$ waveguide bridging two sensing channels. The waveguide is optically pumped outside the field of view (bottom left) and the guided emission is routed to the end facet at top right. FIG. 23C is a schematic diagram of the device orientation once mounted to the microscope in relation to the objective 110, for acquiring the corresponding images shown in FIG. 23A-B.

Figure 24A:
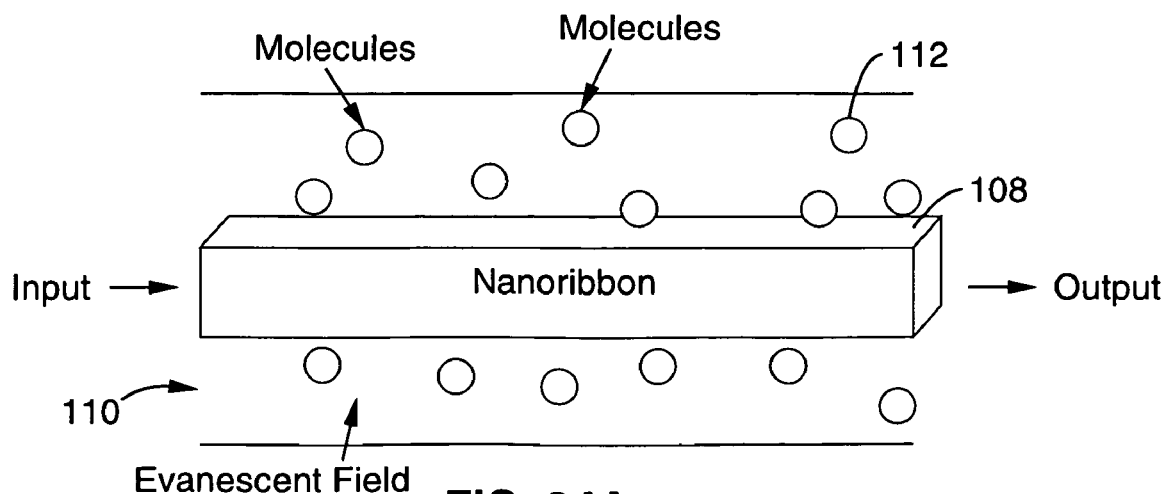
Figure 24B:
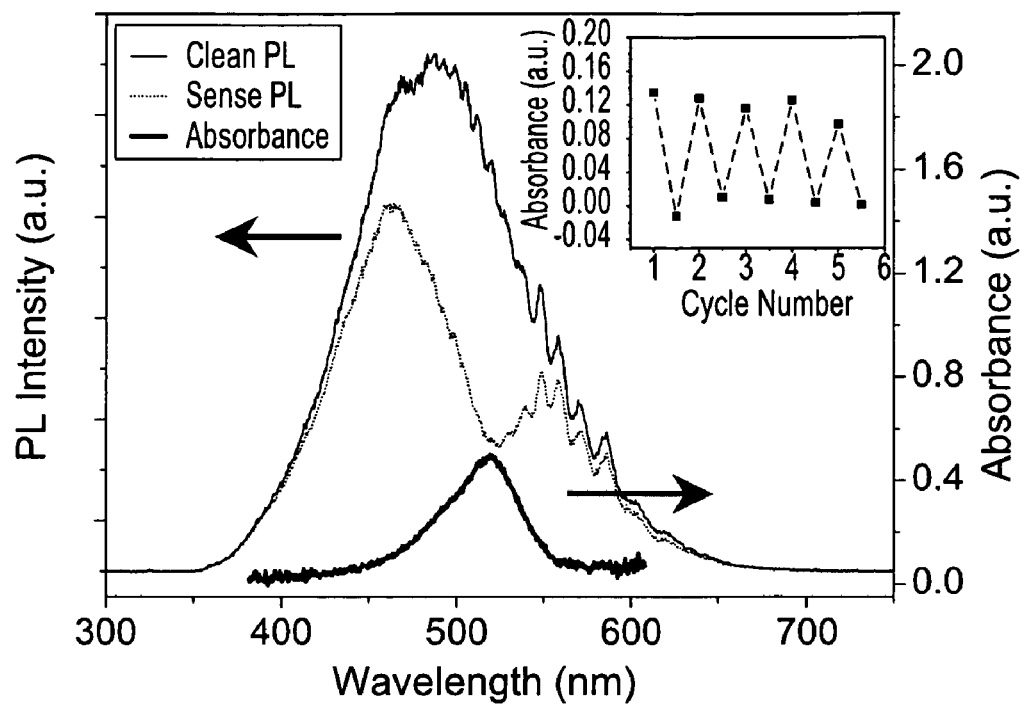
Figure 24C:
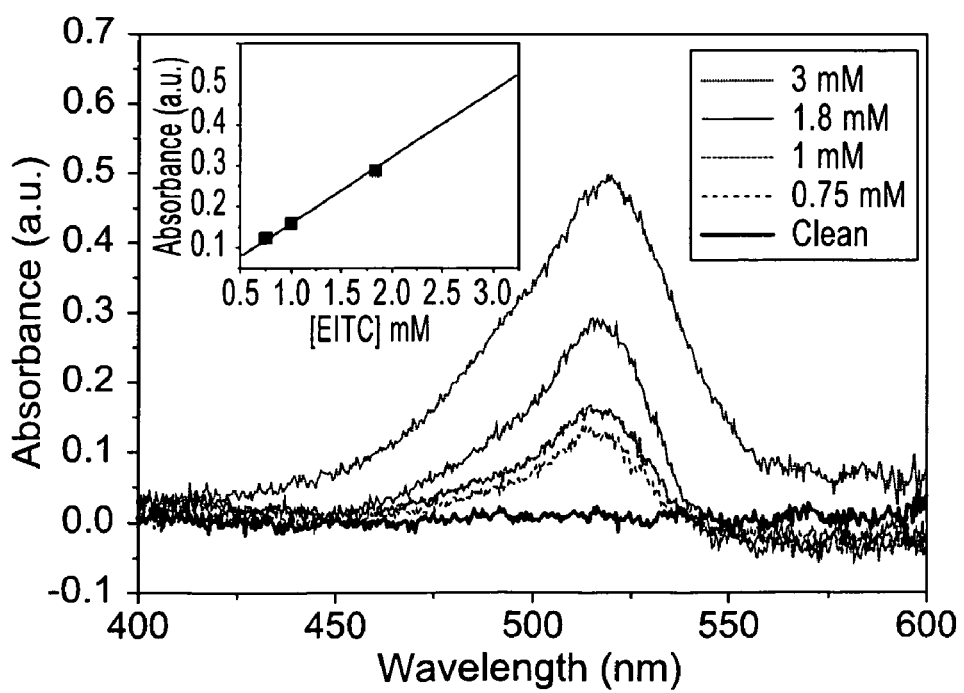
Figure 24D:
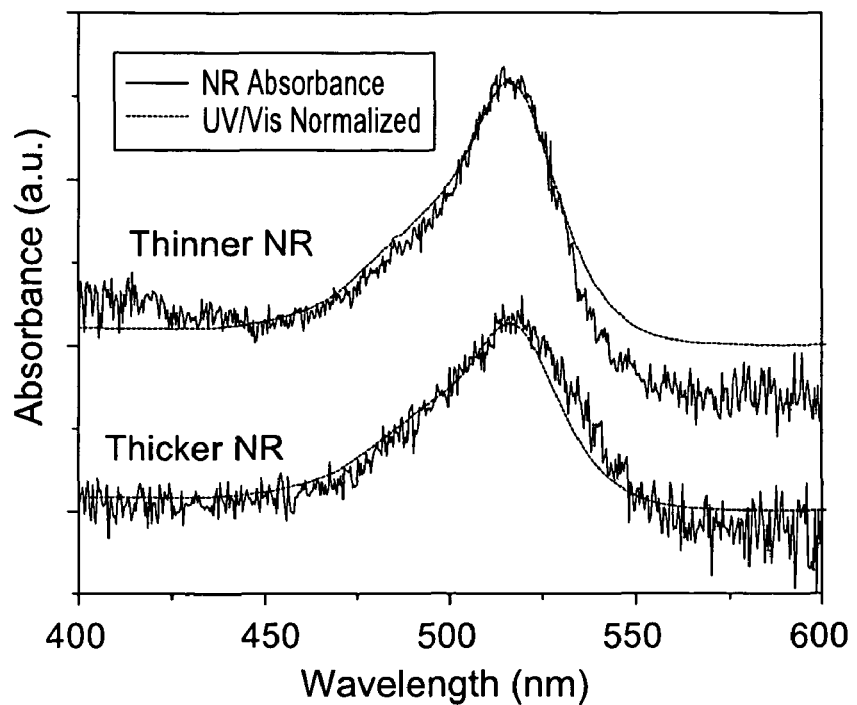
Figure 24E:
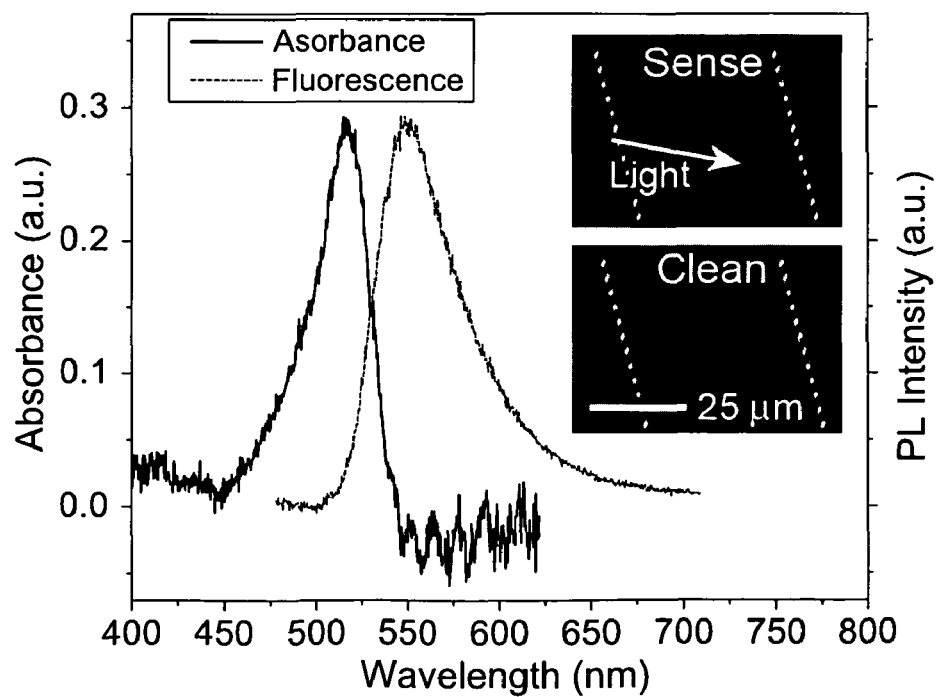
Figure 24F:
Figure 24G:
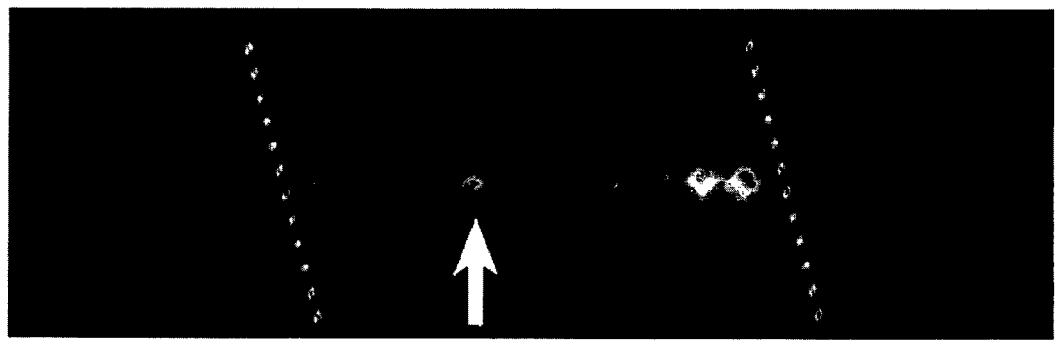
Figure 24H:
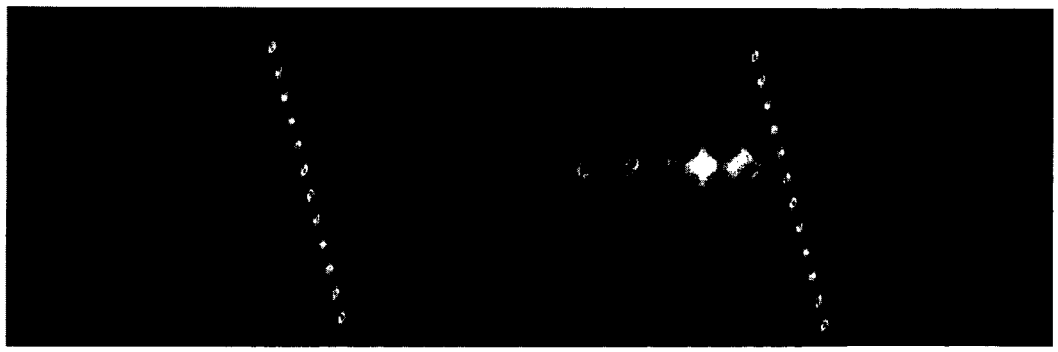

FIG. 24A-H illustrate use of evanescent wave sensors in absorbance and fluorescence modes. FIG. 24A is a diagram showing the absorbance geometry, and shows a nanoribbons 108 in relation to an evanescent field 110 and molecules 112. FIG. 24B shows raw waveguided fluorescence spectra before (clean PL—thin black line) and during (sense PL—dotted line) the flow of a 3 mM solution of EITC through a single sensing channel. The resulting absorption spectrum is shown in the lower thick black line. The inset shows cycling the device through multiple sensing cycles using pH12 water to clean the waveguide. FIG. 24C shows the absorption spectra of four EITC solutions of different concentration. The inset shows peak absorbance versus EITC concentration showing the linear response of the sensor in this range. FIG. 24D is a comparison of thin (d<150 nm) and thick (d>200 nm) nanoribbon waveguides. The upper and lower solid traces are the raw waveguide absorption data and the upper and lower thin dashed traces (normalized) were taken with a conventional UVN is spectrometer. FIG. 24E shows overlaid absorbance and fluorescence spectra of a 1.84 mM EITC solution using the same waveguide. The insets are photoluminescence images of a sensor in the presence of EITC (upper image) and water (lower image). FIG. 24F-H are a series of photoluminescence images captured at 5 ms (187 Hz) of λ-DNA-YOYO1 molecules flowing past a sensor. Here, 442 nm light (<10 nW) is guided from right to left. The arrow in FIG. 24G denotes a single molecule passing through the evanescent field.

FIG. 25A-C illustrate dielectric scattering and refractive index sensing with silver nanoparticles. FIG. 25A is a dark-field image of a $SnO_2$ waveguide bridging a single sensing channel. The arrows denote the direction of the light and fluid flows. FIG. 25B shows scattering images recording Ag nanoparticles (NPs) as they stick to the waveguide surface. White light was launched through the waveguide from left to right by pumping its end (outside the field of view) with 325 nm light. From top to bottom, the time elapsed is ~30 seconds. A metal-decorated waveguide was also introduced with a 1:1 $HCl/HNO_3:H_2O$ solution (not shown). From top to bottom, the time elapsed for cleaning is 30 seconds. FIG. 25C shows raw scattering spectra collected from the channel as various liquids flow across the waveguide. The upper inset shows scattering intensity versus the index of refraction showing the expected linear response. The inverse dependence of intensity on the index of refraction is caused by the increase in waveguide loss as the cladding index increases. The insets on the lower right show scattering images taken from the adsorbed Ag nanoparticles in ethanol (n=1.36) and glycol (n=1.43).

FIG. 26A-C illustrate a nanoribbon evanescent wave SERS sensor. FIG. 26A is a schematic diagram of the sensing scheme. Analyte molecules 112 in close proximity to a metal-decorated (by, for example, Ag nanoparticles 114) nanoribbon are excited by the surrounding evanescent field and show amplified Raman scattering, which is then detected with the microscope objective 110 (FIG. 23C). FIG. 26B shows resonant SERS spectra of 100 mM Rhodamine 6G. Light was delivered to the particles by direct excitation (red line) or by the evanescent field of the waveguide (SERS R6G WG traces). Large (d~500 nm) and small (d~150 nm) waveguides yielded identical spectra. The background (dashed trace, second from bottom) was acquired with the beam positioned off the end facet of the waveguide. A Raman spectrum of PDMS (bottom solid trace) verifies that the background results from PDMS. The insets show scattering images taken of the large (top) and small (bottom) waveguides. FIG. 26C shows non-resonant SERS of bound dodecanethiol. Direct (Thiol Confocal—top line) and waveguide-excited (Thiol WG—second line from top) SERS spectra both show the distinct C-C stretching modes of the thiol ligands at 1080 and 1122 cm$^{-1}$. Background (third line from top) and PDMS Raman (bottom line) spectra are provided for clarity.

FIG. 27A-B illustrate absorbance spectra of a positively charged dye, rhodamine 6G. FIG. 27A shows fluorescence from a $SnO_2$ waveguide after traveling through the dye. The attenuated portion of the fluorescence increases as a function of time due to multilayer formation of the dye on the negatively charged $SnO_2$ surface. FIG. 27B shows absorption spectra from the same series shown in FIG. 27A along with a normalized absorption spectrum from a conventional UV/Vis spectrometer. The inset shows peak absorbance plotted verses time. The linear fit compared to the Langmuir isotherm curve suggests multilayers of the cationic dye are forming on the surface of the waveguide.

Figure 28D:
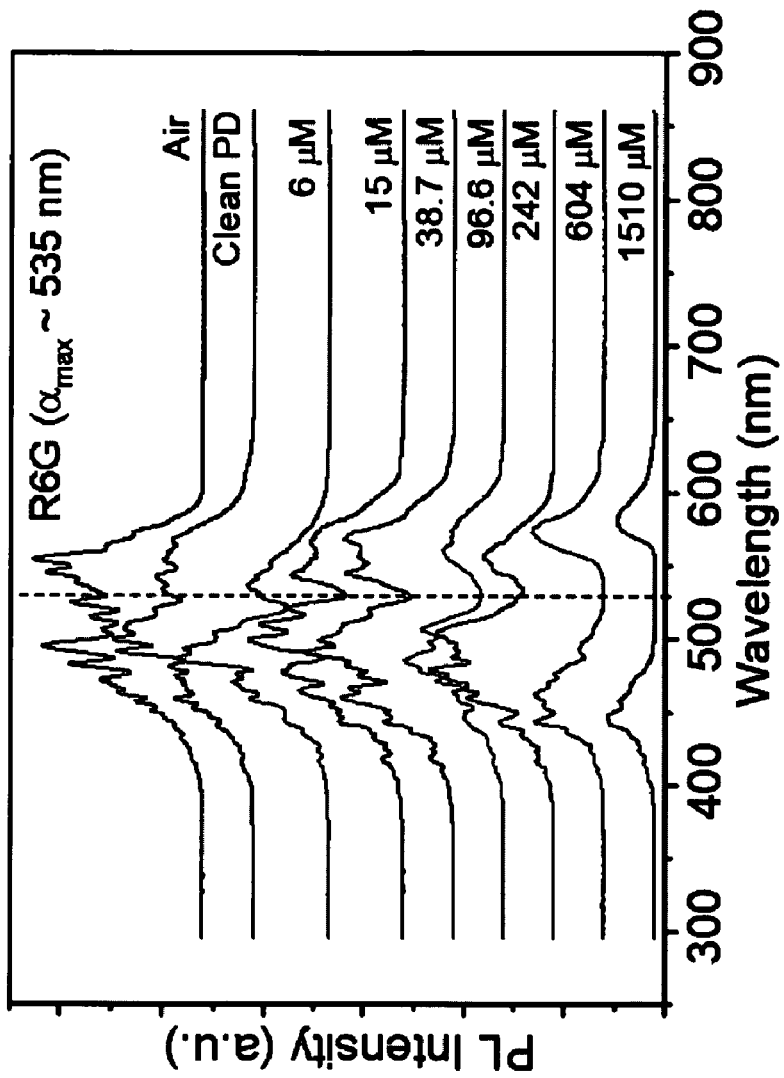

FIG. 28A is a schematic of two coupled nanoribbons for multi-pass absorption showing two possible locations for the analyte. The first ribbon 108*a* (NR 1) is shaped into a ring 116 and a second ribbon 108*b* (NR 2) is evanescently coupled so a portion of the signal is routed to a detector 116. FIG. 28B-C are images of two $SnO_2$ nanoribbon waveguides physically manipulated into the structure depicted in FIG. 28A. The inset is an image taken after placing a small droplet of 1,5-pentanediol (PD) on the sensing region of the ring. FIG. 28D shows spectra recorded on the output end of NR 2 in FIG. 27B) after placing PD droplets, loaded with various concentrations of rhodamine 6G dye, on NR 1. Spectra were taken ~5 s after droplet deposition.

EXAMPLE 1

Tin dioxide ($SnO_2$) nanoribbons were synthesized through a chemical vapor transport process. An alumina boat filled with tin monoxide powder was heated (1100° C.) in an alumina tube under a continuous flow of argon (300 torr) for ~2 hours. After removing the boat from the tube furnace, the nanoribbons were deposited on a clean glass substrate for optical characterization (see below). For surface enhanced Raman spectroscopy (SERS) detection, silver nanocrystals were prepared using a modified polyol process in which silver nitrate is reduced in a solution of 1,5-pentanediol (~190° C.) in the presence of a capping polymer.

All experiments were performed with an upright dark-field microscope operating in reflection mode. Monochromatic laser light was focused onto the sample at a 35° angle normal to the substrate. Broadband light (FWHM>200 nm) was generated in the waveguide by exciting the $SnO_2$ nanoribbon with the 325 nm line of a continuous-wave HeCd laser (Melles Griot, Irvine, Calif.). The broad luminescence of the waveguide was used for the absorbance measurements by detecting the guided light with and without the analyte present. Fluorescence and SERS spectra were captured by focusing either a 442 nm (HeCd) or 532 nm (CW diode) laser spot on one of the end facets of the waveguide. The signal was collected by a 50× objective (Nikon, 0.55 NA) and routed through a fiber to a spectrometer (150 grooves/mm grating, SpectraPro 300i, Roper Scientific, Trenton, N.J.) equipped with a liquid nitrogen cooled CCD. Images were captured either with a digital color camera (CoolSnap cf, Photometrics, Tucson, Ariz.) or an EMCCD camera (iXon, Andor Technology, Belfast, Northern Ireland).

Microfluidic flow cells were cast from polydimethylsiloxane (PDMS) using standard lithography. A silicon master containing five parallel channels (channel lengths of 1.5 mm and inter-channel separation of 100 μm) was prepared with 50 μm wide×50 μm deep channels. After casting and curing PDMS on the silicon master, the stamps were removed from the master, cleaned with ethanol and dried. To increase exposure of the analyte to the surface area of the cavity, the waveguides were deposited in a wet PDMS layer (~5 μm thick) inked on the structured side of the stamp. This also ensured complete sealing of the channels with the quartz substrate after PDMS curing and eliminated capillary leakage between adjacent channels. With the PDMS layer uncured, nanoribbons were placed across the channels using a micromanipulator (Märzhäuser Wetzlar, Wetzlar-Steindorf, Germany) equipped with an etched tungsten probe. Only ribbons with lengths greater than 350 μm were used in the devices. The stamp was then immediately bonded to a quartz substrate, giving the final device architecture shown in FIG. 23A after curing the wet layer. The sharp waveguide/PDMS interfaces can be seen in FIG. 23B which is a dark-field/luminescence image of a single $SnO_2$ waveguide bridging two sensing channels. The waveguide is optically pumped outside the field of view (bottom left) and the guided emission is routed to the end facet at top right. Referring to FIG. 23C, the optical experiments were carried out with the device oriented horizontally in the microscope with the quartz substrate facing the collection objective. Analyte solutions were pulled through the channels using a syringe pump operating at flow rates of 0.75 mL/h-3 mL/h.

Unless specified, waveguides were chosen for sensing if their single-mode cut-off wavelengths were 550 nm or shorter. Waveguides were screened optically on a silica surface by pumping one of the ends of the nanoribbon with above band gap light ($E_g$=3.6 eV) from the HeCd laser (3.81 eV), and collecting the waveguided defect emission in the far-field at the opposite end of the ribbon. The empirical cut-off wavelength (~550 nm) for the waveguides was determined by identifying the 50% transmission point (inflection point) in the collected emission spectrum. Using the waveguide parameter for a cylindrical fiber, the single-mode cut-off wavelength takes on the form $\mu=d\pi/2.405(n_{co}^2-n_{cl}^2)^{1/2}$ where d is the single-mode cut-off diameter of the waveguide and $n_{co}$ and $n_{cl}$ are the refractive indices of the waveguide core (n=2.1) and cladding (n=1), respectively. Although the nanoribbons have rectangular cross-sections, we found this generalized expression gives cut-off diameters on the order of 200 nm, in good agreement (d=150-200 nm) with the dimensions of the ribbons used.

EXAMPLE 2

We used $SnO_2$ nanoribbons as the passive optical components in the devices because their high index of refraction allows efficient waveguiding through the microfluidic devices and analytes. In addition, their superb chemical and mechanical properties allow them to withstand harsh cleaning conditions.

The first spectroscopic experiment performed with the optical waveguides was the acquisition of an absorption spectrum. This is achieved by generating the featureless defect emission on one side of the sensing channel and collected on the opposing side after it is guided through the analyte (see FIG. 23B). The dye chosen for the absorption measurements was eosin-5-isothiocyanate (EITC) (Molecular Probes) which is a common amine-reactive probe used to conjugate proteins or amine-modified oligonucleotides. EITC solutions were prepared in water (pH 12) with concentrations ranging from 0.75 mM to 3 mM. The solutions were pulled into the channel and sensed under continuous flow. The initial waveguided intensity ($I_O$) is compared to the sensing intensity ($I_S$) to determine the absorbance (A) of the solution according to A=log[$I_O/I_S$] (FIG. 24B). The attenuated fraction of $I_S$ is directly related to the absorbance of the analyte species. The waveguides are cleaned (FIG. 24B-*inset*) by pulsing pure solvent (in this case pH12 water) into the channel. The concentration dependence is linear with a molar absorptivity ($\epsilon$) of 31,000 M-1 cm$^{-1}$, which is ~3× lower than estimated values for EITC in 0.01 M NaOH. Although the surface of the $SnO_2$ nanoribbon is negatively charged at this pH (isoelectric point ~5) and EITC carries a net-negative charge, a slight enrichment of the analyte near the waveguide/PDMS interface may occur due to Van der Waals forces between the EITC molecules and polymer. This interaction would cause a lower molar absorptivity as seen in the EITC data. When cationic dyes such as Rhodamine 6G are pulled through the flow cells, multi-layers form on the surface of these waveguides (see FIG. 27).

As the $SnO_2$ defect emission travels through the sensing region it is attenuated according to $I_S=I_O \exp^{-\epsilon \kappa L c}-I_O(NA_O^2/NA^2)$ where $\epsilon$ is the molar absorptivity of the analyte (M$^{-1}$ cm$^{-1}$), $\kappa$ is the percent power in the evanescent field, L is the sensor length (cm), c is the analyte concentration, and NA and $NA_O$ ($NA=(n_{co}^2-n_{cl}^2)^{1/2}$) are the numerical apertures of the waveguide with and without the analyte, respectively. This is a simplified expression that neglects chemical enrichment around the $SnO_2$ ribbon, the shape of the cavity and the dispersion of the field penetration; however, it gives estimates ranging from 15% to 30% for the power available in the evanescent field for the waveguide dimensions used here. These results agree well with calculations describing the percent power in the core ($\eta$) of a step index fiber which use the function $\eta=1-[5.784 \exp(-2/V)/V^3]$ where $V=\pi d/\lambda(n_{co}^2-n_{cl}^2)^{1/2}$ (d is the diameter of the fiber). For example, a 200 nm fiber ($n_{co}$=2.1) guiding 500 nm light in water ($n_{co}$=1.33) contains ~80% of the power within the core and ~20% in the evanescent field. The penetration depth (defined where the field intensity decays to 10% of the core power) is calculated to be about 125 nm, leading to a probe volume of less than 10 femtoliters for a 50 μm path length. With some simple modifications to path length, index of analyte and cavity size, it should be possible to reach <100 attoliter ($10^{-18}$ L) probe volumes. The detection limit for absorption with a single pass through the analyte is ~0.3 mM, but improvements should be possible by utilizing multi-pass ring geometries (see FIG. 28). Initial experiments were performed by molding ribbons into ring structures on a silica surface and placing free-standing analyte droplets on the waveguide. With this scheme, however, it is difficult to control the path length of the sensing regions due to capillary wetting of the analyte along the waveguide surface. To lower the detection limit of absorption, and control the size of the sensing region, it will be important to integrate such designs within a microfluidic flow cell.

Since photons emitted near the ribbon surface can be recaptured by the waveguide, the resulting absorption line shape can be skewed. This causes an artificial decrease in the calculated absorption for longer wavelengths (FIG. 24D—top trace). We observe such an artifact only in thinner waveguides (diameters <150 nm), which carry a larger percentage of the guided field intensity in the cladding. For thicker nanoribbons (diameters >200 nm) the number of photons coupled back into the waveguide is reduced, but the absorption linewidth is slightly larger (FIG. 24D—bottom trace). This can be explained by the variation in penetration depth of the evanescent field as a function of wavelength. Longer wavelengths (in this case >525 nm) show an increase in the absorption because they penetrate deeper into the solution. For all ribbons sizes, however, the peak maximum matches that from a commercial photospectrometer to within ~2 nm. More accurate peak shapes can be obtained by using expressions that account for the amount of light accessible to the analyte at different wavelengths as well as the photon flux that is recaptured by the waveguide.

To characterize the fluorescent signals produced by the analyte, monochromatic light is launched down the cavity to excite molecules passing through the evanescent field. This mode of detection is analogous to total internal reflection fluorescence (TIRF); however, a more intense optical field resides near the core-cladding interface of a sub-200 nm nanoribbon. As with TIRF, we observe no quenching or surface effects that alter the fluorescence spectra (FIG. 24E) of the molecules excited by the evanescent field. This is often a drawback of metal-coated surfaces which can influence the spectrum of fluorophores or macromolecules either through quenching or effects caused by molecules adsorbing to the metal surface. The fluorescence image in FIG. 24E (upper image) illustrates a typical intensity gradient along the length of a nanoribbon as 532 nm light travels though it from left to right. The decay in fluorescence intensity is a result of analyte absorption as the guided light moves across the sensing channel. Less than 100 nW is confined within the core of the waveguide in this example. The signal appears line-like because the solution is too concentrated to permit single fluorophores to be distinguished. However, individual molecules can be observed if nanomolar solutions are used. This is demonstrated in the case of YOYO-1 labeled λ-DNA (FIG. 24F-H). Here, portions of the waveguide appear to have higher concentrations of DNA near one of the edges. The likely explanation for this is the local interactions between the DNA strands and the $SnO_2$ surface causing a slight enrichment of the DNA molecules.

Light can be extracted from the waveguide by immersing particles with large dielectric constants in the evanescent field. This becomes important for ultra sensitive detection with a subwavelength fiber because a single particle can scatter a large percentage (5% to 10%) of the confined optical energy. We found that silver nanocubes 50 nm in diameter readily adsorbed to the waveguide surface and intensely scattered waveguided light (FIG. 25B). In general, strong scattering is observed when any particle entering the evanescent field has a larger index of refraction than the waveguide. For most waveguides used here (d~150 nm to 200 nm), complete attenuation of the waveguided light occurred when ~10-15 Ag nanoparticles attach to the surface (FIG. 25B—lower image). The scattering intensity from these immobilized nanocubes can be used to quantify the index of refraction surrounding the nanoribbon. This is demonstrated in FIG. 25D for three different refractive index media (air n=1, ethanol n=1.36, and glycol n=1.43). As expected the scattering intensity decreases linearly with increasing index of refraction. To remove the metal nanostructures, and regain the original waveguiding properties of the nanoribbon, the devices can be treated with a solution of aqua regia (1:1 $HNO_3/HCl:H_2O$) (FIG. 25C). This allows the ribbons to be recycled by stripping them of any residual molecules or metallic contaminant.

In addition to simple index measurements the immobilized metal particles can be utilized as substrates for surface enhanced Raman spectroscopy, where monochromatic light (532 nm) from the waveguide or from an external source excites surface plasmons. This excitation is responsible for large increases in the Raman cross-section of molecules near or adsorbed to the metal particle, allowing the collection of vibrational signatures from analytes that are otherwise undetectable with traditional Raman techniques. Resonant SERS occurs when both the analyte (in our case a dye molecule) and the metal plasmons are excited by the same wavelength of the light. To demonstrate resonate SERS we exposed the nanoribbons to a 100 μM solution of Rhodamine 6G ($\alpha_{max}$=535 nm) after decorating the waveguide surface with Ag nanocubes 114. The SERS signal was probed either directly with a diffraction-limited confocal spot focused on the waveguide (FIG. 26B—SERS R6G Confocal trace) or via waveguided light (FIG. 26B—SERS R6G WG trace). In the former configuration the waveguide acts simply as a supporting scaffold for the SERS-active particles. Here the power at the sample is ~2 μW. In the latter configuration the waveguide channels the excitation to the particles. Due to the coupling geometry the power accessible to the particles is less than 100 nW. Performing SERS with large (~500 nm) and small (~150 nm) diameter nanoribbons (FIG. 26B) confirm that a stronger Raman signal is achieved when a larger number of particles are scattering in the field of view. The thinner nanoribbon has about 20 nanoparticles contributing to the signal whereas the thicker ribbon has more than 30 nanoparticles. The number of particles attached to the surface of the waveguide was counted from CCD images under dilute nanoparticle concentrations and slow flow rates (0.75 mL/hr).

To detect a nonresonant SERS signal from the analyte, we modified the surface of the metal with 1-dodecanethiol ligands, which readily assemble into a monolayer on the metal surface. The SERS spectra in FIG. 26C clearly show the C-C stretching modes of the alkyl groups at 1080 and 1122 $cm^{-1}$ under confocal and waveguided excitation. The pump powers used were similar as described above for the Rhodamine 6G SERS. Interestingly, the signal-to-noise ratio is nearly identical for both excitation geometries, despite a lower power density for the waveguided excitation. However, the diameter of the confocal beam waist and differing number of particles in each experiment makes a quantitative comparison between the two configurations difficult. Future experiments will be needed to conclude if the evanescent field scattering is a more efficient mechanism for exciting plasmons in a metallic particle attached to a subwavelength waveguide. Nevertheless, the ability to extract chemical information using a subwavelength fiber is a critical step in the development of compact analytical devices.

As can be seen, we have demonstrated a novel photonic sensor based on subwavelength nanowires that is capable of detecting molecules in solution by absorbance, fluorescence and SERS. The future of portable all-optical sensors hinges on the provision of cheap, fast, reliable detectors capable of deconvoluting complex mixtures. An imperative step in this process is the addition of chemical specificity to the sensor while simultaneously providing a multiplexed geometry for high-throughput analysis. Device portability will certainly benefit from the advent of on-chip microcavity lasers and the continual efforts of integrating both active and passive optical elements on a single photonic chip. Use of the evanescent field to guide light and perform spectroscopy will undoubtedly play a major role in the design of compact optical sensors. The initial results shown here are promising for the development of on-site analytical experimentation, field detection of biochemical toxins and portable analysis of water contaminants.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A subwavelength optical waveguide, comprising:
    a $SnO_2$ nanoribbon and ZnO nanowire each having a diameter that is less than the wavelength of light to be guided;
    wherein said $SnO_2$ nanoribbon and ZnO nanowire are configured to propagate light without gain;
    wherein said waveguide is a functional element in an optical directional coupler; and
    wherein said optical coupler comprises a hetero-junction created between a single ZnO nanowire and a $SnO_2$ nanoribbon.

2. A subwavelength optical waveguide, comprising:
    a nanoribbon having a width that is less than the wavelength of light to be guided;
    wherein said waveguide is configured to propagate light without gain;
    wherein said waveguide is a functional element in an optical junction; and
    wherein said optical junction comprises a $SnO_2/SnO_2$ junction formed by coupling two nanoribbon waveguides at end facets.

3. A subwavelength optical waveguide as recited in claim 2:
    wherein said waveguide is a functional element in a photonic circuit selected from the group consisting essentially of optical junctions; and
    wherein said optical junctions are selected from the group consisting essentially of emitter-waveguide-detector junctions, and optical Y-junctions.

* * * * *